United States Patent
McLaren et al.

(10) Patent No.: US 11,986,595 B2
(45) Date of Patent: May 21, 2024

(54) RESPIRATORY MASK SYSTEM

(71) Applicant: Fisher & Paykel Healthcare Limited, Auckland (NZ)

(72) Inventors: Mark Arvind McLaren, Auckland (NZ); Brett John Huddart, Auckland (NZ); Jeroen Hammer, Auckland (NZ); Matthew Robert Geoff Slight, Auckland (NZ); Vitaly Kapelevich, Auckland (NZ); David Monroy Felix, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 336 days.

(21) Appl. No.: 16/956,471

(22) PCT Filed: Dec. 20, 2018

(86) PCT No.: PCT/IB2018/060394
§ 371 (c)(1),
(2) Date: Jun. 19, 2020

(87) PCT Pub. No.: WO2019/123348
PCT Pub. Date: Jun. 27, 2019

(65) Prior Publication Data
US 2020/0338294 A1    Oct. 29, 2020

Related U.S. Application Data

(60) Provisional application No. 62/609,162, filed on Dec. 21, 2017.

(51) Int. Cl.
*A61M 16/06* (2006.01)
*A61M 16/08* (2006.01)
(Continued)

(52) U.S. Cl.
CPC .... *A61M 16/0683* (2013.01); *A61M 16/0616* (2014.02); *A61M 16/0816* (2013.01);
(Continued)

(58) Field of Classification Search
CPC .............. A61M 16/0683; A61M 16/06; A61M 16/0605; A61M 16/0633; A61M 16/0638;
(Continued)

(56) References Cited

U.S. PATENT DOCUMENTS

| 301,111 A | 7/1884 | Genese |
| 472,238 A | 4/1892 | Van Orden |

(Continued)

FOREIGN PATENT DOCUMENTS

| CA | 996301 | 9/1976 |
| CA | 1311662 | 12/1992 |

(Continued)

OTHER PUBLICATIONS cpap.com, InnoMed/Resp Care Bravo Nasal Pilow CPAP Mask with Headgear, (http://web.archive.org/web/*/https://www.cpap.com/productpage/bravo-nasal-interface/), downloaded Feb. 24, 2020, 5 pp.

(Continued)

*Primary Examiner* — Joseph D. Boecker
*Assistant Examiner* — Brian T Khong
(74) *Attorney, Agent, or Firm* — Knobbe, Martens, Olson & Bear, LLP

(57) ABSTRACT

A mask assembly includes a mask interface and a headgear assembly. The mask interface includes a housing and a seal that seals around a user's nose and/or mouth in use. The headgear assembly secures the mask interface to the user's face in use. The headgear assembly can include a top strap, a rear section, and side arms. The top strap can be manually adjustable. The rear section can be temporarily expanded to (Continued)

allow for donning and/or doffing of the mask assembly. The side arms can be automatically adjustable.

18 Claims, 45 Drawing Sheets

(51) Int. Cl.
    *A62B 9/04*           (2006.01)
    *A62B 18/02*         (2006.01)
    *A62B 18/08*         (2006.01)

(52) U.S. Cl.
    CPC .............. *A62B 9/04* (2013.01); *A62B 18/025* (2013.01); *A62B 18/084* (2013.01); *A61M 16/0622* (2014.02); *A61M 2205/0216* (2013.01); *A61M 2205/0272* (2013.01); *A61M 2210/0618* (2013.01); *A61M 2210/0625* (2013.01)

(58) Field of Classification Search
    CPC ............ A61M 16/0644; A61M 16/065; A61M 16/0655; A61M 16/0694; A61M 16/0611; A61M 16/0616; A61M 16/0816; A61M 16/0622; A62B 9/04; A62B 18/025; A62B 18/084
    See application file for complete search history.

(56) References Cited

U.S. PATENT DOCUMENTS

| | | |
|---|---|---|
| 577,926 A | 3/1897 | Miller |
| 718,470 A | 1/1903 | Jones |
| 751,091 A | 2/1904 | Moran |
| 770,013 A | 9/1904 | Linn |
| 1,364,104 A | 1/1921 | Geer |
| 1,635,545 A | 7/1927 | Drager |
| 1,942,442 A | 1/1934 | Motsinger |
| 2,199,690 A | 5/1940 | Bullard |
| 2,296,150 A | 9/1942 | Dockson et al. |
| 2,353,643 A | 7/1944 | Bulbulian |
| 2,359,506 A | 10/1944 | Battley et al. |
| 2,388,604 A | 11/1945 | Eisenbud |
| 2,390,233 A | 12/1945 | Akerman et al. |
| 2,508,050 A | 5/1950 | Valente |
| 2,586,851 A | 2/1952 | Monro et al. |
| 2,611,897 A | 9/1952 | Adams |
| 2,661,514 A | 12/1953 | Ada |
| 2,693,800 A | 11/1954 | Caldwell |
| 2,738,788 A | 3/1956 | Matheson et al. |
| 2,843,121 A | 7/1958 | Hudson |
| 2,859,748 A | 11/1958 | Hudson |
| 3,045,672 A | 7/1962 | Croasdaile |
| 3,156,922 A | 11/1964 | Anderson |
| 3,295,529 A | 1/1967 | Corrigall et al. |
| 3,416,521 A | 12/1968 | Humphrey |
| 3,457,564 A | 7/1969 | Holloway |
| 3,490,452 A | 1/1970 | Greenfield |
| 3,500,474 A | 3/1970 | Austin |
| 3,530,031 A | 9/1970 | Loew |
| 3,792,702 A | 2/1974 | Delest |
| 3,834,682 A | 9/1974 | McPhee |
| 3,850,171 A | 11/1974 | Ball et al. |
| 3,887,968 A | 6/1975 | Lynam |
| 3,972,321 A | 8/1976 | Proctor |
| 3,990,757 A | 11/1976 | Gill |
| 3,992,720 A | 11/1976 | Nicolinas |
| 3,994,022 A | 11/1976 | Villari et al. |
| 4,051,556 A | 10/1977 | Davenport et al. |
| 4,062,068 A | 12/1977 | Davenport et al. |
| 4,090,510 A | 5/1978 | Segersten |
| 4,106,165 A | 8/1978 | Clowers et al. |
| D250,047 S | 10/1978 | Lewis et al. |
| D250,131 S | 10/1978 | Lewis et al. |
| 4,127,130 A | 11/1978 | Naysmith |
| D252,322 S | 7/1979 | Johnson |
| 4,167,185 A | 9/1979 | Lewis |
| 4,201,205 A | 5/1980 | Bartholomew |
| 4,266,540 A | 5/1981 | Panzik et al. |
| 4,278,082 A | 7/1981 | Blackmer |
| 4,288,891 A | 9/1981 | Boden |
| 4,313,437 A | 2/1982 | Martin |
| 4,328,605 A | 5/1982 | Hutchison et al. |
| 4,354,488 A | 10/1982 | Bartos |
| 4,367,735 A | 1/1983 | Dali |
| 4,402,316 A | 9/1983 | Gadberry |
| 4,413,382 A | 11/1983 | Siegmann |
| 4,437,462 A | 3/1984 | Piljay |
| 4,453,292 A | 6/1984 | Bakker |
| 4,458,373 A | 7/1984 | Maslow |
| 4,477,928 A | 10/1984 | Graff |
| 4,606,077 A | 8/1986 | Phillips |
| D293,613 S | 1/1988 | Wingler |
| 4,734,940 A | 4/1988 | Galet et al. |
| 4,753,233 A | 6/1988 | Grimes |
| 4,782,832 A | 11/1988 | Trimble et al. |
| 4,817,596 A | 4/1989 | Gallet |
| 4,848,334 A | 7/1989 | Bellm |
| 4,853,275 A | 8/1989 | Tracy et al. |
| 4,856,508 A | 8/1989 | Tayebi |
| 4,915,105 A | 4/1990 | Lee |
| 4,941,467 A | 7/1990 | Takata |
| 4,944,310 A | 7/1990 | Sullivan |
| 4,947,488 A | 8/1990 | Ashnioff |
| D310,431 S | 9/1990 | Bellm |
| 4,971,051 A | 11/1990 | Toffolon |
| 4,986,269 A | 1/1991 | Hakkinen |
| 5,010,925 A | 4/1991 | Atkinson et al. |
| 5,016,625 A | 5/1991 | Hsu et al. |
| 5,042,478 A | 8/1991 | Kopala et al. |
| D320,677 S | 10/1991 | Kumagai et al. |
| 5,052,084 A | 10/1991 | Braun |
| D321,419 S | 11/1991 | Wallace |
| 5,065,756 A | 11/1991 | Rapoport |
| 5,074,297 A | 12/1991 | Venegas |
| 5,094,236 A | 3/1992 | Tayebi |
| 5,113,857 A | 5/1992 | Dickerman et al. |
| 5,148,578 A | 9/1992 | Clarke et al. |
| 5,148,802 A | 9/1992 | Sanders et al. |
| 5,191,882 A | 3/1993 | Vogliano |
| 5,231,979 A | 8/1993 | Rose |
| 5,245,995 A | 9/1993 | Sullivan et al. |
| D340,317 S | 10/1993 | Cole |
| 5,269,296 A | 12/1993 | Landis et al. |
| D354,128 S | 1/1995 | Rinehart |
| D355,484 S | 2/1995 | Rinehart |
| 5,388,743 A | 2/1995 | Silagy |
| 5,438,979 A | 8/1995 | Johnson et al. |
| 5,477,852 A | 12/1995 | Landis et al. |
| 5,488,948 A | 2/1996 | Dubruille |
| 5,513,634 A | 5/1996 | Jackson |
| 5,529,062 A | 6/1996 | Byrd |
| 5,533,506 A | 7/1996 | Wood |
| 5,546,605 A | 8/1996 | Mallardi |
| 5,551,419 A | 9/1996 | Froehlich et al. |
| 5,566,395 A | 10/1996 | Nebeker |
| 5,595,174 A | 1/1997 | Gwaltney |
| 5,601,078 A | 2/1997 | Schaller et al. |
| D378,610 S | 3/1997 | Reischel et al. |
| 5,657,752 A | 8/1997 | Landis et al. |
| 5,724,965 A | 3/1998 | Handke et al. |
| 5,752,510 A | 5/1998 | Goldstein |
| 5,755,578 A | 5/1998 | Contant et al. |
| 5,774,901 A | 7/1998 | Minami |
| 5,823,020 A | 10/1998 | Benda |
| 5,884,624 A | 3/1999 | Barnett et al. |
| 5,921,239 A | 7/1999 | McCall et al. |
| 5,941,245 A | 8/1999 | Hannah et al. |
| 5,941,856 A | 8/1999 | Kovacs et al. |
| 6,017,315 A | 1/2000 | Starr et al. |
| 6,019,101 A | 2/2000 | Cotner et al. |
| 6,044,844 A | 4/2000 | Kwok et al. |
| 6,050,260 A | 4/2000 | Daniell et al. |

(56) References Cited

U.S. PATENT DOCUMENTS

| | | |
|---|---|---|
| 6,119,694 A | 9/2000 | Correa et al. |
| 6,192,886 B1 | 2/2001 | Rudolph |
| D440,302 S | 4/2001 | Wolfe |
| 6,256,798 B1 | 7/2001 | Egolf et al. |
| 6,272,690 B1 | 8/2001 | Carey et al. |
| 6,282,725 B1 | 9/2001 | Vanidestine, Jr. |
| 6,298,850 B1 | 10/2001 | Argraves |
| 6,338,342 B1 | 1/2002 | Fecteau et al. |
| 6,347,631 B1 | 2/2002 | Hansen et al. |
| D455,891 S | 4/2002 | Biedrzycki |
| 6,418,928 B1 | 7/2002 | Bordewick et al. |
| 6,422,238 B1 | 7/2002 | Lithgow |
| 6,431,172 B1 | 8/2002 | Bordewick |
| 6,435,181 B1 | 8/2002 | Jones, Jr. et al. |
| 6,439,234 B1 | 8/2002 | Curti et al. |
| 6,470,886 B1 | 10/2002 | Jestrabek-Hart |
| 6,478,026 B1 | 11/2002 | Wood |
| 6,491,034 B1 | 12/2002 | Gunaratnam et al. |
| 6,536,435 B1 | 3/2003 | Fecteau et al. |
| 6,561,188 B1 | 5/2003 | Ellis |
| 6,561,191 B1 | 5/2003 | Kwok |
| 6,571,854 B1 | 6/2003 | Palmer |
| 6,581,594 B1 | 6/2003 | Drew et al. |
| 6,581,601 B2 | 6/2003 | Ziaee |
| 6,588,424 B2 | 7/2003 | Bardel |
| 6,631,718 B1 | 10/2003 | Lovell |
| 6,637,434 B2 | 10/2003 | Noble |
| 6,644,315 B2 | 11/2003 | Ziaee |
| 6,651,658 B1 | 11/2003 | Hill et al. |
| 6,659,102 B1 | 12/2003 | Sico |
| 6,662,803 B2 | 12/2003 | Gradon et al. |
| 6,679,257 B1 | 1/2004 | Robertson et al. |
| 6,679,265 B2 | 1/2004 | Strickland et al. |
| 6,772,761 B1 | 8/2004 | Rucker, Jr. |
| 6,851,425 B2 | 2/2005 | Jaffre et al. |
| 6,883,519 B2 | 4/2005 | Schmidtke et al. |
| 6,886,564 B2 | 5/2005 | Sullivan et al. |
| 6,892,729 B2 | 5/2005 | Smith et al. |
| 6,907,882 B2 | 6/2005 | Ging et al. |
| 6,951,218 B2 | 10/2005 | Gradon et al. |
| 7,004,165 B1 | 2/2006 | Salcido |
| D520,140 S | 5/2006 | Chaggares |
| 7,036,508 B2 | 5/2006 | Kwok |
| 7,062,795 B2 | 6/2006 | Skiba et al. |
| 7,066,179 B2 | 6/2006 | Eaton et al. |
| D526,094 S | 8/2006 | Chen |
| 7,096,864 B1 | 8/2006 | Mayer et al. |
| 7,096,867 B2 | 8/2006 | Smith et al. |
| 7,201,169 B2 | 4/2007 | Wilkie et al. |
| 7,207,333 B2 | 4/2007 | Tohara |
| 7,210,481 B1 | 5/2007 | Lovell et al. |
| 7,219,669 B1 | 5/2007 | Lovell et al. |
| 7,225,811 B2 | 6/2007 | Ruiz et al. |
| 7,318,437 B2 | 1/2008 | Gunaratnam et al. |
| 7,353,826 B2 | 4/2008 | Sleeper et al. |
| 7,353,827 B2 | 4/2008 | Geist |
| 7,814,911 B2 | 10/2010 | Bordewick et al. |
| 7,845,352 B2 | 12/2010 | Sleeper et al. |
| 7,861,715 B2 | 1/2011 | Jones et al. |
| 7,870,860 B2 | 1/2011 | McCormick et al. |
| 7,896,003 B2 | 3/2011 | Matula et al. |
| 7,913,692 B2 | 3/2011 | Kwok |
| 7,967,014 B2 | 6/2011 | Heidmann |
| 8,042,539 B2 | 10/2011 | Chandran et al. |
| 8,047,893 B2 | 11/2011 | Fenske |
| 8,074,651 B2 | 12/2011 | Bierman et al. |
| 8,104,473 B2 | 1/2012 | Woodard et al. |
| 8,132,270 B2 | 3/2012 | Lang et al. |
| 8,136,524 B2 | 3/2012 | Ging et al. |
| 8,209,995 B2 | 7/2012 | Kieling et al. |
| 8,297,285 B2 | 10/2012 | Henry et al. |
| 8,371,302 B2 | 2/2013 | Ging et al. |
| 8,443,807 B2 | 5/2013 | McAuley et al. |
| D686,313 S | 7/2013 | Matula et al. |
| 8,479,741 B2 | 7/2013 | McAuley et al. |
| 8,505,538 B2 | 8/2013 | Amarasinghe |
| 8,522,785 B2 | 9/2013 | Berthon-Jones et al. |
| 8,573,201 B2 | 11/2013 | Rummery et al. |
| 8,596,271 B2 | 12/2013 | Matula, Jr. et al. |
| 8,596,274 B2 | 12/2013 | Hieber et al. |
| 8,631,793 B2 | 1/2014 | Omura et al. |
| 8,636,005 B2 | 1/2014 | Gradon et al. |
| 8,636,007 B2 | 1/2014 | Rummery et al. |
| 8,636,008 B2 | 1/2014 | Flory et al. |
| 8,757,157 B2 | 6/2014 | Price et al. |
| 8,783,257 B2 | 7/2014 | McAuley et al. |
| 8,794,239 B2 | 8/2014 | Gunaratnam |
| 8,857,435 B2 | 10/2014 | Matula, Jr. et al. |
| 8,915,251 B2 | 12/2014 | Lubke et al. |
| 8,997,742 B2 | 4/2015 | Moore et al. |
| 9,032,955 B2 | 5/2015 | Lubke et al. |
| 9,044,564 B2 | 6/2015 | Dravitzki et al. |
| 9,103,161 B2 | 8/2015 | Mader |
| 9,138,555 B2 | 9/2015 | McAuley et al. |
| 9,149,596 B2 | 10/2015 | Valcic et al. |
| 9,265,909 B2 | 2/2016 | Ho et al. |
| 9,302,065 B2 | 4/2016 | Smith et al. |
| 9,320,866 B2 | 4/2016 | McAuley et al. |
| 9,333,315 B2 | 5/2016 | McAuley et al. |
| 9,339,622 B2 | 5/2016 | McAuley et al. |
| 9,480,809 B2 | 11/2016 | Guney et al. |
| 9,517,320 B2 | 12/2016 | Barlow et al. |
| 9,550,038 B2 | 1/2017 | McAuley et al. |
| 9,555,943 B2 | 1/2017 | Breen, IV et al. |
| 9,592,336 B2 | 3/2017 | Nielsen et al. |
| 9,656,038 B2 | 5/2017 | Rummery et al. |
| 9,744,385 B2 | 8/2017 | Henry |
| 9,782,554 B2 | 10/2017 | Mazzone et al. |
| 9,878,118 B2 | 1/2018 | Formica |
| D810,277 S | 2/2018 | Amarasinghe |
| 9,884,160 B2 | 2/2018 | Mcauley |
| 9,901,700 B2 | 2/2018 | McAuley et al. |
| 9,925,349 B2 | 3/2018 | Jablonski |
| 9,974,914 B2 | 5/2018 | McAuley |
| 9,993,606 B2 | 6/2018 | Gibson et al. |
| 10,039,665 B2 | 8/2018 | Blaszczykiewicz et al. |
| 10,065,010 B2 | 9/2018 | Smith et al. |
| 10,071,217 B2 | 9/2018 | Grashow |
| 10,080,856 B2 | 9/2018 | McLaren |
| 10,137,319 B2 | 11/2018 | Carr et al. |
| 10,207,072 B2 | 2/2019 | Dunn et al. |
| 10,279,138 B2 | 5/2019 | Ovzinsky |
| 10,456,546 B2 | 10/2019 | McLaren et al. |
| 10,646,680 B2 | 5/2020 | Huddart et al. |
| 10,675,428 B2 | 6/2020 | Guney et al. |
| 10,792,451 B2 | 10/2020 | Allan et al. |
| 10,828,449 B2 | 11/2020 | Higgins et al. |
| 10,828,452 B2 | 11/2020 | Huddart et al. |
| 10,874,814 B2 | 12/2020 | Huddart et al. |
| 11,419,999 B2 | 8/2022 | Patel et al. |
| 11,701,486 B2 | 7/2023 | Mashal et al. |
| 11,850,365 B2 | 12/2023 | Freestone et al. |
| 2002/0005198 A1 | 1/2002 | Kwok et al. |
| 2002/0020416 A1 | 2/2002 | Namey |
| 2002/0046755 A1 | 4/2002 | Voss |
| 2002/0052568 A1 | 5/2002 | Houser et al. |
| 2002/0053347 A1 | 5/2002 | Ziaee |
| 2002/0059935 A1 | 5/2002 | Wood |
| 2002/0096178 A1 | 7/2002 | Ziaee |
| 2002/0157668 A1 | 10/2002 | Bardel |
| 2003/0005933 A1 | 1/2003 | Izuchukwu |
| 2003/0051732 A1 | 3/2003 | Smith et al. |
| 2003/0079749 A1 | 5/2003 | Strickland et al. |
| 2003/0084903 A1 | 5/2003 | Fecteau et al. |
| 2003/0111080 A1 | 6/2003 | Olsen et al. |
| 2003/0121519 A1 | 7/2003 | Estes et al. |
| 2003/0164170 A1 | 9/2003 | Drew et al. |
| 2003/0172936 A1 | 9/2003 | Wilkie et al. |
| 2003/0196656 A1 | 10/2003 | Moore |
| 2003/0196659 A1 | 10/2003 | Gradon et al. |
| 2003/0196664 A1 | 10/2003 | Jacobson |
| 2003/0200970 A1 | 10/2003 | Stenzler et al. |
| 2004/0025883 A1* | 2/2004 | Eaton ............... A61M 16/0683 128/207.11 |

(56) References Cited

U.S. PATENT DOCUMENTS

| | | |
|---|---|---|
| 2004/0067333 A1 | 4/2004 | Amarasinghe |
| 2004/0211427 A1 | 10/2004 | Jones et al. |
| 2004/0226566 A1 | 11/2004 | Gunaratnam et al. |
| 2005/0011524 A1 | 1/2005 | Thomlinson et al. |
| 2005/0016067 A1 | 1/2005 | Pettit |
| 2005/0028822 A1 | 2/2005 | Sleeper et al. |
| 2005/0033247 A1 | 2/2005 | Thompson |
| 2005/0066976 A1 | 3/2005 | Wondka |
| 2005/0076913 A1 | 4/2005 | Ho et al. |
| 2005/0098183 A1 | 5/2005 | Nash et al. |
| 2005/0150497 A1 | 7/2005 | Eifler et al. |
| 2005/0155604 A1* | 7/2005 | Ging ............... A61M 16/0616 128/207.11 |
| 2005/0161049 A1 | 7/2005 | Wright |
| 2005/0199239 A1 | 9/2005 | Lang et al. |
| 2005/0199242 A1 | 9/2005 | Matula et al. |
| 2005/0205096 A1 | 9/2005 | Matula |
| 2005/0235999 A1 | 10/2005 | Wood et al. |
| 2006/0060200 A1 | 3/2006 | Ho et al. |
| 2006/0081250 A1 | 4/2006 | Bordewick et al. |
| 2006/0096596 A1 | 5/2006 | Occhialini et al. |
| 2006/0107958 A1 | 5/2006 | Sleeper |
| 2006/0113147 A1 | 6/2006 | Harris |
| 2006/0118117 A1 | 6/2006 | Berthon-Jones et al. |
| 2006/0124131 A1 | 6/2006 | Chandran |
| 2006/0137690 A1 | 6/2006 | Gunaratnam et al. |
| 2006/0174887 A1 | 8/2006 | Chandran et al. |
| 2006/0174892 A1 | 8/2006 | Leksutin et al. |
| 2006/0196510 A1 | 9/2006 | McDonald et al. |
| 2006/0196511 A1 | 9/2006 | Lau et al. |
| 2006/0237018 A1 | 10/2006 | McAuley et al. |
| 2007/0000492 A1 | 1/2007 | Hansel et al. |
| 2007/0010786 A1 | 1/2007 | Casey et al. |
| 2007/0089749 A1 | 4/2007 | Ho et al. |
| 2007/0125385 A1 | 6/2007 | Ho et al. |
| 2007/0125387 A1 | 6/2007 | Zollinger et al. |
| 2007/0130663 A1 | 6/2007 | Lang et al. |
| 2007/0137653 A1 | 6/2007 | Wood |
| 2007/0163600 A1 | 7/2007 | Hoffman |
| 2007/0169777 A1 | 7/2007 | Amarasinghe et al. |
| 2007/0175480 A1 | 8/2007 | Gradon et al. |
| 2007/0209663 A1 | 9/2007 | Marque et al. |
| 2007/0215161 A1 | 9/2007 | Frater et al. |
| 2007/0235033 A1 | 10/2007 | Reler et al. |
| 2007/0295335 A1 | 12/2007 | Nashed |
| 2008/0041388 A1 | 2/2008 | McAuley et al. |
| 2008/0041393 A1 | 2/2008 | Bracken |
| 2008/0047560 A1 | 2/2008 | Veliss et al. |
| 2008/0052806 A1 | 3/2008 | McDaniel |
| 2008/0053450 A1 | 3/2008 | Van Kerkwyk et al. |
| 2008/0060648 A1 | 3/2008 | Thornton et al. |
| 2008/0060653 A1 | 3/2008 | Hallet et al. |
| 2008/0060657 A1 | 3/2008 | McAuley et al. |
| 2008/0065015 A1 | 3/2008 | Fiser |
| 2008/0083412 A1 | 4/2008 | Henry et al. |
| 2008/0092906 A1 | 4/2008 | Gunaratnam et al. |
| 2008/0099024 A1 | 5/2008 | Gunaratnam et al. |
| 2008/0110464 A1 | 5/2008 | Davidson et al. |
| 2008/0134480 A1 | 6/2008 | Shiue |
| 2008/0196728 A1 | 8/2008 | Ho |
| 2008/0230068 A1 | 9/2008 | Rudolph |
| 2008/0230069 A1 | 9/2008 | Valcic et al. |
| 2008/0264422 A1 | 10/2008 | Fishman |
| 2008/0302366 A1 | 12/2008 | McGinnis et al. |
| 2008/0314388 A1 | 12/2008 | Brambilla et al. |
| 2009/0000624 A1 | 1/2009 | Lee et al. |
| 2009/0014007 A1 | 1/2009 | Brambilla et al. |
| 2009/0032026 A1 | 2/2009 | Price et al. |
| 2009/0044808 A1 | 2/2009 | Guney et al. |
| 2009/0044809 A1 | 2/2009 | Welchel et al. |
| 2009/0120442 A1 | 5/2009 | Ho |
| 2009/0133697 A1 | 5/2009 | Kwok et al. |
| 2009/0145429 A1 | 6/2009 | Ging et al. |
| 2009/0173349 A1 | 7/2009 | Hernandez et al. |
| 2009/0178680 A1 | 7/2009 | Chang |
| 2009/0183739 A1 | 7/2009 | Wondka |
| 2009/0211583 A1 | 8/2009 | Carroll |
| 2009/0250060 A1 | 10/2009 | Hacke et al. |
| 2009/0320187 A1 | 12/2009 | Petzl et al. |
| 2010/0000538 A1 | 1/2010 | Edwards et al. |
| 2010/0000544 A1 | 1/2010 | Blaszczykiewicz et al. |
| 2010/0018534 A1 | 1/2010 | Veliss et al. |
| 2010/0037897 A1 | 2/2010 | Wood |
| 2010/0154798 A1 | 6/2010 | Henry et al. |
| 2010/0224199 A1 | 9/2010 | Smith et al. |
| 2010/0258132 A1 | 10/2010 | Moore |
| 2010/0258136 A1 | 10/2010 | Doherty et al. |
| 2010/0282265 A1 | 11/2010 | Melidis et al. |
| 2010/0307502 A1 | 12/2010 | Rummery et al. |
| 2010/0313532 A1 | 12/2010 | Stjernfelt et al. |
| 2010/0313891 A1 | 12/2010 | Veliss et al. |
| 2010/0319700 A1* | 12/2010 | Ng ................. A61M 16/0858 128/206.28 |
| 2011/0048425 A1 | 3/2011 | Chang |
| 2011/0197341 A1 | 8/2011 | Formica |
| 2011/0220113 A1 | 9/2011 | Newman |
| 2011/0247628 A1 | 10/2011 | Ho |
| 2011/0259335 A1 | 10/2011 | Sullivan |
| 2011/0265791 A1 | 11/2011 | Ging et al. |
| 2011/0265796 A1 | 11/2011 | Amarasinghe et al. |
| 2012/0067349 A1 | 3/2012 | Barlow et al. |
| 2012/0125339 A1 | 5/2012 | Ho et al. |
| 2012/0132209 A1 | 5/2012 | Rummery |
| 2012/0138063 A1 | 6/2012 | Eves et al. |
| 2012/0174355 A1 | 7/2012 | Fraze |
| 2012/0222680 A1 | 9/2012 | Eves et al. |
| 2012/0285464 A1 | 11/2012 | Birch et al. |
| 2012/0304999 A1 | 12/2012 | Swift et al. |
| 2013/0000648 A1 | 1/2013 | Madaus et al. |
| 2013/0139822 A1 | 6/2013 | Gibson |
| 2013/0152918 A1 | 6/2013 | Rummery et al. |
| 2013/0152937 A1 | 6/2013 | Jablonski |
| 2013/0160769 A1 | 6/2013 | Ng et al. |
| 2013/0220327 A1 | 8/2013 | Barlow et al. |
| 2013/0247916 A1 | 9/2013 | Symons |
| 2013/0319421 A1 | 12/2013 | Hitchcock et al. |
| 2014/0026888 A1 | 1/2014 | Matula |
| 2014/0026890 A1 | 1/2014 | Haskard et al. |
| 2014/0083428 A1 | 3/2014 | Rothermel et al. |
| 2014/0102456 A1 | 4/2014 | Ovizinsky |
| 2014/0137870 A1 | 5/2014 | Barlow |
| 2014/0158726 A1 | 6/2014 | Malara |
| 2014/0166019 A1 | 6/2014 | Ho et al. |
| 2014/0190486 A1 | 7/2014 | Dunn et al. |
| 2014/0209098 A1 | 7/2014 | Dunn |
| 2014/0216452 A1 | 8/2014 | Miller et al. |
| 2014/0305439 A1 | 10/2014 | Chodkowski |
| 2014/0358054 A1 | 12/2014 | Capra |
| 2015/0000615 A1 | 1/2015 | Imran et al. |
| 2015/0005685 A1 | 1/2015 | Chetlapalli et al. |
| 2015/0028519 A1 | 1/2015 | Lang et al. |
| 2015/0033457 A1 | 2/2015 | Tryner et al. |
| 2015/0051000 A1 | 2/2015 | Henn |
| 2015/0090268 A1 | 4/2015 | Madaus et al. |
| 2015/0128953 A1 | 5/2015 | Formica et al. |
| 2015/0151070 A1 | 6/2015 | Capra et al. |
| 2015/0190262 A1 | 7/2015 | Capra et al. |
| 2015/0202397 A1 | 7/2015 | Pastoor |
| 2015/0217150 A1 | 8/2015 | Harris |
| 2015/0285337 A1 | 10/2015 | Dingley et al. |
| 2015/0290415 A1 | 10/2015 | Dunn |
| 2016/0022944 A1 | 1/2016 | Chodkowski et al. |
| 2016/0038707 A1 | 2/2016 | Allan et al. |
| 2016/0045700 A1 | 2/2016 | Amarasinghe |
| 2016/0082214 A1 | 3/2016 | Barlow et al. |
| 2016/0144146 A1* | 5/2016 | Huddart ............ A61M 16/0816 128/206.21 |
| 2016/0166793 A1 | 6/2016 | McLaren et al. |
| 2016/0178027 A1 | 6/2016 | Wetzel |
| 2016/0278463 A1 | 9/2016 | Stevenson |
| 2016/0375214 A1 | 12/2016 | Chodkowski et al. |
| 2017/0136269 A1 | 5/2017 | Jacotey et al. |
| 2017/0182276 A1 | 6/2017 | Hammer |
| 2017/0189636 A1 | 7/2017 | Gibson et al. |

(56) References Cited

U.S. PATENT DOCUMENTS

| | | |
|---|---|---|
| 2017/0216548 A1 | 8/2017 | Gerhardt |
| 2017/0274167 A1* | 9/2017 | Huddart ............ A61M 16/0825 |
| 2018/0214655 A1 | 8/2018 | Kooij et al. |
| 2018/0264218 A1 | 9/2018 | Chodkowski |
| 2018/0339123 A1 | 11/2018 | Smith et al. |
| 2019/0083734 A1 | 3/2019 | Hammer et al. |
| 2019/0111227 A1 | 4/2019 | Veliss et al. |
| 2019/0117026 A1 | 4/2019 | Felix et al. |
| 2019/0151592 A1 | 5/2019 | Bornholdt |
| 2020/0129720 A1 | 4/2020 | McLaren et al. |
| 2020/0171260 A1 | 6/2020 | McLaren et al. |
| 2020/0230343 A1 | 7/2020 | Sims et al. |
| 2020/0230344 A1 | 7/2020 | Huddart et al. |
| 2021/0008316 A1 | 1/2021 | McLaren et al. |
| 2021/0016041 A1 | 1/2021 | Huddart et al. |
| 2022/0126049 A1 | 4/2022 | Amarasinghe |
| 2022/0331542 A1 | 10/2022 | McLaren et al. |
| 2023/0201510 A1 | 6/2023 | Hammer |
| 2023/0347090 A1 | 11/2023 | Huddart et al. |

FOREIGN PATENT DOCUMENTS

| | | |
|---|---|---|
| CN | 2172538 | 7/1994 |
| CN | 2504493 Y | 8/2002 |
| CN | 2562067 Y | 7/2003 |
| CN | 1784250 | 6/2006 |
| CN | 1901963 A | 1/2007 |
| CN | 201033204 | 3/2008 |
| CN | 201171846 | 12/2008 |
| CN | 101432039 A | 5/2009 |
| CN | 100502972 C | 6/2009 |
| CN | 101516427 | 8/2009 |
| CN | 202822396 U | 3/2013 |
| CN | 103536996 | 1/2014 |
| DE | 895692 | 11/1953 |
| DE | 2706284 | 8/1978 |
| DE | 3122034 | 12/1982 |
| DE | 3907428 | 9/1990 |
| DE | 10254399 | 6/2004 |
| DE | 102006011151 | 9/2007 |
| EP | 0 350 322 | 1/1990 |
| EP | 0 401 307 | 8/1995 |
| EP | 0 879 565 | 11/1998 |
| EP | 0 982 049 | 3/2000 |
| EP | 1 187 650 | 12/2005 |
| EP | 2 060 294 | 5/2009 |
| EP | 2 130 563 | 12/2009 |
| EP | 2 327 443 | 6/2011 |
| EP | 2 517 757 | 10/2012 |
| EP | 2 022 528 | 3/2016 |
| FR | 2390116 | 3/1938 |
| FR | 2618340 | 11/1970 |
| FR | 825960 | 1/1989 |
| FR | 2658725 | 8/1991 |
| FR | 2749176 | 12/1997 |
| FR | 2804421 | 8/2001 |
| GB | 190224431 | 12/1902 |
| GB | 339522 | 12/1930 |
| GB | 826198 | 12/1959 |
| GB | 880824 | 10/1961 |
| GB | 1467828 | 3/1977 |
| GB | 2133275 | 7/1984 |
| GB | 2188236 | 9/1987 |
| GB | 1211268 | 4/2000 |
| GB | 2478305 | 9/2011 |
| GB | 2491227 | 11/2012 |
| GB | 2553475 | 3/2018 |
| JP | S46-12114 | 4/1971 |
| JP | 46-016719 | 6/1971 |
| JP | S55-89072 | 7/1980 |
| JP | 2004-016488 | 1/2004 |
| JP | 2003-053874 | 9/2004 |
| JP | 2009-125306 | 6/2009 |
| JP | 2010-090973 | 4/2010 |
| JP | 2000-102624 | 5/2013 |
| JP | 2018-127729 | 8/2018 |
| KR | 10-2011-0028950 | 3/2011 |
| NZ | 585295 | 12/2011 |
| WO | WO 95/12432 | 5/1995 |
| WO | WO 97/32494 | 9/1997 |
| WO | WO 98/003225 | 1/1998 |
| WO | WO 98/018514 | 5/1998 |
| WO | WO 99/04842 | 2/1999 |
| WO | WO 99/058181 | 11/1999 |
| WO | WO 00/50122 | 8/2000 |
| WO | WO 00/069497 | 11/2000 |
| WO | WO 00/074758 | 12/2000 |
| WO | WO 01/041854 | 6/2001 |
| WO | WO 01/097892 | 12/2001 |
| WO | WO 02/44749 | 6/2002 |
| WO | WO 02/047749 | 6/2002 |
| WO | WO 02/074372 | 9/2002 |
| WO | WO 04/039185 | 5/2004 |
| WO | WO 04/041341 | 5/2004 |
| WO | WO 04/073778 | 9/2004 |
| WO | WO 05/021075 | 3/2005 |
| WO | WO 05/032634 | 4/2005 |
| WO | WO 05/046776 | 5/2005 |
| WO | WO 05/051468 | 6/2005 |
| WO | WO 05/063328 | 7/2005 |
| WO | WO 05/118042 | 12/2005 |
| WO | WO 05/123166 | 12/2005 |
| WO | WO 06/130903 | 12/2006 |
| WO | WO 06/138416 | 12/2006 |
| WO | WO 07/022562 | 3/2007 |
| WO | WO 07/041786 | 4/2007 |
| WO | WO 07/068044 | 6/2007 |
| WO | WO 07/125487 | 11/2007 |
| WO | WO 07/147088 | 12/2007 |
| WO | WO 08/007985 | 1/2008 |
| WO | WO 08/060295 | 5/2008 |
| WO | WO 08/070929 | 6/2008 |
| WO | WO 08/106716 | 9/2008 |
| WO | WO 08/148086 | 12/2008 |
| WO | WO 09/026627 | 3/2009 |
| WO | WO 09/038918 | 3/2009 |
| WO | WO 09/052560 | 4/2009 |
| WO | WO 09/059353 | 5/2009 |
| WO | WO 09/092057 | 7/2009 |
| WO | WO 09/108994 | 9/2009 |
| WO | WO 09/108995 | 9/2009 |
| WO | WO 09/139647 | 11/2009 |
| WO | WO 09/148956 | 12/2009 |
| WO | WO 10/066004 | 6/2010 |
| WO | WO 10/081295 | 7/2010 |
| WO | WO 10/131189 | 11/2010 |
| WO | WO 10/139014 | 12/2010 |
| WO | WO 11/072739 | 6/2011 |
| WO | WO 11/077254 | 6/2011 |
| WO | WO 11/112401 | 9/2011 |
| WO | WO 12/07300 | 1/2012 |
| WO | WO 12/045127 | 4/2012 |
| WO | WO 12/069951 | 5/2012 |
| WO | WO 12/071300 | 5/2012 |
| WO | WO 12/143822 | 10/2012 |
| WO | WO 12/154883 | 11/2012 |
| WO | WO 12/177152 | 12/2012 |
| WO | WO 13/006913 | 1/2013 |
| WO | WO 13/026091 | 2/2013 |
| WO | WO 13/026092 | 2/2013 |
| WO | WO 13/064930 | 5/2013 |
| WO | WO 14/020469 | 2/2014 |
| WO | WO 14/025267 | 2/2014 |
| WO | WO 14/031673 | 2/2014 |
| WO | WO 14/075141 | 5/2014 |
| WO | WO 14/077708 | 5/2014 |
| WO | WO 14/110622 | 7/2014 |
| WO | WO 14/110626 | 7/2014 |
| WO | WO 14/129913 | 8/2014 |
| WO | WO 14/175753 | 10/2014 |
| WO | WO 2014/175752 | 10/2014 |
| WO | WO 15/033287 | 3/2015 |
| WO | WO 15/043229 | 4/2015 |
| WO | WO 15/070289 | 5/2015 |

(56) References Cited

FOREIGN PATENT DOCUMENTS

| WO | WO 15/079396 | 6/2015 |
|---|---|---|
| WO | WO 15/083060 | 6/2015 |
| WO | WO 15/151019 | 10/2015 |
| WO | WO 15/187986 | 12/2015 |
| WO | WO 16/043603 | 3/2016 |
| WO | WO 17/030447 | 2/2017 |
| WO | WO 17/150990 | 9/2017 |
| WO | WO 17/158544 | 9/2017 |
| WO | WO 17/160166 | 9/2017 |
| WO | WO 2017/158474 | 9/2017 |
| WO | WO 17/216708 | 12/2017 |
| WO | WO 2019/003094 | 1/2019 |

OTHER PUBLICATIONS

Pad A Cheek, LLC, Speel apnea can make beautiful sleep elusive, (http://web.archive.org/web/20070701000000*/http://www.padacheek.com/;Wayback Machine), downloaded Feb. 24, 2020, 3 pp.
Philips Respironics 'System One Heated Humidifier—User Manual', 2011, pp. 1-16, [retrieved on Nov. 25, 2013] from the internet: URL: http://www.cpapxchange.com/cpap-machines-biap-machines/system-one-60-series-cpap-humidifier-manual.pdf.
International Search Report and Written Opinion of PCT/IB2018/060394, dated Dec. 20, 2018 in 19 pages.

* cited by examiner

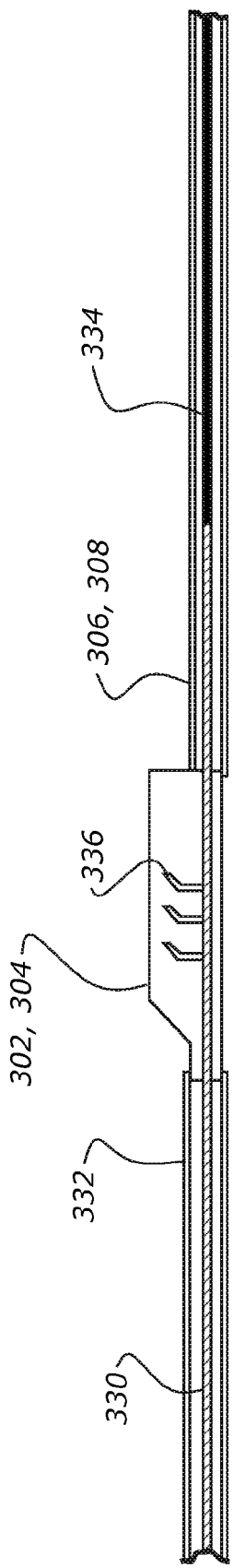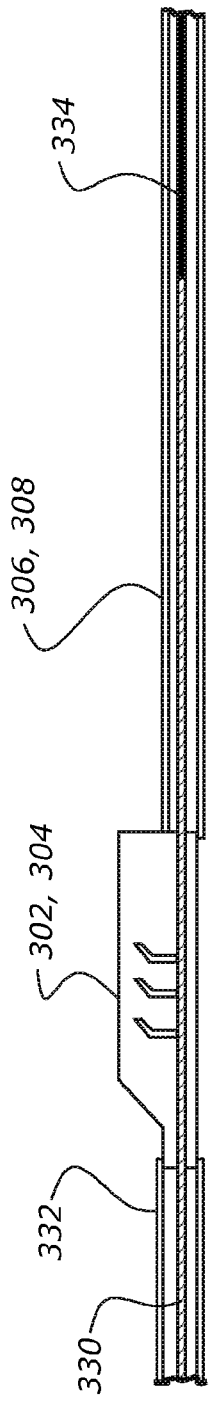

RESPIRATORY MASK SYSTEM

INCORPORATION BY REFERENCE TO ANY PRIORITY APPLICATIONS

Any and all applications for which a foreign or domestic priority claim is made in connection with the present application are hereby incorporated by reference and made a part of the disclosure.

BACKGROUND

Field

The present disclosure generally relates to a respiratory mask system for the delivery of respiratory therapy to a patient. More particularly, the present disclosure relates to various components of a respiratory mask system.

Description of the Related Art

Respiratory masks are used to provide respiratory therapy to the airways of a person suffering from any of a number of respiratory illnesses or conditions. Such therapies may include but are not limited to continuous positive airway pressure (CPAP) therapy and non-invasive ventilation (NIV) therapy.

CPAP therapy can be used to treat obstructive sleep apnea (OSA), a condition in which a patient's airway intermittently collapses, during sleep, preventing the patient from breathing for a period of time. The cessation of breathing, or apnea, results in the patient awakening. Repetitive and frequent apneas may result in the patient rarely achieving a full and restorative night's sleep.

CPAP therapy involves the delivery of a supply of continuous positive air pressure to the airway of the patient via a respiratory mask. The continuous positive pressure acts as a splint within the patient's airway, which secures the airway in an open position such that the patient's breathing and sleep are not interrupted.

Respiratory masks typically comprise a patient interface and a headgear, wherein the patient interface is configured to deliver the supply of continuous positive air pressure to the patient's airway via a seal or cushion that forms an airtight seal in or around the patient's nose and/or mouth. Respiratory masks are available in a range of styles including full-face, nasal, direct nasal and oral masks, which create an airtight seal with the nose and/or mouth. The seal or cushion is held in place on the patient's face by the headgear. In order to maintain an airtight seal the headgear should provide support to the patient interface such that it is held in a stable position relative to the patient's face during use. Such respiratory masks may also be used to deliver NIV and other therapies.

SUMMARY

In a first aspect the invention relates to a respiratory mask assembly comprising:
 a mask interface comprising a housing and a seal coupled to the housing, the seal configured to seal on a user's face in use; and
 a headgear assembly coupled to the mask interface at four locations and comprising at least two automatically adjusting headgear mechanisms, one of the at least two automatically adjusting headgear mechanisms disposed on each side of the user's face in use.

In another aspect the invention relates to a respiratory mask assembly comprising:
 a mask interface comprising a housing and a seal coupled to the housing, the seal configured to seal on a user's face in use; and
 a headgear assembly coupled to the mask interface and comprising:
  two upper automatically adjusting headgear mechanisms and two lower automatically adjusting headgear mechanisms, one of each of the upper and lower automatically adjusting headgear mechanisms disposed on each side of the user's face in use, wherein a connector housing a control mechanism of each of the lower automatically adjusting headgear mechanisms is configured to be located behind one of the user's ears in use;
  two upper side straps extending from the mask interface; and
  two lower side straps comprising an elastic portion and extending from the mask interface.

In another aspect the invention relates to a headgear assembly for a respiratory mask assembly, the headgear assembly comprising:
 two side straps, one of the two side straps disposed on each side of a user's face in use, each of the side straps comprising a single continuous strap having an upper portion and a lower portion, each upper portion connected to an upper section of the headgear assembly, and each lower portion connected to a lower section of the headgear assembly;
 a connector housing a control mechanism of an automatically adjusting headgear mechanism coupled to one end of each of the side straps; and
 a filament extending through at least a portion of each of the side straps.

In another aspect the invention relates to a respiratory mask assembly comprising:
 a headgear assembly comprising:
  an upper headgear loop;
  a lower headgear loop; and
  a side strap coupling the upper headgear loop and the lower headgear loop on each side of a user's face in use; and
 a mask interface coupled to the side straps, wherein a position of the mask interface along a length of the side straps is configured to be adjusted to adjust a length of the upper headgear loop relative to the lower headgear loop.

In some embodiments the mask interface is a full face mask and the seal is configured to cover the user's nose and mouth in use.

In some embodiments the respiratory mask assembly further comprises a removable frame.

In some embodiments the removable frame comprises two upper headgear connector arms and two lower headgear connector arms, wherein an upper side strap of a headgear can be coupled, permanently or removably, to each of the upper arms and a lower side strap of the headgear can be coupled, permanently or removably, to each of the lower arms.

In some embodiments the frame comprises a top edge and two opposing side edges, wherein the top edge and each of the side edges follow a continuous arc.

In some embodiments the frame is generally quadrilateral in shape and comprises a front surface and a rear surface, each having upper, lower and side edges, and the two lower headgear connector arms extend from the rear surface, at, adjacent or spaced from the lower edge of the front surface.

In some embodiments the frame comprises a gas path positioned within a space defined by a portion of the rear surface of the frame.

In some embodiments the frame and the gas path are integrated to form a single component.

In some embodiments the front surface is curved and is substantially smooth.

In some embodiments the frame comprises insert recesses, each insert recess housing one of the two automatically adjusting headgear mechanism and their associated components.

In some embodiments each insert recess is formed in the front surface of the frame.

In some embodiments each insert recess comprises a shelf portion, a mouth, a chamber and a channel that terminates at a blind end.

In some embodiments each insert recess extends along the side edge of the frame.

In some embodiments each insert recess houses a control mechanism and an associated filament of one automatically adjusting headgear mechanism.

The respiratory mask assembly of any one of claims 10 to 14, wherein an insert may be inserted into each insert recess.

In some embodiments the insert is inserted into the insert recess engaging at least the shelf and providing a cover that forms an enclosed space within the insert recess.

In some embodiments, in use, the filament can move longitudinally within the insert recess, with a free end of the filament able to move towards and away from the blind end of the insert recess, as dictated by the motion of the headgear and operation of the automatically adjusting headgear mechanism.

In some embodiments each insert comprises an alignment feature.

In some embodiments when the insert is engaged with the frame the alignment feature is positioned within the chamber and oriented to correctly orient the automatically adjusting headgear mechanism for operation.

In some embodiments connectors housing control mechanisms of the upper automatically adjusting headgear mechanisms are configured to be located above the user's ears in use.

In some embodiments control mechanisms of the upper automatically adjusting headgear mechanisms are disposed in a yoke, the yoke coupled to two upper side straps of the headgear assembly configured to be removably coupled to the housing in use.

In some embodiments the respiratory mask assembly further comprises at least one upper storage sleeve extending along a top strap of the headgear assembly configured to extend across a top of the user's head in use, the at least one upper storage sleeve configured to receive and store at least a portion of at least one filament of at least one of the two upper automatically adjusting headgear mechanisms.

In some embodiments the respiratory mask assembly further comprises at least one lower storage sleeve extending along a rear section of the headgear assembly configured to positioned on aback of the user's head in use, the at least one lower storage sleeve configured to receive and store at least a portion of at least one filament of at least one of the two lower automatically adjusting headgear mechanisms.

In some embodiments the headgear assembly further comprises a rear section, the rear section comprising a rigid upper section or strap and a temporarily expandable lower section.

In some embodiments the lower section comprises an elastic material.

In some embodiments the lower section comprises a first section comprising at least one magnet and a second section comprising at least one magnet, wherein the magnets of the first and second sections attract one another to connect the first and second sections in a closed position of the lower section, and wherein the first and second sections can be separated for donning and/or doffing of the mask assembly by applying a force greater than a magnetic force between the magnets.

In some embodiments the lower section comprises a foldable connection.

In some embodiments the lower section comprises a first rail and a second rail, the first and second rails configured to overlap and interlock with each other and slide relative to each other, wherein the first and second rails are configured to slide relative to each other to decrease an overlap between the first and second rails to temporarily lengthen the lower section.

In some embodiments the lower section comprises a first portion comprising a male connector and a second portion comprising a female connector configured to receive the male connector, and wherein the male connector is configured to be removed from the female connector to temporarily lengthen the lower section.

In some embodiments the upper section of the headgear assembly comprises a top strap configured to extend across a top of the user's head in use and an upper rear strap configured to extend across a back of the user's head in use.

In some embodiments the headgear assembly further comprises a storage sleeve extending along the top strap, the storage sleeve configured to receive and storage at least a portion of at least one of the filaments.

In some embodiments each connector is coupled to an end of the top strap and an end of the upper rear strap.

In some embodiments the lower section of the headgear assembly comprises an adjustable lower rear section configured to extend along a back of the user's neck in use.

In some embodiments each of the two side straps is coupled to one side of a mask interface of the mask assembly.

In some embodiments each of the two side straps extends through a passage formed on one side of a mask interface of the mask assembly.

In some embodiments each side strap is configured to slide within its respective passage to adjust relative lengths of the upper portion and the lower portion.

In some embodiments the headgear assembly further comprises a blocking element coupled to each of the side straps, each blocking element configured to limit sliding of the side strap within the passage to maintain a minimum length of the lower portion.

In some embodiments the blocking element does not limit movement of the filament within the side strap.

In some embodiments the headgear assembly comprises a top strap configured to extend across a top of the user's head in use, the top strap extending between and connecting opposing sides of the upper headgear loop.

In some embodiments the side straps are elastic.

In some embodiments each side strap forms a portion of the upper headgear loop and the lower headgear loop.

In some embodiments, a respiratory mask assembly includes a mask interface and a headgear assembly. The mask interface includes a housing and a seal coupled to the housing. The seal is configured to seal on a user's face in use. The headgear assembly is coupled to the mask interface at four locations. The headgear assembly includes at least two automatically adjusting headgear mechanisms, with one disposed on each side of the user's face in use. The mask interface can be a full face mask, with the seal configured to cover the user's nose and mouth in use.

In some embodiments, a respiratory mask assembly includes a mask interface and a headgear assembly. The mask interface includes a housing and a seal coupled to the housing. The seal is configured to seal on a user's face in use. The headgear assembly includes two upper automatically adjusting headgear mechanisms and two lower automatically adjusting mechanisms, with one of each of the upper and lower automatically adjusting headgear mechanisms disposed on each side of the user's face in use. A connector housing a control mechanism of each of the lower automatically adjusting headgear mechanisms can be configured to be located behind one of the user's ears in use. Two upper side straps extend from the mask interface. Two lower side straps include an elastic portion and extend from the mask interface.

Connectors housing control mechanisms of the upper automatically adjusting headgear mechanism can be configured to be located above the user's ears in use. Alternatively, control mechanisms of the upper automatically adjusting headgear mechanisms can be disposed in a yoke that is coupled to two upper side straps of the headgear assembly and configured to be removably coupled to the mask interface housing. The mask assembly can include at least one upper storage sleeve extending along a top strap of the headgear assembly configured to extend across a top of the user's head in use. The at least one upper storage sleeve is configured to receive and store at least a portion of at least one filament of at least one of the two upper automatically adjusting headgear mechanisms. The mask assembly can include at least one lower storage sleeve extending along a rear section of the headgear assembly so that at least a portion of the storage sleeve is positioned on a back of the user's head in use. The at least one lower storage sleeve can be configured to receive and store at least a portion of at least one filament of at least one of the two lower automatically adjusting headgear mechanisms.

The headgear assembly can further include a rear section comprising a rigid upper section and a temporarily expandable lower section. The rigid upper section may comprise a strap. The lower section can include an elastic material. The lower section can include a first section comprising at least one magnet and a second section comprising at least one magnet, wherein the magnets of the first and second sections attract one another to connect the first and second sections in a closed position of the lower section, and wherein the first and second sections can be separated for donning and/or doffing of the mask assembly by applying a force greater than a magnetic force between the magnets. The lower section can include a foldable connection. The lower section can include a first rail and a second rail, the first and second rails configured to overlap and interlock with each other and slide relative to each other, wherein the first and second rails are configured to slide relative to each other to decrease an overlap between the first and second rails to temporarily lengthen the lower section. The lower section can include a first portion including a male connector and a second portion including a female connector configured to receive the male connector. The male connector is configured to be removed from the female connector to temporarily lengthen the lower section.

In some embodiments, a headgear assembly for a respiratory mask assembly includes two side straps, a connector housing a control mechanism of an automatically adjusting headgear mechanism coupled to one end of each of the side straps, and a filament extending through at least a portion of each of the side straps. One of the two side straps is disposed on each side of a user's face in use. Each of the side straps includes a single continuous strap having an upper portion and a lower portion, each upper portion connected to an upper section of the headgear assembly and each lower portion connected to a lower section of the headgear assembly.

The upper section of the headgear assembly can include a top strap configured to extend across a top of the user's head in use and an upper rear strap configured to extend across a back of the user's head in use. The headgear assembly can include a storage sleeve extending along the top strap and configured to receive and store at least a portion of at least one of the filaments. Each connector can be coupled to an end of the top strap and an end of the upper rear strap. The lower section of the headgear assembly can include an adjustable lower rear section configured to extend along a back of the user's neck in use. Each of the two side straps can be coupled to one side of a mask interface of the mask assembly. Each of the two side straps can extend through a passage formed on one side of a mask interface of the mask assembly. Each side strap can be configured to slide within its respective passage to adjust relative lengths of the upper and lower portion. The headgear assembly can include a blocking element coupled to each of the side straps, each blocking element configured to limit sliding of the side strap within the passage to maintain a minimum length of the lower portion. The blocking element may not limit movement of the filament within the side strap.

In some embodiments, a respiratory mask assembly includes a headgear assembly and a mask interface. The headgear assembly includes an upper headgear loop, a lower headgear loop, and a side strap coupling the upper headgear loop and the lower headgear loop on each side of a user's face in use. The mask interface is coupled to the side straps, and a position of the mask interface along a length of the side straps is configured to be adjusted to adjust a length of the upper headgear loop relative to the lower headgear loop.

The headgear assembly can include a top strap configured to extend across a top of the user's head in use, the top strap extending between and connecting opposing sides of the upper headgear loop. The side straps can be elastic. The side strap can form a portion of the upper headgear loop and the lower headgear loop.

BRIEF DESCRIPTION OF THE DRAWINGS

FIG. 25A shows a schematic of an automatic headgear adjustment mechanism in an expanded state.

FIG. 25B shows a schematic of the automatic headgear adjustment mechanism of FIG. 25B in a retracted state.

DETAILED DESCRIPTION

Figure 1:
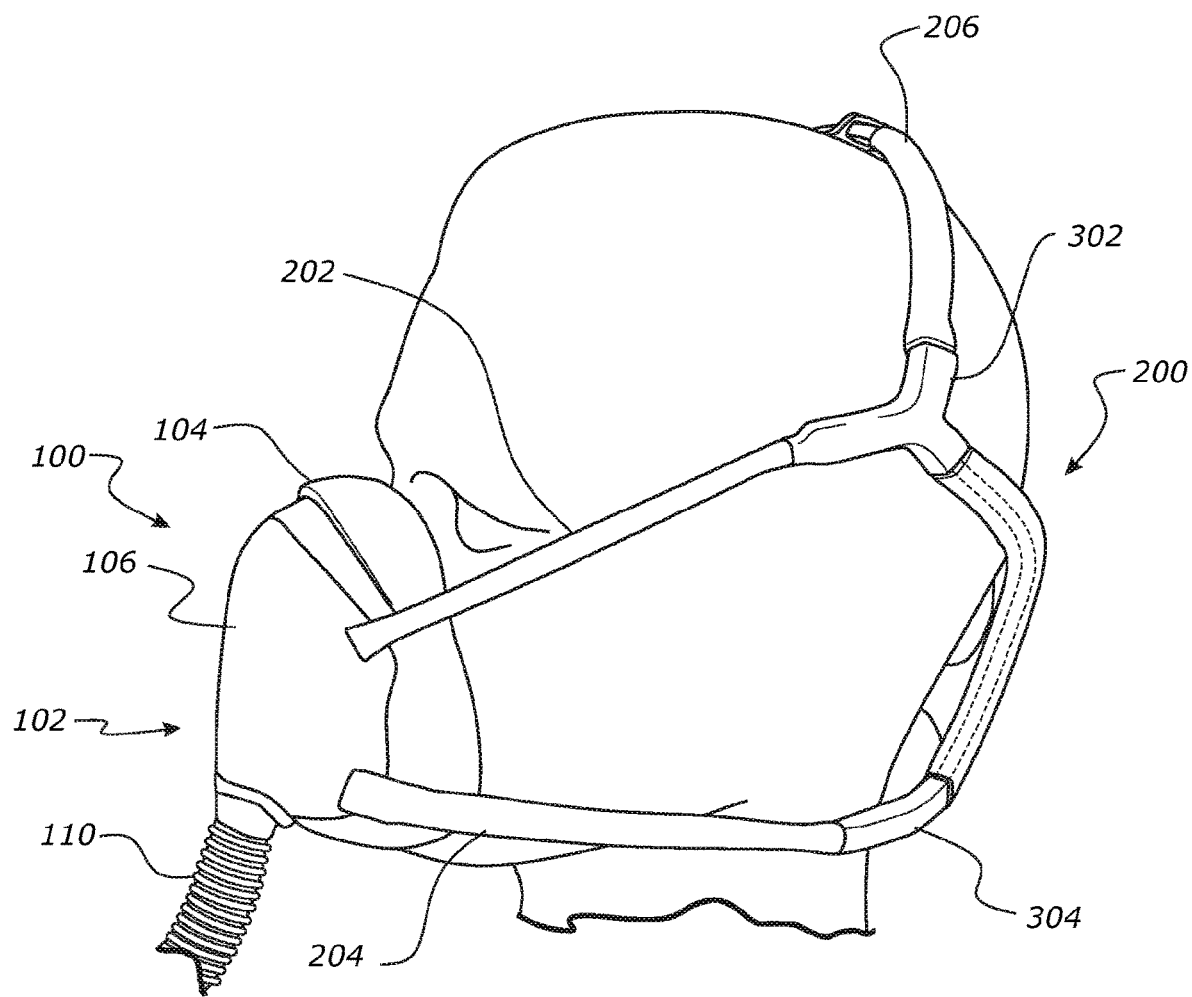
FIG. 1 is a side perspective view of an example embodiment of a mask assembly including a mask interface and a headgear assembly shown on a user.

Embodiments of systems, components and methods of assembly and manufacture will now be described with reference to the accompanying figures, wherein like numerals refer to like or similar elements throughout. Although several embodiments, examples and illustrations are disclosed below, it will be understood by those of ordinary skill in the art that the inventions described herein extend beyond the specifically disclosed embodiments, examples and illustrations, and can include other uses of the inventions and obvious modifications and equivalents thereof. The terminology used in the description presented herein is not intended to be interpreted in any limited or restrictive manner simply because it is being used in conjunction with a detailed description of certain specific embodiments of the inventions. In addition, embodiments of the inventions can comprise several novel features and no single feature is solely responsible for its desirable attributes or is essential to practicing the inventions herein described.

Certain terminology may be used in the following description for the purpose of reference only, and thus are not intended to be limiting. For example, terms such as "above" and "below" refer to directions in the drawings to which reference is made. Terms such as "front," "back," "left," "right," "rear," and "side" describe the orientation and/or location of portions of the components or elements within a consistent but arbitrary frame of reference which is made clear by reference to the text and the associated drawings describing the components or elements under discussion. Moreover, terms such as "first," "second," "third," and so on may be used to describe separate components. Such terminology may include the words specifically mentioned above, derivatives thereof, and words of similar import.

Figure 2:
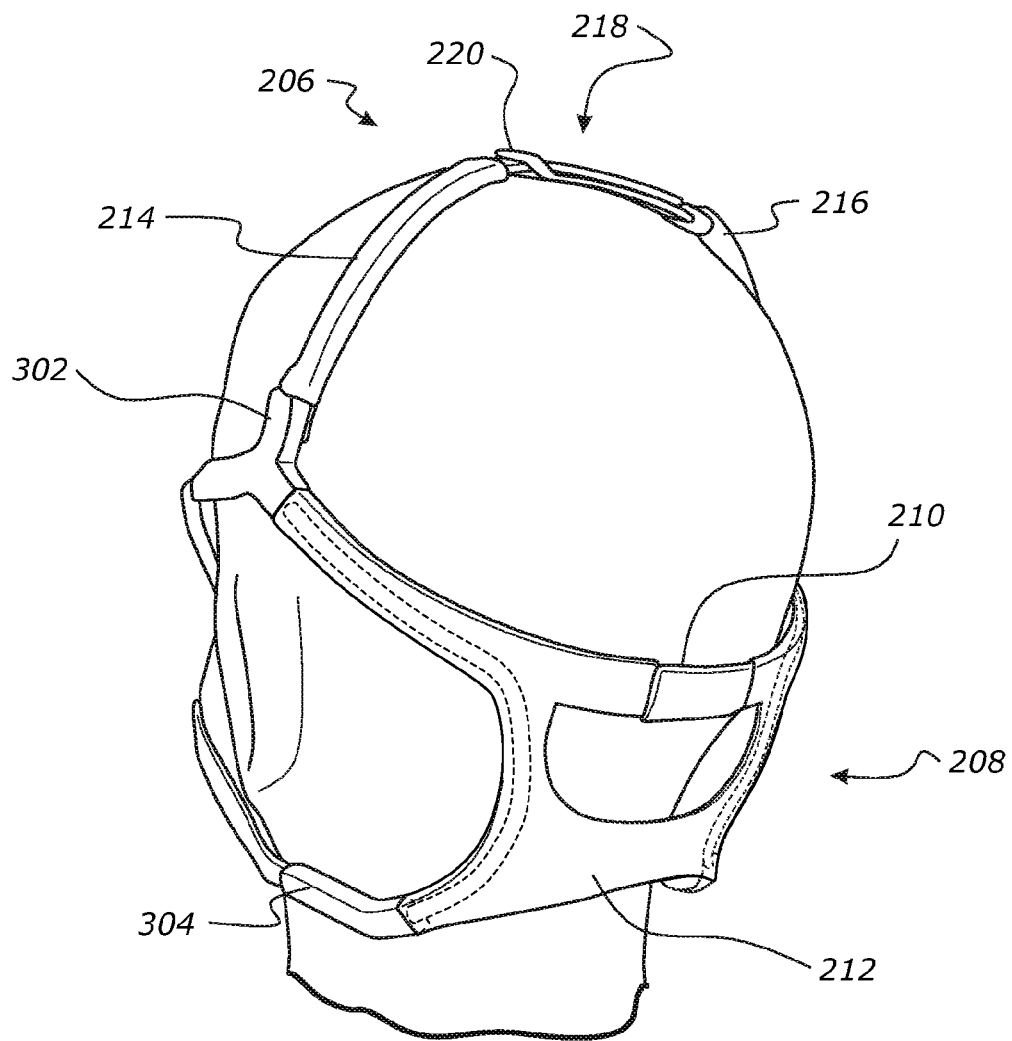
FIG. 2 is a rear perspective view of the mask assembly of FIG. 1 shown on a user.

The present disclosure relates to a respiratory mask system or mask assembly 100 for the delivery of respiratory therapy to a patient. For example, FIGS. 1 and 2 illustrate an example embodiment of a mask assembly 100 including a mask interface 102 and a headgear assembly 200. The mask interface 102 includes a seal or cushion 104 that seals around the user's nose and/or mouth in use and a frame or housing 106 that supports the seal 104 and couples the seal 104 to the headgear 200 and/or a gas delivery conduit 110. In the illustrated embodiment, the mask interface 102 is a full face mask, and the seal 104 seals around the user's nose and mouth in use. The seal 104 can be removably coupled to the housing 106 in use. The housing 106 can comprise one or more portions or pieces. For example, the housing 106 can have a first piece that directly supports the seal 104 and a second piece that directly supports the headgear 200. The first and second pieces can be permanently or removably coupled to one another. The headgear 200 supports the mask interface 102 in a suitable position on the user's face in use.

The headgear 200 includes a pair of upper side straps 202, a pair of lower side straps 204, a top strap 206, and a rear section 208. One of the pair of upper side straps 202 and one of the pair of lower side straps 204 are located on each side of the user's head in use and can be mirror images of one another. Each of the upper 202 and lower 204 side straps apply force vectors to the mask interface 102 in use. The headgear 200 can therefore be considered a four-point headgear. The side straps 202 and 204 on each side of the user's head can be coupled to one another by the top strap 206 and the rear section 208.

The headgear 200 can also include at least one connector on each side of the headgear 200. Each connector connects two or more straps or portions of the headgear assembly. That is, each connector connects two or more of one of the side straps 202, 204, the rear section 208, and the top strap 206. Each connector may be considered to form a junction body or junction element of the headgear 200. The headgear 200 of FIGS. 1 and 2 includes two upper connectors 302 (also referred to as upper side strap connectors herein) and two lower connectors 304 (also referred to as lower side strap connectors herein), with one of each located on each side of the headgear 200. Therefore, each side of the headgear 200 includes an upper connector 302 and a lower connector 304. Each connector 302, 304 is disposed or positioned away from the mask interface 102. Each upper connector 302 is configured to be disposed above a user's ear in use. In the illustrated embodiment, each upper connector 302 connects one of the upper side straps 202, the top strap 206, and the rear section 208, e.g., an upper section 210 of the rear section 208 as described herein. Each lower connector 304 is configured to be disposed below and/or behind the user's ear in use. Each lower connector 304 connects one of the lower side straps 204 and the rear section 208, e.g., a lower section 212 of the rear section 208 as described herein.

Each connector 302, 304 is associated with an automatically adjusting headgear mechanism as described herein. Examples of such an automatically adjusting headgear mechanism are discussed in relation to FIGS. 44A-D below. For example, each connector 302, 304 houses a control mechanism of one of the automatically adjusting headgear mechanisms. The control mechanisms can include one or more lock mechanisms, for example, directional locks, as described herein. Each connector 302, 304 has a generally hollow body that receives and/or houses the respective control mechanism. The body may be formed of a rigid material or a soft material such as silicone. Forming the body from silicon can provide for a more comfortable engagement with the user's head in use. The connector body may be formed as two components that are clipped or otherwise coupled together over, around, or about the control mechanism. Alternatively, the connector body may be formed by overmoulding the connector body to or around the control mechanism. Alternatively, the connector body may be formed with an opening through which the control mechanism is inserted. A cap may be attached to the connector body over the opening to enclose the control mechanism. The connector body includes apertures at first and second ends of the connector body that allow a filament of the automatically adjusting headgear mechanism to extend into and/or through the connector and/or control mechanism from either end of the connector and/or control mechanism.

Figure 12:
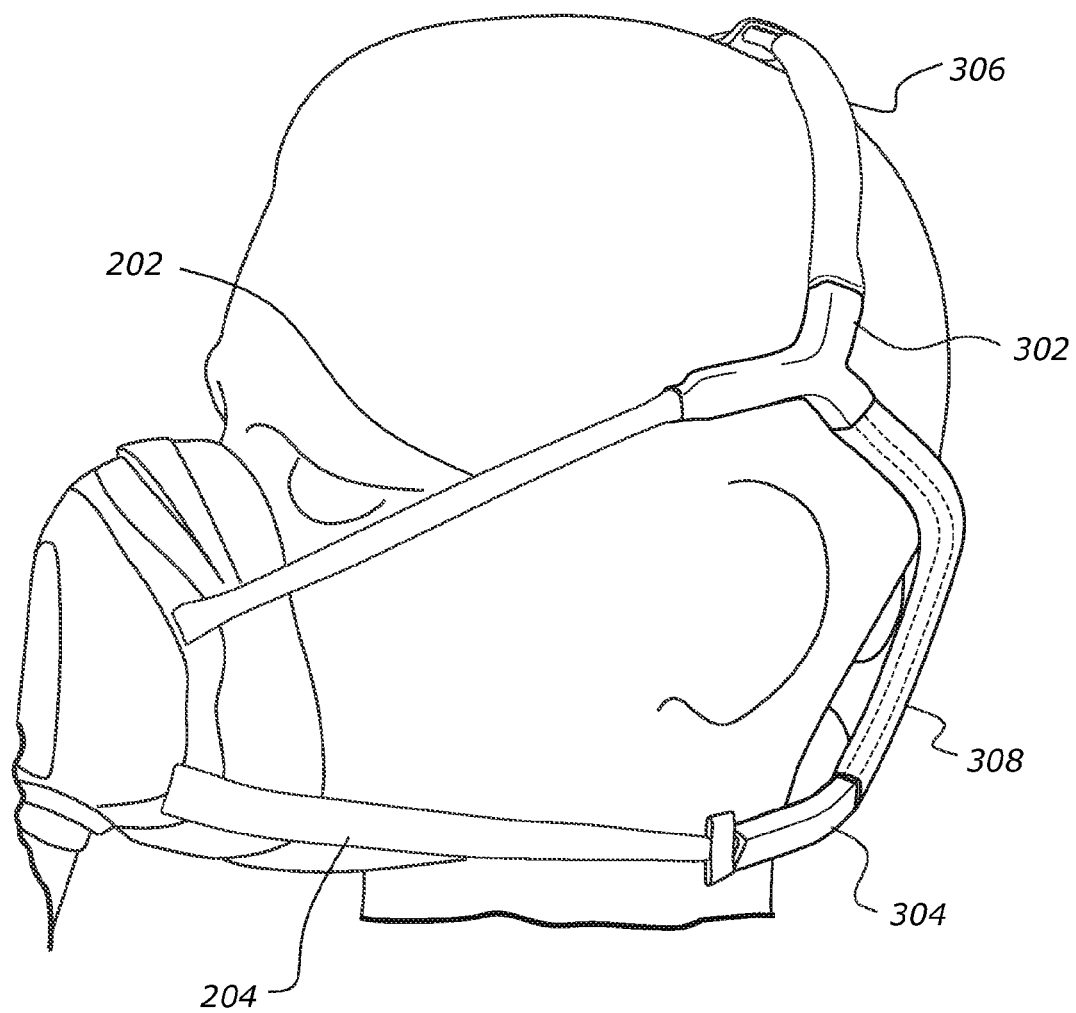
FIG. 12 is a side perspective view of the mask assembly of FIG. 1, highlighting automatically adjustable mechanisms.

In the illustrated embodiment, each upper side strap 202 has a first end connected to the mask interface 102 and a second end connected to one of the upper side strap connectors 302. Each lower side strap 204 has a first end connected to the mask interface 102 and a second end connected to one of the lower side strap connectors 304. The upper side straps 202 and/or lower side straps 204 can be rigidly, fixedly, or permanently connected to the mask interface 102 as shown in FIGS. 1-2 and 12. Alternatively, the upper side straps 202 and/or lower side straps 204 can be removably connected to the mask interface 102. The side straps 202, 204 are coupled to lateral sides of the mask interface 102. This can advantageously allow for a relatively clear and unobstructed view above and/or through the center of the housing 106. A relatively clear and unobstructed view may present a more humanistic and/or aesthetically pleasing appearance to the patient's bed partner. The top strap 206 extends between and is connected to the upper side strap connectors 302. The rear section 208 extends between and is connected to the upper side strap connectors 302 and lower side strap connectors 304. As described in greater detail herein, the rear section 208 can include an upper strap or section 210 and a lower strap or section 212. The upper strap or section 210 can include two ends, each connected to one of the upper side strap connectors 302. The lower strap or section 212 can include two ends, each connected to one of the lower side strap connectors 304. The upper and lower straps 210, 212 can be interconnected, such as via vertical straps or sections.

The headgear 200 includes one or more adjustable components and/or adjustment mechanisms to allow for donning and/or doffing of the headgear 200 and/or to allow the headgear 200 to be adjusted to an appropriate size for the user. For example, the top strap 206 can be adjustable, e.g., manually adjustable in the illustrated embodiment, and the upper 202 and/or lower 204 side straps can be adjustable, e.g., automatically adjustable in the illustrated embodiment. In some configurations, the rear section 208 can allow for temporary expansion during donning and/or doffing of the mask assembly 100.

In the illustrated embodiment the top strap 206 comprises two strap portions, a left portion 214 and a right portion 216. The left and right portions 214, 216 are separate from one another and have a free end and a fixed end. The free ends are configured to be adjustably connected by an adjustment mechanism 218. In the illustrated embodiment, each of the fixed ends extends from a location at or near a junction between one of the upper side straps 202 and the rear section 208.

The adjustment mechanism 218 is configured to provide a means to adjust and secure the top strap 206 in a desired adjusted length and thus adjust the size and/or tightness setting of the headgear 200. Adjustment of the length of the top strap 206 can define the positioning, in use, of the upper side straps 202 relative to the top of a user's ear. Shortening the length of the top strap 206 may position the upper side straps 202 higher above the user's ears thus avoiding contact between the upper side straps 202 and the user's ears. This may improve comfort for the user, as contact between the upper side straps 202 and the top of the user's ears may cause irritation or pressure points that over time can lead to pressure sores.

In the illustrated embodiment, the free end of the right portion 216 includes a guide loop 220 and a plurality of holes spaced along the length of the strap. The holes extend through the thickness of the top strap 206. The free end of the left portion 214 includes a pip or post that protrudes from an internal surface of the strap. In other embodiments, the right portion 216 can instead include a pip or post and the left portion 214 can include a guide loop and plurality of holes.

The guide loop 220 comprises a loop structure that forms an aperture at the end of the right portion 216. The free end of the left portion 214 is configured to pass through the aperture formed by the guide loop 220. Thus, the left portion 214 and the right portion 216 can be slid relative to one another to vary an overlapping distance of the left and right portions 214, 216 and, thus, vary a length of the top strap 206. The guide loop 220 can also maintain a link between the left and right portions 214, 216 when the adjustment mechanism 218 is not engaged. This may improve ease of use by maintaining a connection between the portions 214, 216. The guide loop 220 can be angled away from the internal surface such that the aperture is at least partially offset from the thickness of the strap. This allows the left portion 214 to pass through the guide loop 220 and overlap with the right portion 216 without the left portion 214 having to bend or deform to any significant extent.

The post is configured to pass through any of the holes in the right portion 216. The holes and post are sized, shaped and/or otherwise configured to allow the post to pass through the holes and to retain the post once passed through a selected one of the holes, at least in response to normal or expected forces. However, the post can be deliberately removed from the holes to permit separation of the left and right portions 214, 216 of the top strap 206, to allow for re-sizing of the headgear 200. Passing of the post through the holes can be accomplished by deformation of one or both the post and holes. In alternative embodiments there may be a plurality of posts.

In alternative embodiments the adjustment mechanism 218 may comprise any other suitable means of adjustably connecting the free ends of the top strap 206, such as but not limited to hook and loop fasteners, buckles, magnetic connectors, etc. Alternatively, the left and right portions 214, 216 can be connected, e.g., permanently connected via, for example, a section of an elastic material that allows the top strap 206 to stretch and lengthen to some extent if needed. In other embodiments, the top strap 206 can be a one-piece and/or non-adjustable strap.

The rear section 208 can allow for temporary expansion during donning and/or doffing of the mask assembly 100. The rear section 208 can have a rigid or non-adjustable upper strap or section 210 and an adjustable lower strap or section 212. The lower section 212 can be elastic, as shown in FIG. 2. Other adjustment mechanisms are also possible, for example as shown and described herein. The adjustable lower section 212 allows the lower section 212 to be expanded temporarily while donning and/or doffing the mask assembly 100. The temporary expansion allows the lower side straps 204 to pass over the patient's ears with reduced, minimal, or no contact to avoid causing patient discomfort. Once the lower side straps 204 have passed the ears, the tension and/or expansion of the lower section 212 can be released to allow the lower section 212 to return to its regular, default, or non-expanded size. Although the lower section 212 is adjustable to allow for temporary expansion for donning and/or doffing, when disposed on the user's head in use, the lower section 212 has a fixed length. The lower section 212 may allow for only temporarily expansion for donning and/or doffing, and may not allow for headgear size adjustment 200. In other words, the fixed length of the lower section 212 when not temporarily expanded for donning and/or doffing may not be adjusted by the user.

Figure 3A:
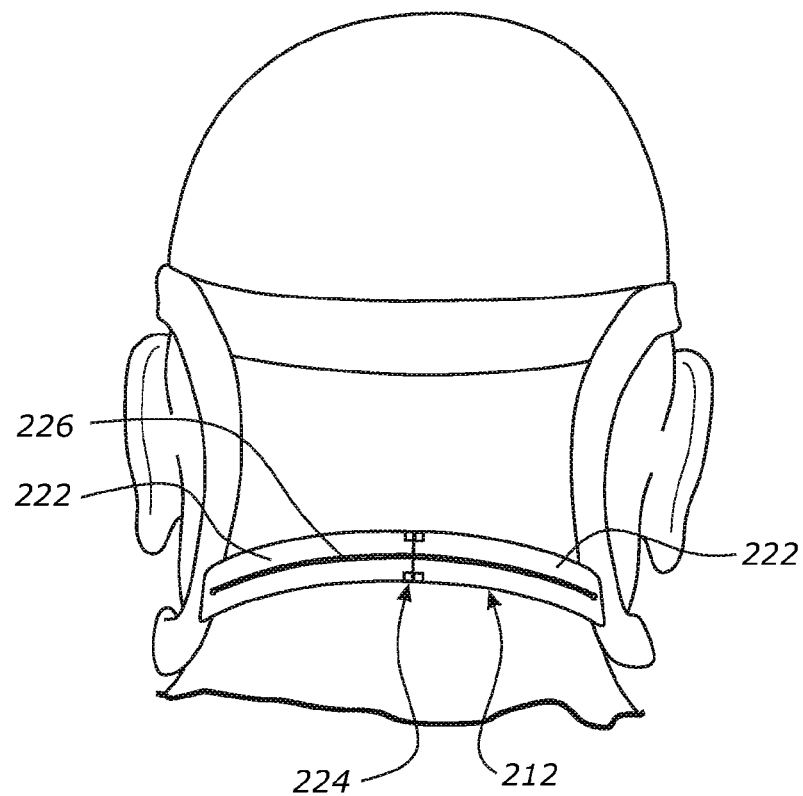
FIG. 3A is a rear view of a headgear assembly including a magnetic connection shown on a user showing a rear section of the headgear assembly in a closed state.
Figure 3B:
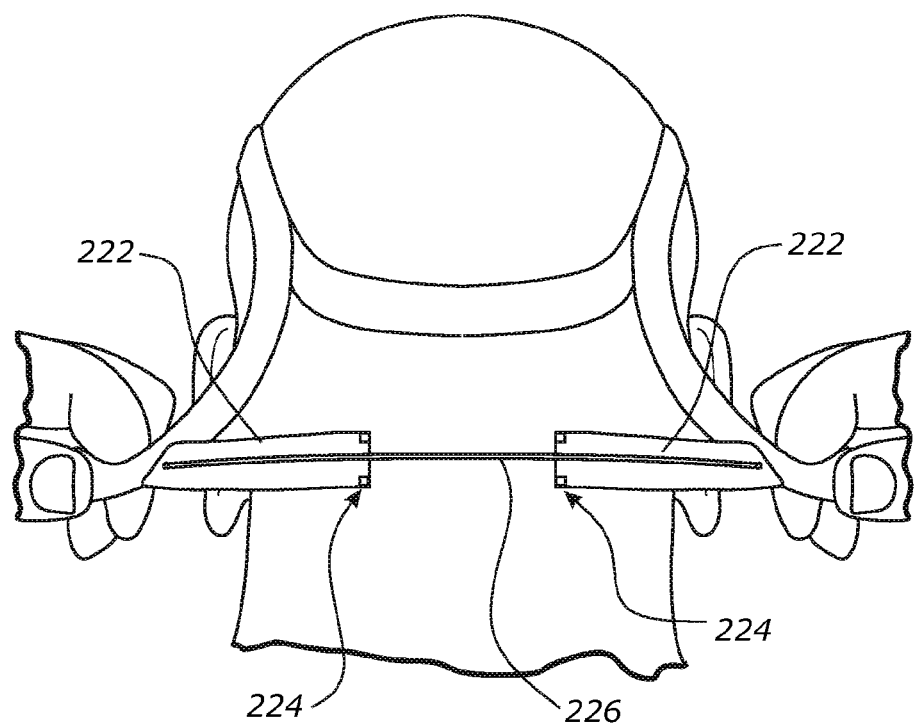
FIG. 3B is a rear view of the headgear assembly of FIG. 3A shown on a user showing the rear section in an open state.

The lower section 212 can include other adjustment mechanisms instead of or in addition to elastic. For example, the lower section 212 can include a break-fit arrangement in the form of a magnetic connection as shown in FIGS. 3A and 3B. The break-fit arrangement can include a sleeve or tether to help guide movement of components of the magnetic connection together. In the illustrated embodiment, the lower section 212 includes two non-elastic sections 222. The two non-elastic sections 222 are removably connected to each other at or near a center or middle of the lower section 212 with magnets 224 positioned at or near free ends of each of the non-elastic sections. In the illustrated embodiment, each non-elastic section 222 includes an upper magnet 224 and a lower magnet 224, but more or fewer magnets are also possible. The magnets 224 of one of the non-elastic sections 222 have a polarity opposite to the polarity of the magnets 224 of the other non-elastic section 222 such that the magnets 224 of the two non-elastic sections 222 are attracted to each other. Therefore, in a default state, shown in FIG. 3A, the two non-elastic sections 222 are coupled together. The two non-elastic sections 222 are permanently connected to each other with a tether, e.g., an elastic tether 226, to maintain a connection and/or guide the sections 222 toward one another. The elastic tether 226 can extend through or along both non-elastic sections 222.

To don and/or doff the headgear 200, the user pulls the non-elastic sections 222 away from each other, applying sufficient force to break the magnetic bond between the magnets 224 and separate the two non-elastic sections 222 from each other as shown in FIG. 3B. This enlarges the lower section 212 and allows the mask assembly 100 to be donned and/or doffed with reduced, minimal, or no contact of the lower side straps 204 with the user's ears. As the two non-elastic sections 222 separate from each other, the elastic tether 226 stretches, as shown in FIG. 3B. When the user releases the tension or force pulling the non-elastic sections 222 apart, the elastic tether 226 attempts to return to its unstretched state, thereby pulling the two non-elastic sections 222 back toward each other. When the magnets 224 of the two non-elastic sections 222 are in close enough proximity to each other, the magnets 224 attract each other to reconnect the two non-elastic sections 222. The magnets can be designed or selected such that the force of attraction between the magnets 224 is greater than the blow-off force in use. For example, the force of attraction may be at least 20 N.

Figure 4A:
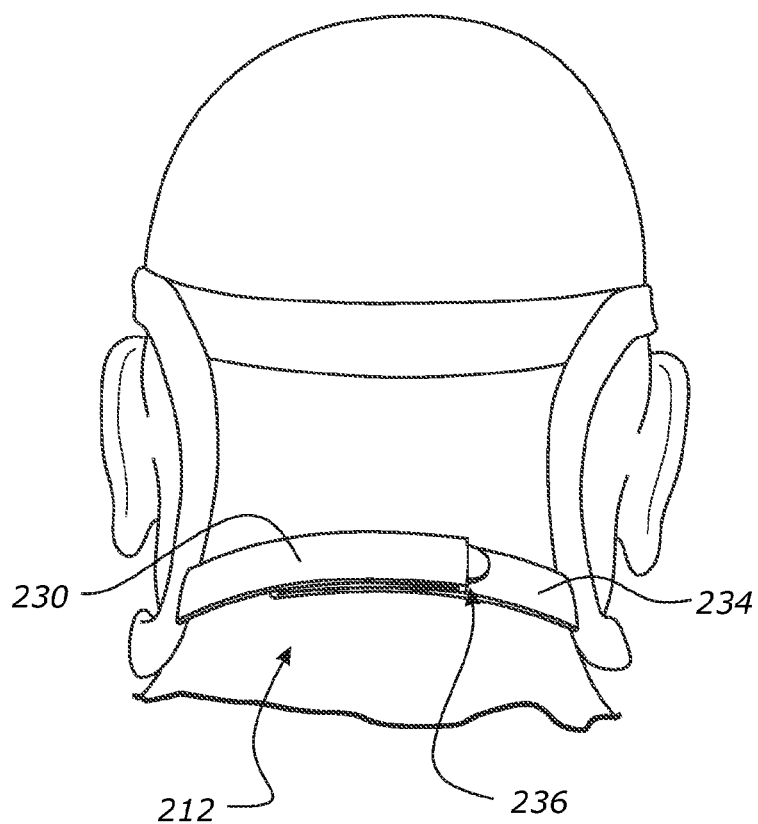
FIG. 4A is a rear view of a headgear assembly including a foldable connection shown on a user showing a rear section of the headgear assembly in a closed state.

In other arrangements, the lower section 212 can include a foldable adjustment mechanism, for example, similar to a deployment buckle and/or deployment clasp as shown in FIGS. 4A-5B. The lower section 212 includes a first link 230, a second link 232, and a third link 234. A first end of the second link 232 is hingedly coupled to the first link 230, and an opposite second end of the second link 232 is hingedly coupled to the third link 234. In a closed state, shown in FIGS. 4A and 5A, the first 230, second 232, and third 234 links are folded such that the first 230, second 232, and third 234 links are stacked or overlap each other and the second link 232 is sandwiched between the first link 230 and the third link 234. The links can have a curved shape or contour. The links can be curved or contoured such that when in the closed state and positioned on the user's head, as shown in FIG. 4A, the links are forward facing concave. Such a contour can generally accommodate or follow the curvature of the back of the user's head. When in an open, expanded state, as described below, the first 230 and third 234 links can be forward facing concave and the second link 232 can be forward facing convex.

Figure 4B:
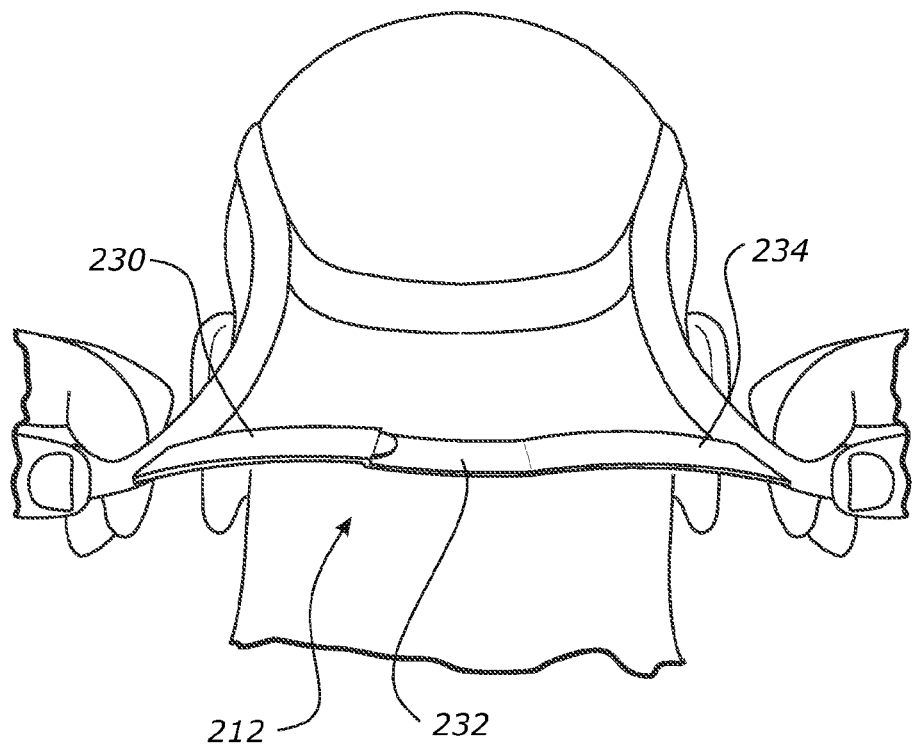
FIG. 4B is a rear view of the headgear assembly of FIG. 4A shown on a user showing the rear section in an open state.
Figure 5A:
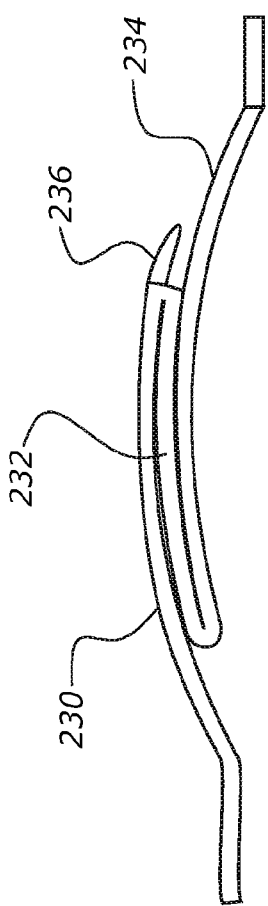
FIG. 5A is a bottom view of the watch clasp connection of the headgear assembly of FIG. 4A in the closed state.
Figure 5B:
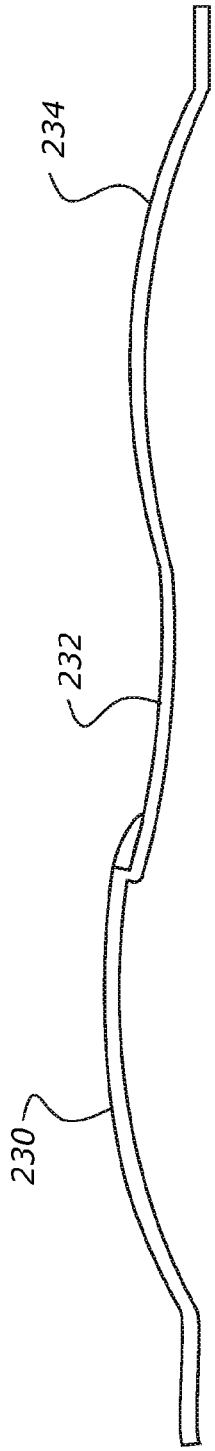
FIG. 5B is a bottom view of the watch clasp connection of FIG. 5A in the open state.
Figure 6A:
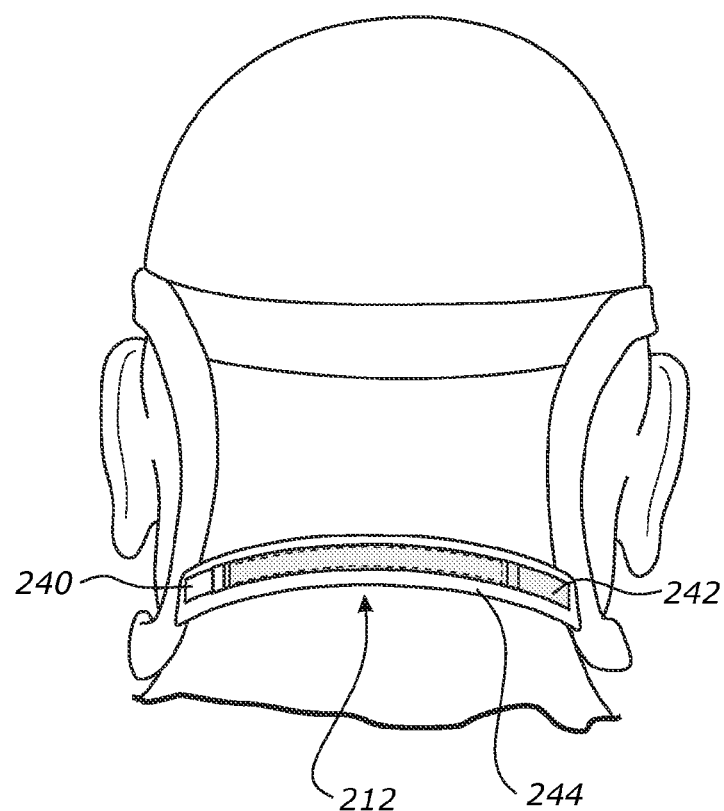
FIG. 6A is a rear view of a headgear assembly including overlapping rails in an elastic sleeve on a user showing a rear section of the headgear assembly in a closed state.
Figure 6B:
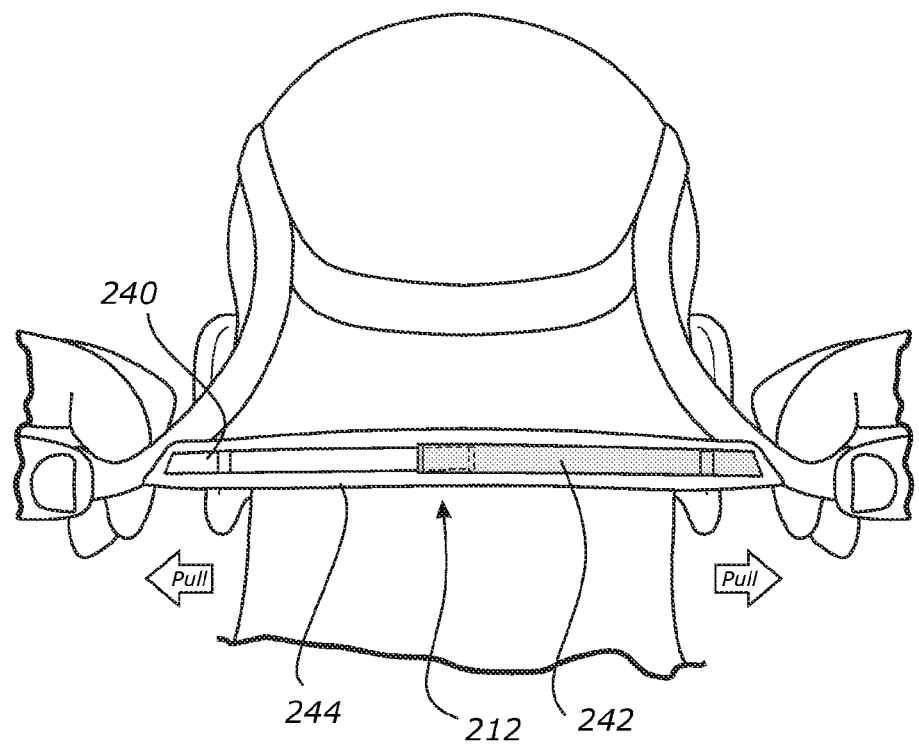
FIG. 6B is a rear view of the headgear assembly of FIG. 6A shown on a user showing the rear section in an open state.

To move the adjustment mechanism to the open, expanded state, shown in FIGS. 4B and 5B, the user lifts and/or pulls the first link 230 (e.g., lifts and/or pulls the end of the first link 230 overlapping the second 232 and third 234 links) away from the third link 234. This movement also lifts and/or pulls the first end of the second link 232 away from the third link 234 so that the second link 232 hinges relative to the first 230 and third 234 links and the first 230, second 232, and third 234 links unfold. In the open state, the second link 232 is disposed longitudinally between, or substantially between, the first link 230 and the third link 234. The first 230, second 232, and/or third 234 links can be rigid or semi-rigid, which can allow for defined folding points (e.g., at the hinges between the first 230 and second 232 links and between the second 232 and third 234 links). In some embodiments, the first link 230 includes a tab 236 at or near the end of the first link 230 connected to the second link 232. The tab 236 can provide the user a location to grip to open and/or close the connection mechanism. The tab 236 may be constructed to give tactile feedback to the patient to signal they have gripped the correct location.

In the open state, the lower section 212 has an expanded length to allow the headgear 200 to be donned and/or doffed with reduced, minimal, or no contact of the lower side straps 204 with the user's ears. To close the connection mechanism, e.g., once the lower side straps 204 have cleared the user's ears, the user moves the first link 230 back toward the third link 234 such that the second link 232 hinges relative to the first 230 and third 234 links to fold the links and sandwich the second link 232 between the first 230 and third 234 links. The lower section 212 can be secured in the closed state via any appropriate means, e.g., hook and loop fastener(s), one or more clips, one or more magnets, interference fit(s), etc. between the first link 230 and the second link 232, between the second link 232 and the third link 234, between the tab 236 and the second link 232 and/or between the tab 236 and the third link 234.

Figure 7A:
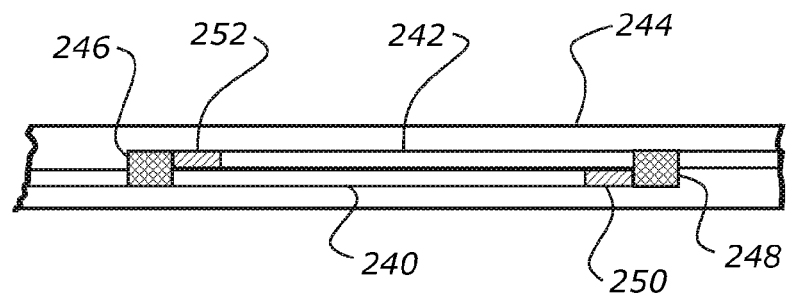
FIG. 7A is a detail view of the overlapping rails and elastic sleeve of the headgear assembly of FIG. 6A in the closed state.
Figure 7B:
FIG. 7B shows the overlapping rails and elastic sleeve of FIG. 7A in the open state.
Figure 7C:
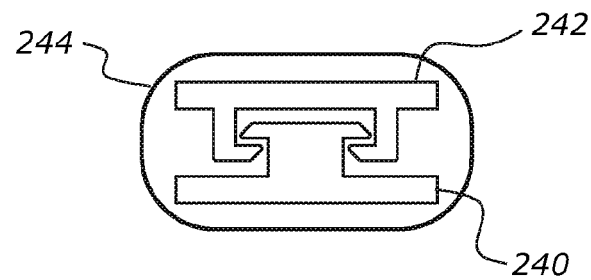
FIG. 7C is a cross-section of the overlapping rails and elastic sleeve of FIG. 7A.

In some embodiments, the lower section 212 includes a sliding or telescoping assembly. In the illustrated arrangement, the lower section 212 includes overlapping and/or interlocking rails housed in an elastic sleeve 244 as shown in FIGS. 6A-7C. The lower section 212 includes an inner rail 240 having a first end at or near a first lateral side of the lower section 212 (the user's left in the illustrated embodiment) and a second end extending toward a second, opposite lateral side of the lower section 212, and an outer rail 242 having a first end at or near the second lateral side of the lower section 212 (the user's right in the illustrated embodiment) and a second end extending toward the first lateral side. The inner 240 and outer 242 rails overlap and/or interlock, for example as shown in FIG. 7C, to allow sliding movement in a length direction and prevent separation and/or relative movement in one or both of the other (width and thickness) directions. A first end of the elastic sleeve 244 is fixed relative to the first end of the inner rail 240, and a second, opposite end of the elastic sleeve 244 is fixed relative to the first end of the outer rail 242.

In some configurations, the inner rail 240 includes a metal or magnetic portion 250 at the second end of the inner rail 240. The outer rail 242 includes a metal or magnetic portion 252 at the second end of the outer rail 242. A first magnet 246 is disposed along the inner rail 240 at a location spaced from the second end of the inner rail 240. A second magnet 248 is disposed along the outer rail 242 at a location spaced from the second end of the outer rail 242. The metal or magnetic portion 252 of the outer rail 242 is attracted to the first magnet 246, and the metal or magnetic portion 250 of the inner rail 240 is attracted to the second magnet 248. In a closed state, shown in FIGS. 6A and 7A, the magnetic portion 252 of the outer rail 242 abuts or is in magnetic connection with the first magnet 246 and the magnetic portion 250 of the inner rail 240 abuts or is in magnetic connection with the second magnet 248. The magnetic attraction or bond between the respective magnetic portions and magnets holds the lower section 212 in the closed state.

To move the lower section 212 to an open or expanded state, the user pulls the first ends of the inner 240 and outer 242 rails away from each other in a lengthwise direction along an axis parallel or generally parallel to longitudinal axes of the inner 240 and outer 242 rails. When the user applies sufficient force to overcome or break the magnetic bond between the respective magnetic portions and magnets, the inner 240 and outer 242 rails slide relative to each other and away from each other along an axis parallel or generally parallel to the longitudinal axes of the inner 240 and outer 242 rails, thereby decreasing the overlap between the inner 240 and outer 242 rails. As the inner 240 and outer 242 rails slide away from each other, the lower section 212 lengthens and the elastic sleeve 244 stretches. The inner 240 and outer 242 rails can have lengths selected such that at a maximum length of the lower section 212, the inner 240 and outer 242 rails still overlap to some extent to ensure the inner 240 and outer 242 rails remain connected.

In the open or expanded state, the lower section 212 has an expanded length to allow the headgear 200 to be donned and/or doffed with reduced, minimal, or no contact of the lower side straps 204 with the user's ears. Once the lower side straps 204 have cleared the user's ears, the user can release the tension on the lower section 212. When the tension on the lower section 212 pulling the inner 240 and outer 242 rails apart is released, the elastic sleeve 244 attempts to return to its unstretched state, thereby moving the inner 240 and outer 242 rails toward each other and increasing the overlap of the inner 240 and outer 242 rails. When the magnetic portions are in close enough proximity to the magnets, the magnetic portions and magnets attract each other to return the lower section 212 to the closed state. Although an elastic sleeve 244 is shown, other biasing members or arrangements can be used to bias the inner 240 and outer 242 rails toward the closed state.

FIGS. 8A-9G illustrate another embodiment of the lower section 212 including a clip together connection mechanism. The lower section 212 includes a first strap 260 and a second strap 262. The first 260 and second 262 straps can be non-elastic. In the illustrated embodiment, the first strap 260 is on the user's left in use and the second strap 262 is on the user's right in use, but the first 260 and second 262 straps can be reversed. The first strap 260 includes a female connector 264 at a medial end of the first strap 260. The second strap 262 includes a male connector 266 at a medial end of the second strap 262. In a closed state, shown in FIGS. 8A, 9B, 9E, and 9F, the male connector 266 is received in, e.g., clipped into, the female connector 264. The male connector 266 and female connector 264 can be secured together via an interference, interlocking or snap fit. The lower section 212 also includes an elastic tether 268 coupled to and connecting the first strap 260 and second strap 262. The elastic tether 268 can contact the rear of the patient's head in use, which can cushion contact between the connectors and the patient's head.

Figure 8A:
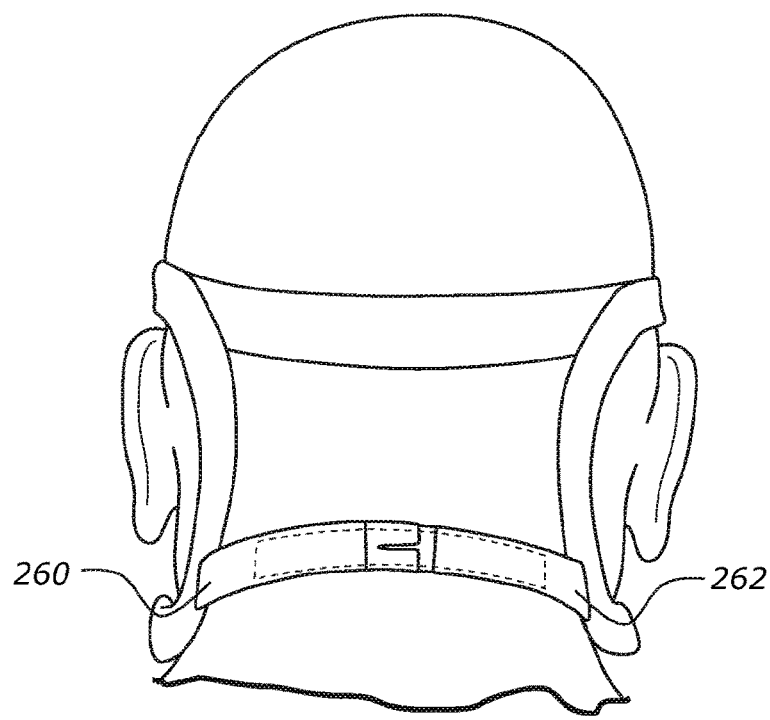
FIG. 8A is a rear view of a headgear assembly including a peel apart connection shown on a user showing a rear section of the headgear assembly in a closed state.
Figure 8B:
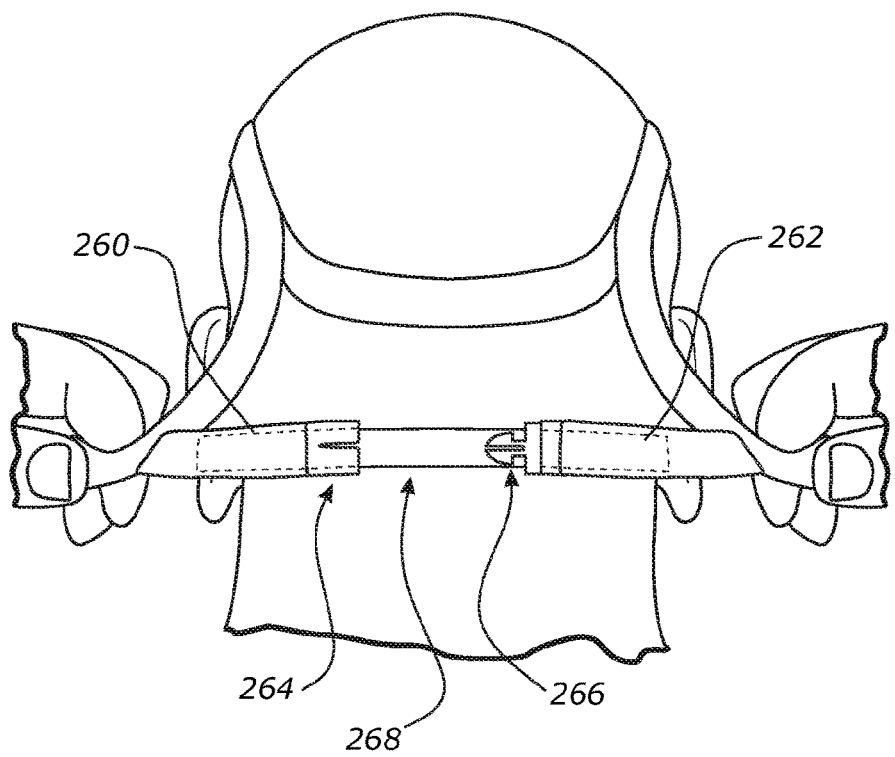
FIG. 8B is a rear view of the headgear assembly of FIG. 8A shown on a user showing the rear section in an open state.

To transition the lower section 212 to an open or expanded state, the male connector 266 is removed from the female connector 264, and the first 260 and second 262 straps are pulled apart from each other, as shown in FIG. 8B. As the first 260 and second 262 straps are pulled apart from each other, the elastic tether 268 stretches. In the open or expanded state, the lower section 212 has an expanded length to allow the headgear 200 to be donned and/or doffed with reduced, minimal, or no contact of the lower side straps 204 with the user's ears. Once the lower side straps 204 have cleared the user's ears, the user can release the tension on the lower section 212. When the tension on the lower section 212 pulling the first 260 and second 262 straps apart is released, the elastic tether 268 attempts to return to its unstretched state, thereby moving the first 260 and second 262 straps toward each other. When the first 260 and second 262 straps have returned to a position close enough together, the male connector 266 can be inserted into the female connector 264 to secure the lower section 212 in the closed state.

Figure 9A:
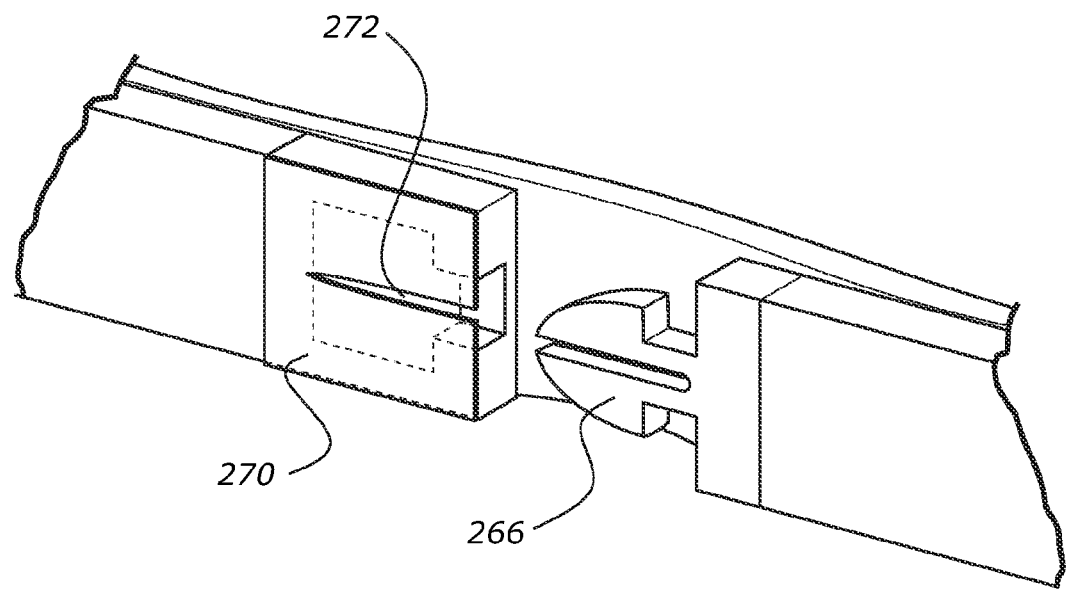
FIG. 9A is a perspective detail view of the peel apart connection of FIG. 8A in the open state.
Figure 9B:
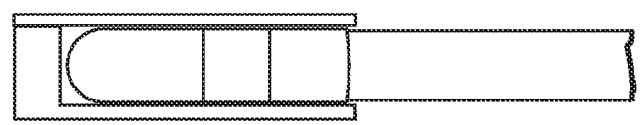
FIG. 9B is a side sectional view of the peel apart connection of FIG. 8A in the closed state.
Figure 9C:
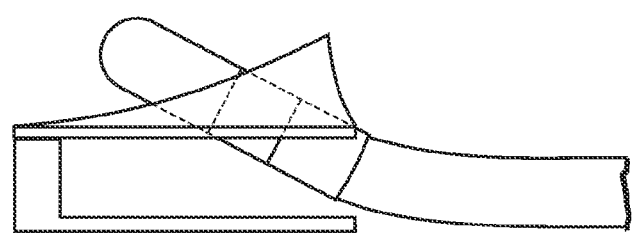
FIG. 9C is a side sectional view of the peel apart connection of FIG. 8A during transition from the closed state to the open state.
Figure 9D:
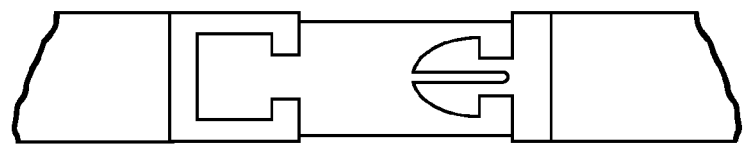
FIG. 9D is a rear sectional view of the peel apart connection of FIG. 8A in the open state.
Figure 9E:
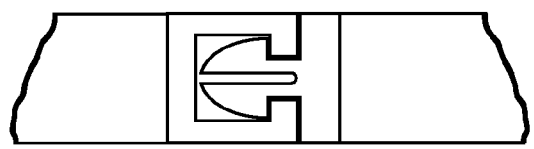
FIG. 9E is a rear sectional view of the peel apart connection of FIG. 8A in the closed state.
Figure 9F:
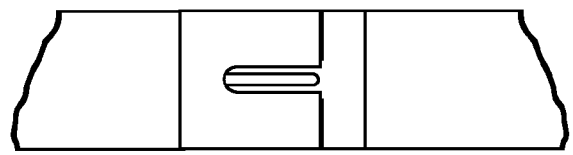
FIG. 9F is a rear view of the peel apart connection of FIG. 8A in the closed state.
Figure 9G:
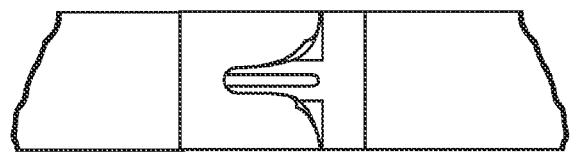
FIG. 9G is a rear view of the peel apart connection of FIG. 8A during transition from the closed state to the open state.
Figure 10A:
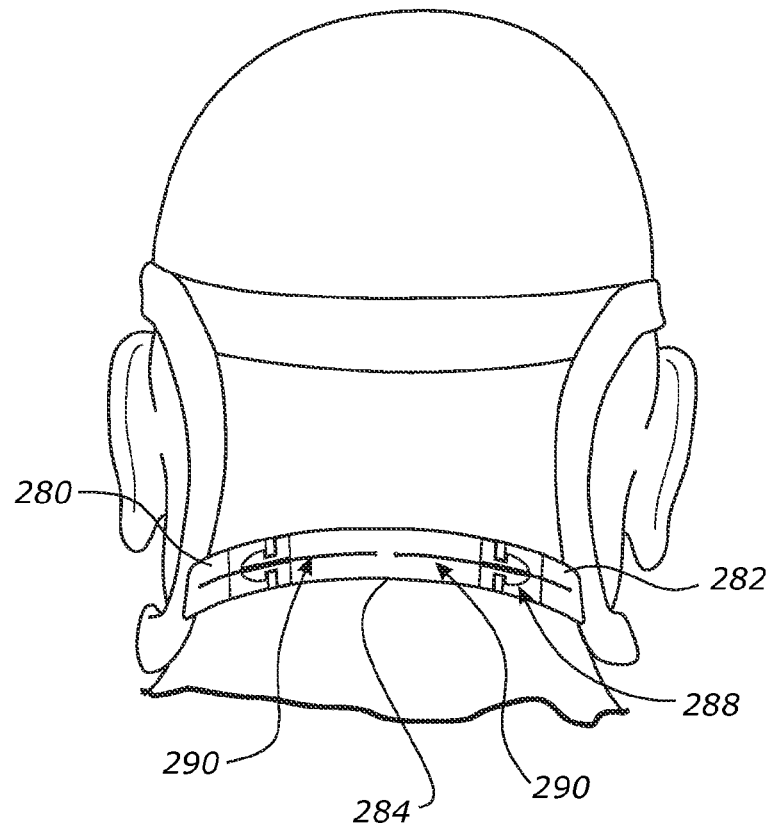
FIG. 10A is a rear view of a headgear assembly including two peel apart connections shown on a user showing a rear section of the headgear assembly in a closed state.
Figure 10B:
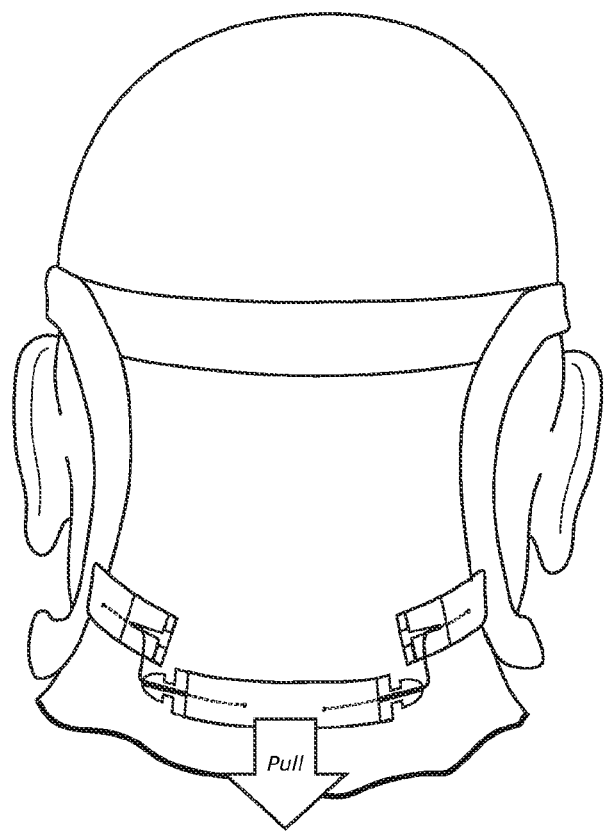
FIG. 10B is a rear view of the headgear assembly of FIG. 10A shown on a user showing the rear section in an open state.

In some embodiments, the female connector 264 includes at least a rear face 270 made of a deformable material, e.g., rubber. As shown in FIGS. 9A and 9F, the rear face 270 has a split 272 extending from the open end of the female connector 264 that receives the male connector 266. To disconnect the male connector 266 from the female connector 264, the user deflects, pivots, and/or pulls the male connector 266 rearward relative to the female connector 262 such that the male connector 266 applies force to the rear face 270. This force causes portions of the rear face 270 on either side of the split 272 to deform and/or deflect outward (relative to the split 272) and rearward (in use; upward in the orientation of FIGS. 9B-9C), as shown in FIGS. 9C and 9G, thereby widening the split 272 and allowing the male connector 266 to pass through the split 272 and disengage from the female connector 264. The male connector 266 is therefore "peeled" out of the female connector 264. In such a configuration, the male connector 266 and female connector 264 are connected and disconnected via different motions or methods—the male connector 266 is longitudinally inserted into the female connector 264 to connect the male connector 266 and female connector 264, whereas the male connector 266 is deflected rearward to peel the male connector 266 rearwardly out of the female connector 264 (perpendicular to the insertion direction). These different motions help reduce the likelihood of the male connector 266 being accidentally disconnected from the female connector 264. The male connector 266 could alternatively or additionally include a release mechanism configured to allow removal in a reverse direction from the insertion direction.

The lower section 212 can include two clip together mechanisms as shown and described, or similar to as shown and described, with respect to FIGS. 8A-9G. For example, the lower section 212 can include a first side portion 280, a second side portion 282, and a central handle portion 284, as shown in FIGS. 10A-11C. The first 280 and second 282 side portions and/or central handle portion 284 can be non-elastic. Each of the first 280 and second 282 side portions includes a female connector 286 at its medial end. Each end of the central handle portion 284 includes a male connector 288 (however, this arrangement could also be reversed). In a closed state, shown in FIGS. 10A and 11B, each male connector 288 is received in, e.g., clipped into, one of the female connectors 286. The male connectors 288 and female connectors 286 can be secured together via an interference, interlocking or snap fit. The lower section 212 also includes one or more biasing members or elastic tethers 290 coupled to and connecting the central handle portion 284 to the first 280 and second 282 side portions. In the illustrated embodiment, the lower section 212 includes a first elastic tether 290 coupled to and connecting the central handle portion 284 and the first side portion 280 and a second elastic tether 290 coupled to and connecting the central handle portion 284 and the second side portion 280.

Figure 11A:
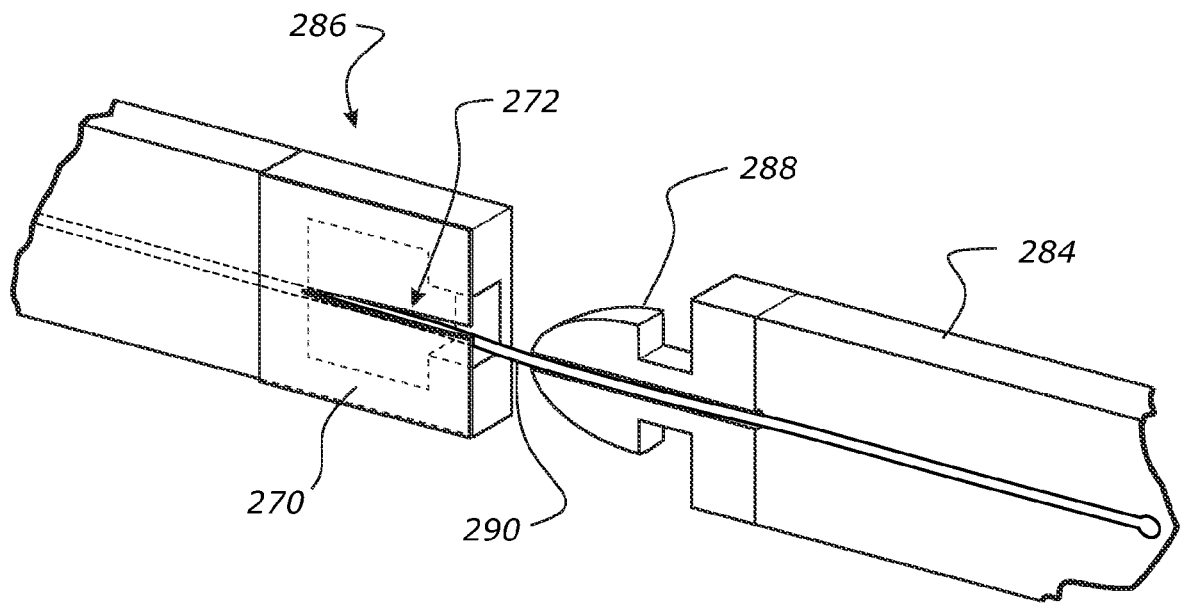
FIG. 11A is a perspective detail view of one of the peel apart connections of FIG. 10A in the open state.
Figure 11B:
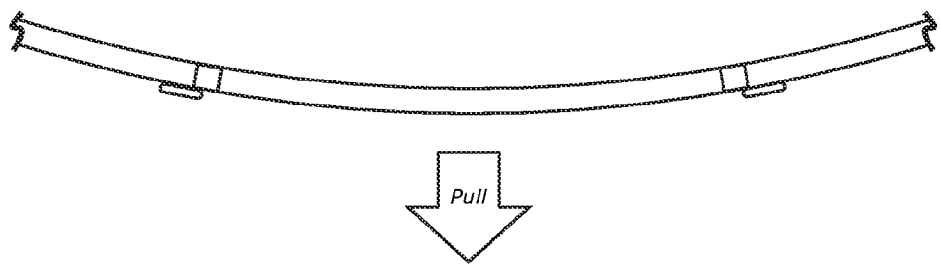
FIG. 11B is a top view of the rear section of the headgear assembly of FIG. 10A in the closed state.
Figure 11C:
FIG. 11C is a top view of the rear section of the headgear assembly of FIG. 10A in the open state.

To transition the lower section 212 to an open or expanded state, the male connectors 288 are removed from the female connectors 286, and the central handle portion 284 is pulled away from the first 280 and second 282 side portions, as shown in FIG. 11C. The female connectors 286 can have rear faces 270 made of a deformable material, e.g., rubber, with a split 272 extending from the end of the female connector 286 that receives the male connector 288, as shown and described herein with respect to FIGS. 9A-9G. To disconnect the male connectors 288 from the female connectors 288, the user can pull the central handle portion 284 rearward away from the first 280 and second 282 side portions such that the male connectors 288 apply force to the rear faces 270. This force causes the portions of the rear faces 270 on either side of the splits 272 to deform and/or deflect outward (relative to the split 272) and rearward (in use), thereby widening the splits 272 and allowing the male connectors 288 to pass through the splits 272 and disengage from the female connectors 286. The male connectors 288 can therefore be "peeled" out of the female connector 286.

With the central handle portion 284 separated from the first 280 and second 282 side portions, the first 280 and second 282 side portions can be pulled longitudinally away from each other to lengthen or expand the lower section 212. As the first 280 and second 282 portions are pulled apart from each other and from the central handle portion 284, the elastic tethers 290 stretch. In the open or expanded state, the lower section 212 has an expanded length to allow the headgear 200 to be donned and/or doffed with reduced, minimal, or no contact of the lower side straps 204 with the user's ears. Once the lower side straps 204 have cleared the user's ears, the user can release the tension on the lower section 212. When the tension on the lower section 212 pulling the first 280 and second 282 side portions apart is released, the elastic tethers 290 attempt to return to their unstretched state, thereby moving the first 280 and second 282 side portions toward each other and the central handle portion 284. When the first 280 and second 282 side portions have returned to a position close enough to the central handle portion 284, the male connectors 288 can be inserted into the female connectors 286 to secure the lower section 212 in the closed state.

As described herein, one or more portions of the headgear 200, e.g., the upper 202 and/or lower 204 side straps, can be automatically adjustable and/or can incorporate one or more directional locks that allow the headgear to reduce in length with a relatively low amount of resistance and resist an increase in length of the headgear with a greater amount of resistance. Preferably, the directional lock(s) are configured to resist at least the blow-off force produced by the mask assembly 100 and, in some configurations, may also resist some amount of hose pull force. In some configurations, a locking force of the directional locks can be overcome to allow lengthening of the headgear for donning of the interface assembly.

As shown in FIG. 12, each of the upper side straps 202 and lower side straps 204 has an associated connector 302, 304, respectively, housing a control mechanism for filaments 330 (shown in FIGS. 25A-25B) used in an automatically adjustable headgear mechanism. Examples of such an automatically adjusting headgear mechanism are discussed in relation to FIGS. 44A-D below. In the illustrated embodiment, the connectors 302, 304 and control mechanisms are located on or connected to the headgear 200, rather than on or connected to the mask interface 102. Each upper side strap 202 has an associated upper connector 302, and each lower side strap 204 has an associated lower connector 304. The illustrated embodiment therefore includes four connectors, each housing a control mechanism for an automatically adjustable headgear mechanism. A filament 330 extends within each of the upper side straps 202 and the lower side straps 204. The side straps 202, 204 or portions thereof can form or include variable length sections, in this case defined by braided elements 332, of an automatic headgear adjustment mechanism, and the filaments 330 can extend within the braided elements 332 as shown in FIGS. 25A-25B. One or more elastic elements 334 (or other suitable biasing arrangements) can be provided and configured to apply a retraction force to the headgear 200, which tends to reduce a circumference of the headgear 200 or reduce a length of a portion of the headgear 200, such as the braided elements 332.

Each control mechanism in the connectors 302, 304 incorporates or includes one or more directional locks, each of which can include one or more lock members 336. Each lock member may be generally in the form of a washer and referred to as "lock washers" or "washers" herein. That is, the lock washers can be relatively flat members defining an aperture through which the filament passes. The lock washers can be configured to frictionally engage with the filament during elongation of the headgear, but allow reduced-friction or relatively friction-free movement during retraction of the headgear. The directional locks can be overcome by application of manual force or can otherwise allow for deliberate extension of the associated headgear strap or portion to facilitate donning or doffing. The headgear or any portion thereof can be configured in accordance with any of the embodiments disclosed in Applicant's U.S. Publication No. 2016/0082217, U.S. application Ser. No. 14/856,193, filed Sep. 16, 2015, and PCT Publication No. WO2016/043603, the entireties of which are incorporated by reference herein.

As shown in FIG. 12, each filament extending within one of the upper side straps 202 can extend through the respective upper connector 302 and into or along the top strap 206, e.g., in an upper side strap filament storage sleeve 306. Each filament extending within one of the lower side straps 204 can extend through the respective lower connector 304 and into or along the rear section 208, e.g., in a lower side strap filament storage sleeve 308. The storage sleeves 306, 308 provide locations to store the accumulated or excess length of filaments that allow for side strap extension. In other words, the storage sleeves 306, 308 can store portions of the filaments adjacent untensioned or free ends of the filaments. These portions vary in length with adjustment of the length of the side straps 202, 204, and the excess length of filament, which is stored in the storage sleeves 306, 308 increases as the strap 202, 204 length and/or headgear size is reduced. The storage sleeves 306, 308 can also protect the filaments and help reduce jamming or snagging of the filaments during adjustment in use. The storage sleeves 306, 308 can be mounted so as to be non-obtrusive and to take up minimal additional space. The storage sleeves 306, 308 may be formed within the headgear 200 structure and therefore hidden to some extent. In the illustrated embodiment, a first end of each filament and each of the upper 202 and lower 204 side straps are permanently fixed to or relative to the mask interface 102. A second, opposite end of each of the upper 202 and lower 204 side straps, e.g., the outer braided element 332 of each of the straps, is permanently fixed to or relative to its respective connector 302, 304. A second, opposite end of each filament is not fixed to the headgear 200 such that the filament can slide or travel through its associated connector 302, 304 and control mechanism therein, storage sleeve 306, 308, and/or braided element 332 during adjustment.

Figure 26:
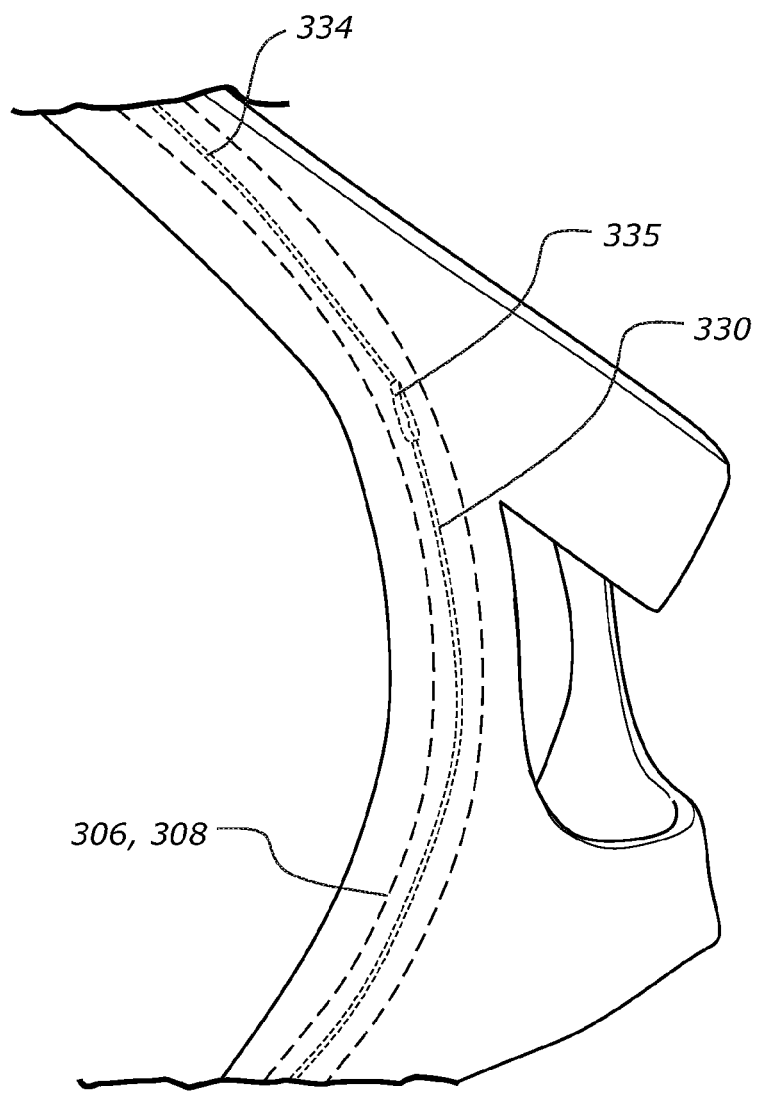
FIG. 26 shows a portion of the automatic headgear adjustment mechanism of FIG. 25A.

FIGS. 25A and 25B illustrate a schematic of the automatic headgear adjustment mechanism in an extended state and a retracted state, respectively. Further detail of mechanisms is discussed in relation to FIGS. 44A-D below. The second, opposite or "free" end of the filament 330 is connected, e.g., permanently connected, to a first end of a biasing member or elastic element 334. For example, the filament 330 can be connected to the elastic element 334 via a crimp 335 as shown in FIG. 26. A second, opposite end of the elastic element 334 is connected, e.g., permanently connected, to or relative to the storage sleeve 306, 308. To extend or length the headgear, e.g., the side straps 202, 204, the user can pull the mask interface 102 away from or relative to the headgear 200. During extension, the braided element 332 is stretched away from or relative to the connector 302, 304, pulling the filament 330 through the connector 302, 304 (and therefore the lock member(s) 336) and storage sleeve 306, 308 toward the braided element 332 (toward the left in the orientation of FIGS. 25A-25B) as shown in FIG. 25A and stretching the elastic element 334. To allow the headgear, e.g., the side straps 202, 204, to retract or shorten, the user releases the tension on the mask interface 102. The elastic element 334 then relaxes and attempts to return to its unstretched state, pulling the filament 330 through the connector 302, 304 (and therefore the lock member(s) 336) and storage sleeve 306, 308 toward and into the storage sleeve 306, 308 (toward the right in the orientation of FIGS. 25A-25B) as shown in FIG. 25B. If the automatic headgear adjustment mechanism did not include the elastic element 334 or the biasing element was located on an opposite side of the directional lock (e.g., in the braided element 332), during retraction the filament 330 would instead be pushed through the connector 302, 304, control mechanism, and/or lock member(s) 336 into the storage sleeve 306, 308, which could cause the filament 330 to buckle, bend, and/or jam in the braided element, control mechanism, or connector 302, 304. The pulling motion by the elastic element 334 in the illustrated embodiment can advantageously inhibit, reduce, or minimize bucking, bending, and/or jamming.

Figure 27A:
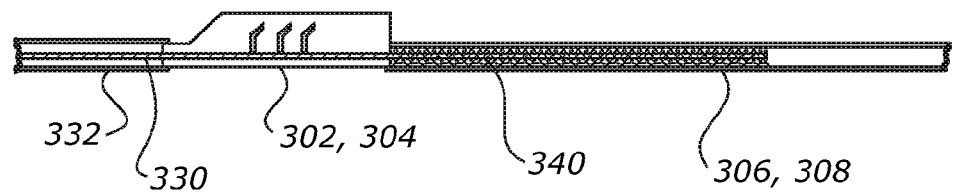
FIG. 27A shows an alternative embodiment of an automatic headgear adjustment mechanism.
Figure 27B:
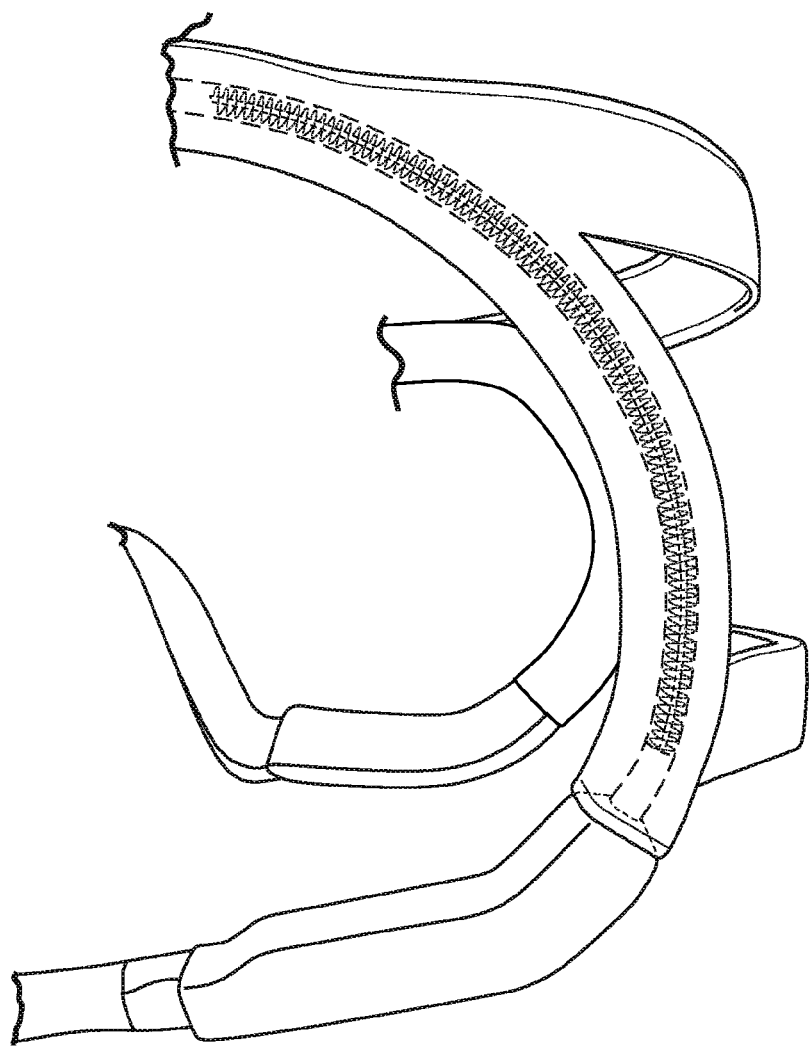
FIG. 27B shows the automatic headgear adjustment mechanism of FIG. 27A incorporated into a headgear assembly.

Instead of an elastic element 334 as shown in FIGS. 25A-25B, the automatic headgear adjustment mechanism can include a spring 340 that surrounds a portion of the filament 330 as shown in FIGS. 27A-27B. The spring can be a coiled spring, recoil spring, non-coiled spring, elastomer tube, plastic helix, or any other suitable spring. One end of the spring 340 is connected to the connector 302, 304 and/or the storage sleeve 306, 308 at or near a junction between the connector 302, 304 and the storage sleeve 306, 308. The other end of the spring 340 is connected to the filament 330, e.g., via a crimp. During extension or elongation, as the filament 330 is pulled through the connector 302, 304 and control mechanism toward the braided element 332 (toward the left in FIG. 27A) and against the resistance of the directional locks, the spring 340 is compressed. The maximum compression of the spring 340 can limit the degree or amount of extension or elongation. In some cases, the spring 340 in compression during extension can be more reliable than the elastic element 334 in tension during extension. Because the filament 330 extends within, or is connected in parallel with, the spring 340, a greater length of filament 330 can be stored in the same length of storage sleeve 306, 308 compared to embodiments including an elastic element 334 in series with the filament 330.

Figure 13A:
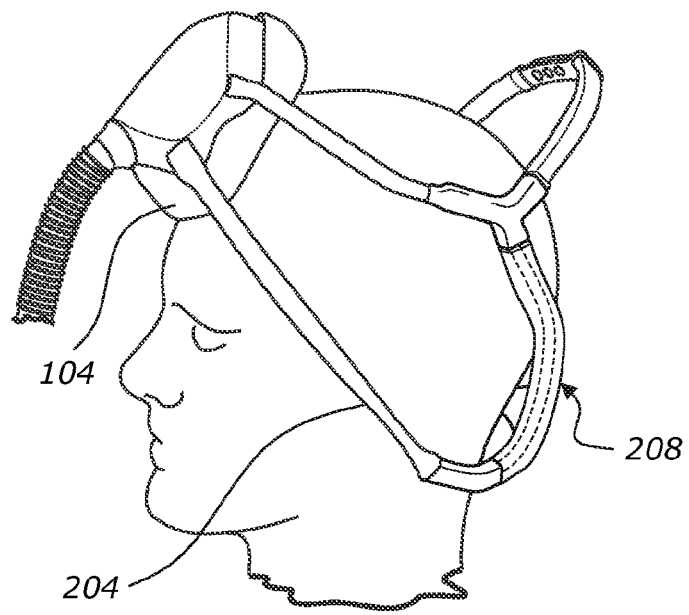
FIG. 13A shows a first stage of a donning process of the mask assembly of FIG. 1.
Figure 13B:
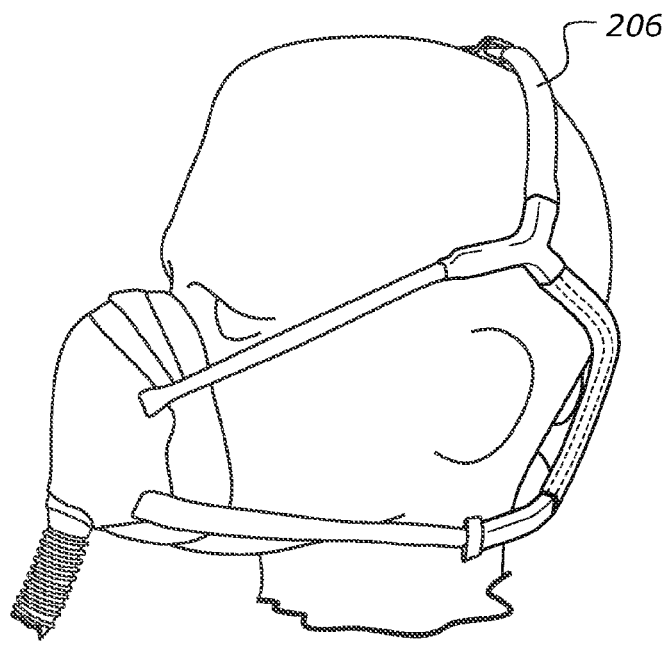
FIG. 13B shows a second stage of the donning process of the mask assembly of FIG. 1.

The mask assembly 100 of FIGS. 1-12 can be donned by the user in a two-stage process, as shown in FIGS. 13A-13B. In a first stage, shown in FIG. 13A, the user can rest the mask interface 102 on his or her forehead while moving the rear section 208 into the correct position. The user temporarily expands the lower section 212 of the rear section 208 to allow the lower side straps 204 to pass over the user's ears with reduced, minimal, or no contact with the ears. Once the lower side straps 204 have cleared the user's ears, the user returns the lower section 212 to its closed state. With the rear section 208 in place, the user lifts the mask interface 102 off of his or her forehead, pulls the mask interface 102 down to cover the nose and/or mouth, and presses the seal 104 into place. The automatically adjustable headgear mechanisms of the upper 202 and lower 204 side straps allow the side straps 202, 204 to automatically adjust and secure the mask interface 102 in the desired position. Before, during, and/or after the donning process, the top strap 206 can be manually adjusted as needed. Therefore, during donning, the top strap 206 allows for manual, macro-size adjustments to the headgear 200, the temporarily expandable rear section 208 allows the lower side straps 204 to be passed over the user's ears with reduced, minimal, or no contact, and the automatically adjustable side straps 202, 204 allow for micro-size adjustments to the headgear 200.

Figure 14:
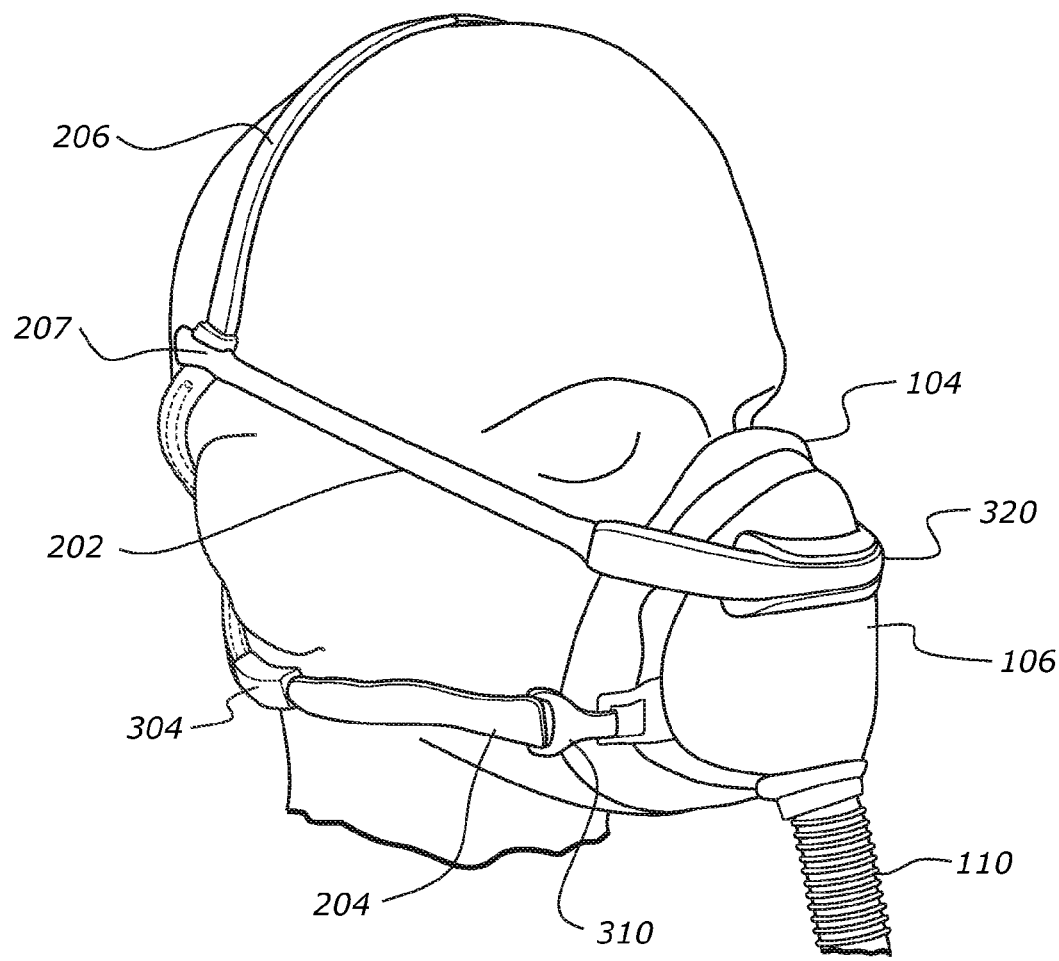
FIG. 14 is a side-front perspective view of an alternative of the mask assembly in which upper and lower side straps of the headgear assembly are removably connected to the mask interface.
Figure 15:
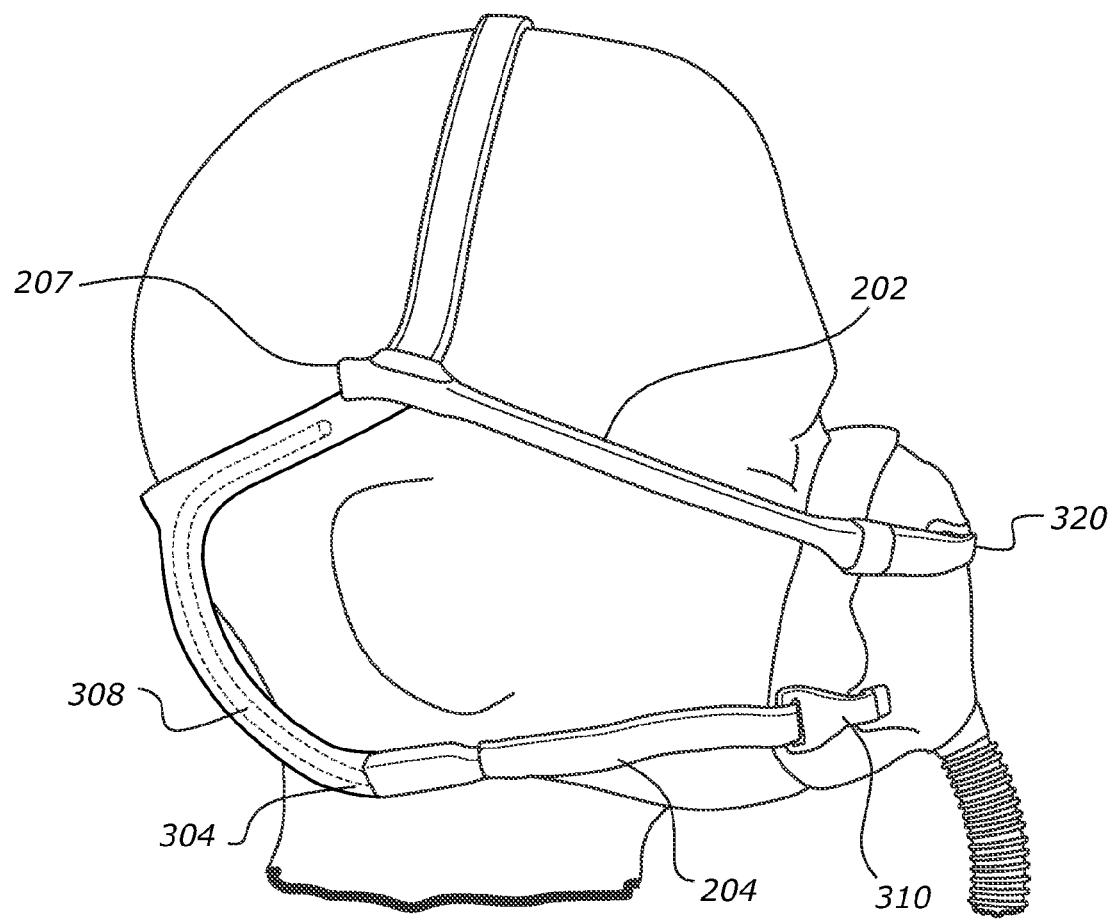
FIG. 15 is a side view of the mask assembly of FIG. 14.
Figure 16:
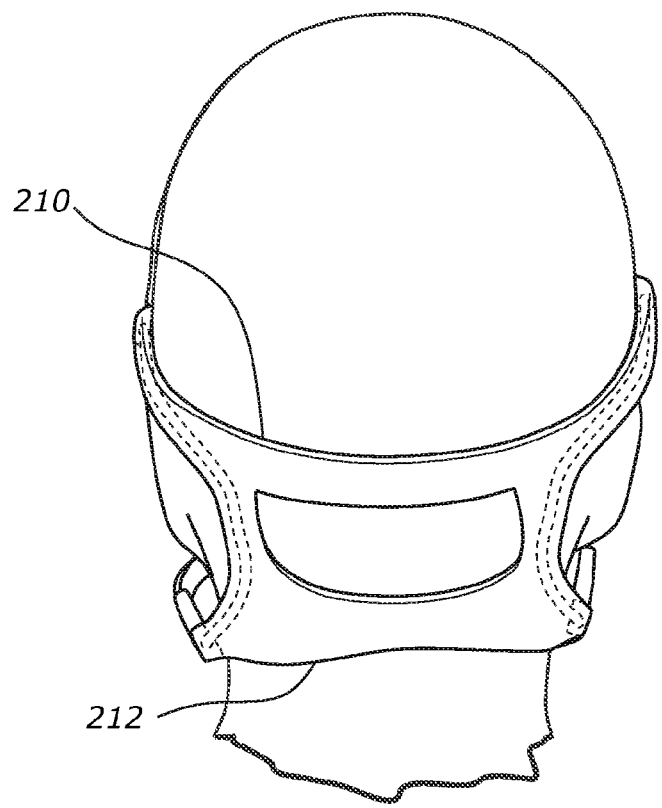
FIG. 16 is a rear view of the mask assembly of FIG. 16.

The upper 202 and/or lower 204 side straps can be removably connected to the mask interface 102. For example, any or all of the upper 202 and/or lower 204 side straps can be removably connected to the mask interface 102 via clips or hooks. FIGS. 14-16 show a variation of the mask assembly 100 in which each lower side strap 204 is removably connected to the mask interface 102, e.g., the housing 106, via a clip or hook 310. The mask assembly of FIGS. 14-16 includes a yoke 320 coupling the upper side straps 202 and the mask interface 102. As shown, one end of each of the upper side straps 202 is connected to one lateral end of the yoke 320. The opposite ends of each of the upper side straps 202 are connected, e.g., permanently connected, to the top strap 206 and/or rear section 208 at or near a junction 207 between the top strap 206 and rear section 208. The yoke 320 is removably connected to the housing 106 in use. The removable connections between the clips or hooks 310 and the mask interface 102 and between the yoke 320 and the mask interface 102 advantageously allow the mask interface to be completely separated from the headgear assembly 200.

As shown, the yoke 320 can extend across part or all of a width of the housing 106. The yoke 320 can be secured to the housing 106 in use via, for example, a snap-fit, interference fit, or any other appropriate means. The upper side strap filaments of the automatically adjustable headgear mechanisms can extend into and be stored in the yoke 320. As the accumulated upper side strap filaments are stored in the yoke 320, the headgear 200 may omit upper strap filament storage sleeve 306. In the illustrated embodiment, the headgear 200 does not include the upper connectors 302. Instead, the yoke 320 houses the directional locks or lock members. The yoke 320 can house one or more directional locks or lock members at or proximate a first lateral end of the yoke 320 and configured to receive one of the upper side strap filaments, and one or more directional locks or lock members at or proximate a second, opposite lateral end of the yoke 320 and configured to receive the other of the upper side strap filaments. A magnitude of the length adjustment allowed within the upper straps 202 can be different (e.g., less than) a magnitude of the length adjustment allowed within the lower straps 204.

Figure 17:
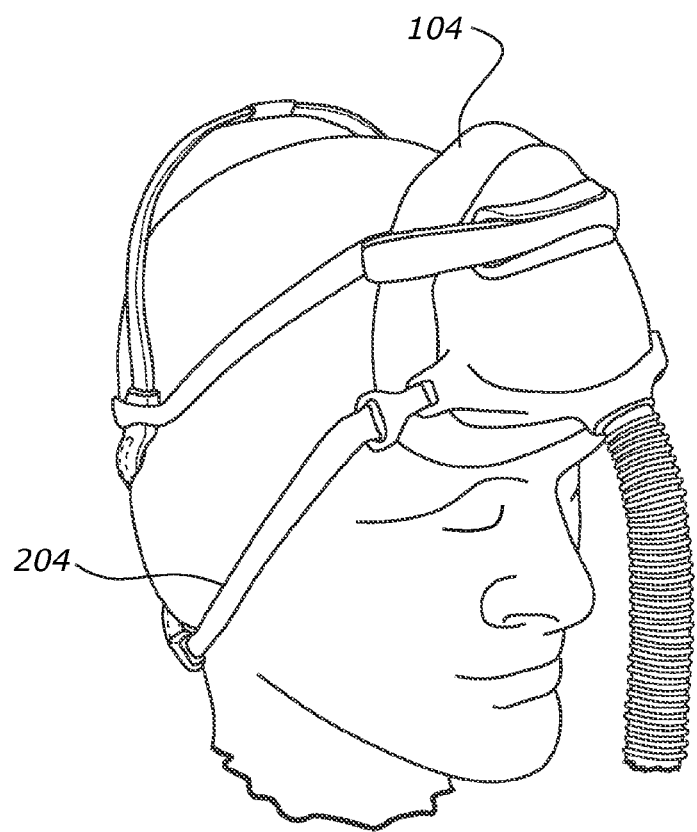
FIG. 17 shows a first stage of a donning process of the mask assembly of FIG. 14.
Figure 18:
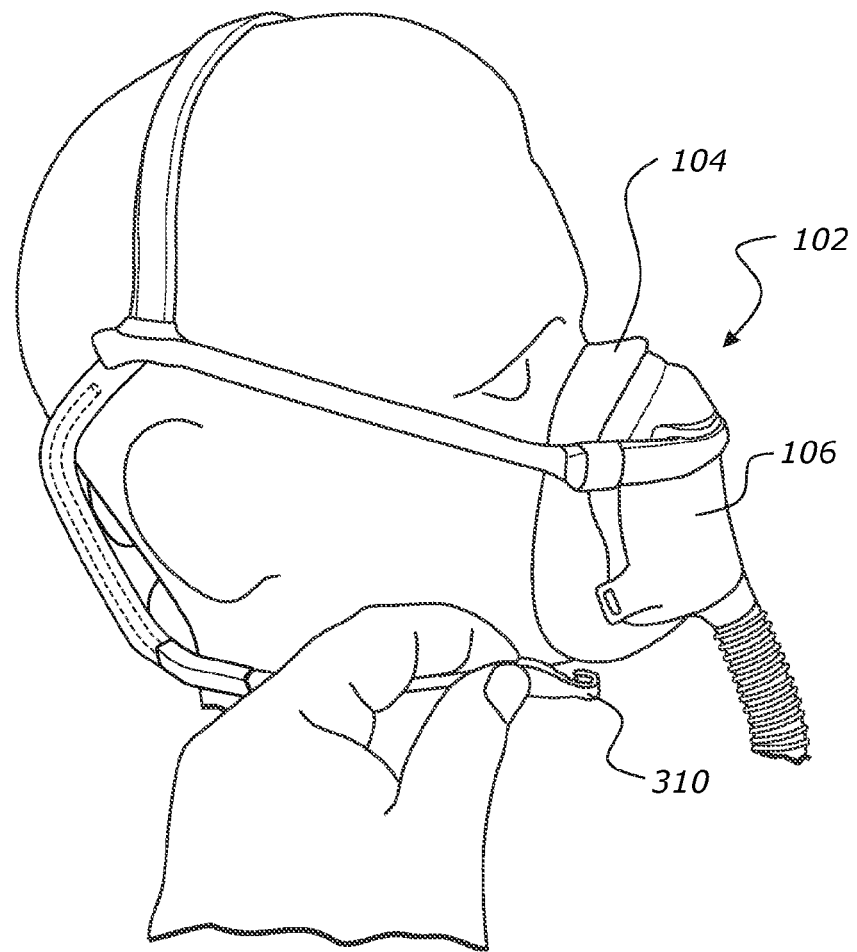
FIG. 18 is a side view of a stage of an alternative donning process of the mask assembly of FIG. 14.

The mask assembly of FIGS. 14-16 can be donned by the user via a two-stage process, as shown in and described with respect to FIGS. 13A-13B. FIG. 17 illustrates the mask assembly following the first stage, with the seal 104 resting on the user's forehead and the lower side straps 204 positioned below the user's ears. Alternatively, the mask assembly of FIGS. 14-16 can be donned in a three-stage process due to the removably connected lower side straps 204. In a first stage, with the clips 310 of the lower side straps 204 disconnected from the mask interface 102 as shown in FIG. 18, the headgear 200 can be slid or pulled down on top of the head, similar to donning a baseball cap. In a second stage, the pulls the mask interface 102 down to cover the nose and/or mouth, and presses the seal 104 into place. In a third stage, the user connects the clips 310 of the lower side straps 204 to the mask interface 102, e.g., the housing 106 and makes any final adjustments needed to move the seal 104 into the desired position. The automatically adjustable headgear mechanisms of the upper 202 and lower 204 side straps allow the side straps 202, 204 to automatically adjust and secure the mask interface 102 in the desired position.

FIGS. 31-34B illustrate an embodiment of a mask assembly including a mask interface 102 and a frame 620. The frame 620 can function similarly to the yoke 320 of FIGS. 14-18 in some respects. The mask assembly also includes headgear, such as headgear 200. The frame 620 is removably coupled to the mask interface 102, e.g., the housing 106. The frame 620 couples one or more components of the headgear 200 to the mask interface 102. For example, the frame 620 can include two upper strap connection locations 622 as shown. One of the upper side straps 202 can be coupled, permanently or removably, to each of the upper strap connection locations 622. The frame 620 can also or alternatively include two lower strap connection locations 624 one for each of the lower side straps 204. In the illustrated embodiment, each of the lower strap connection locations 624 receives a clip or hook 310 coupled to one of the lower side straps 204 to removably couple the lower side straps 204 to the frame 620. The frame 620 can therefore allow the headgear 200 to be completely separated from the mask interface 102 as needed or desired.

Figure 32:
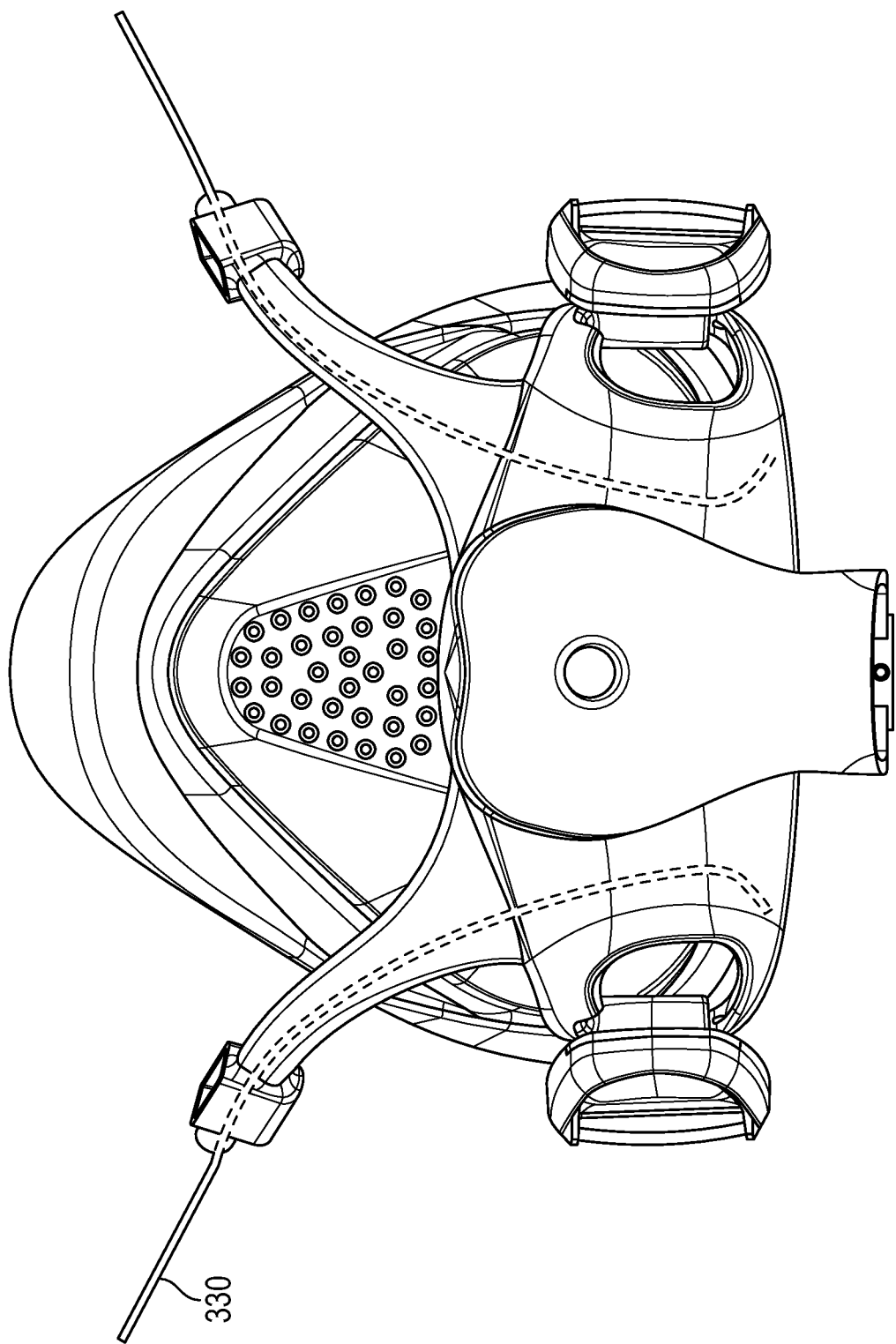
FIG. 32 shows paths for filaments of automatically adjustable headgear mechanisms extending through the frame of FIG. 31.
Figure 33:
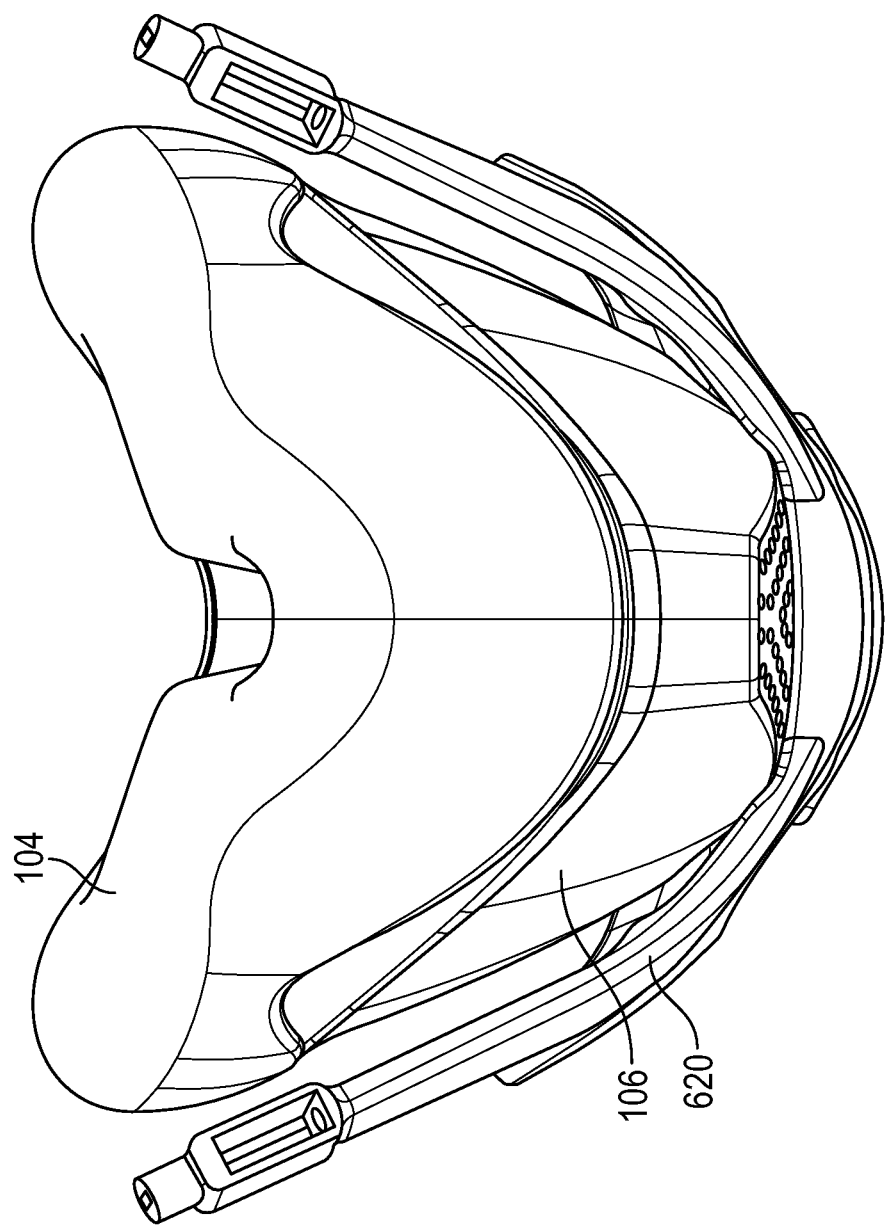
FIG. 33 shows a top view of the mask assembly of FIG. 31.

Similar to the yoke 320, the frame 620 houses the control mechanisms, e.g., directional locks, associated with the automatically adjustable headgear mechanisms of the upper side straps and accommodate the upper side strap filaments 330. Examples of such an automatically adjusting headgear mechanism are discussed in relation to FIGS. 44A-D below. The control mechanisms are disposed proximate the upper side strap connection locations 622, for example, in the control mechanism housing portions 626 shown in FIG. 31. The filaments 330 can extend, be stored, and/or move within channels extending within or internally through the frame 620, such as described below in relation to FIGS. 35 to 42. For example, FIG. 32 illustrates possible paths for the filaments 330. Storing the filaments 330 within separate channels within the frame 620 can help isolate the filaments 330 from each other to prevent or inhibit the filaments 330 from interfering with each other. Storing the filaments 330 in the frame 620 can help hide the filament 330 storage from view at least to some extent and can help improve the aesthetic appeal of the mask assembly. Storing the filaments 330 within the frame 620 also utilizes existing space within the mask assembly and can therefore enable the size of the mask assembly to be reduced.

Figure 34B:
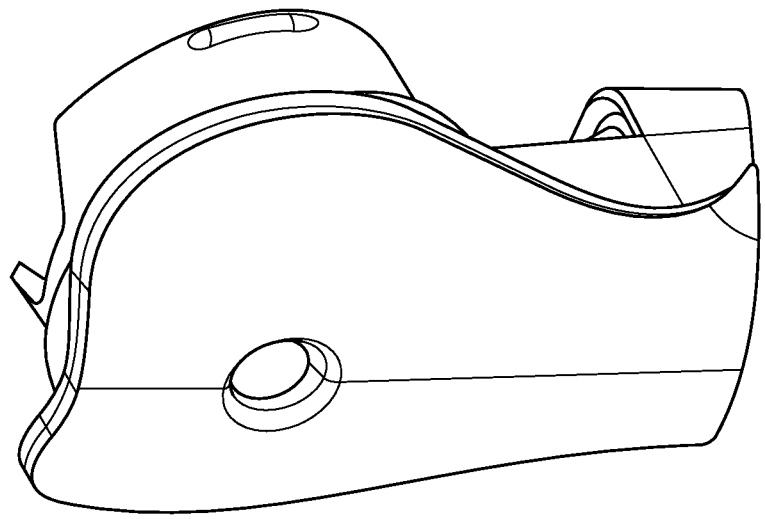
FIG. 34B shows a front side perspective view of the elbow of FIG. 34A.
Figure 34A:
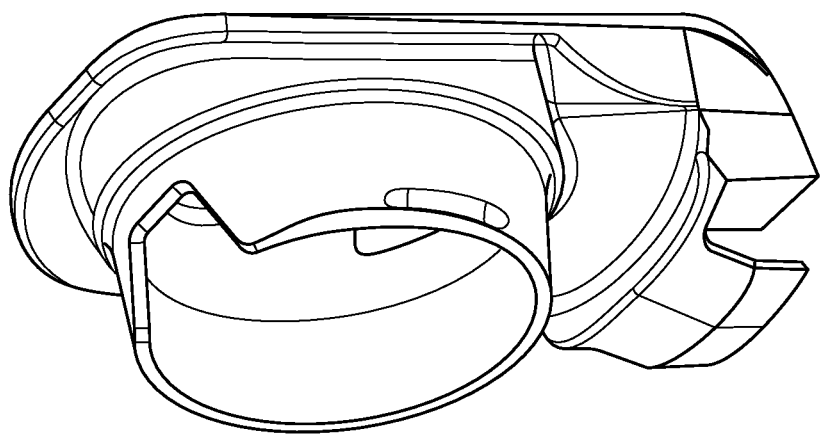
FIG. 34A shows a rear side perspective view of an elbow of the mask assembly of FIG. 31.
Figure 35:
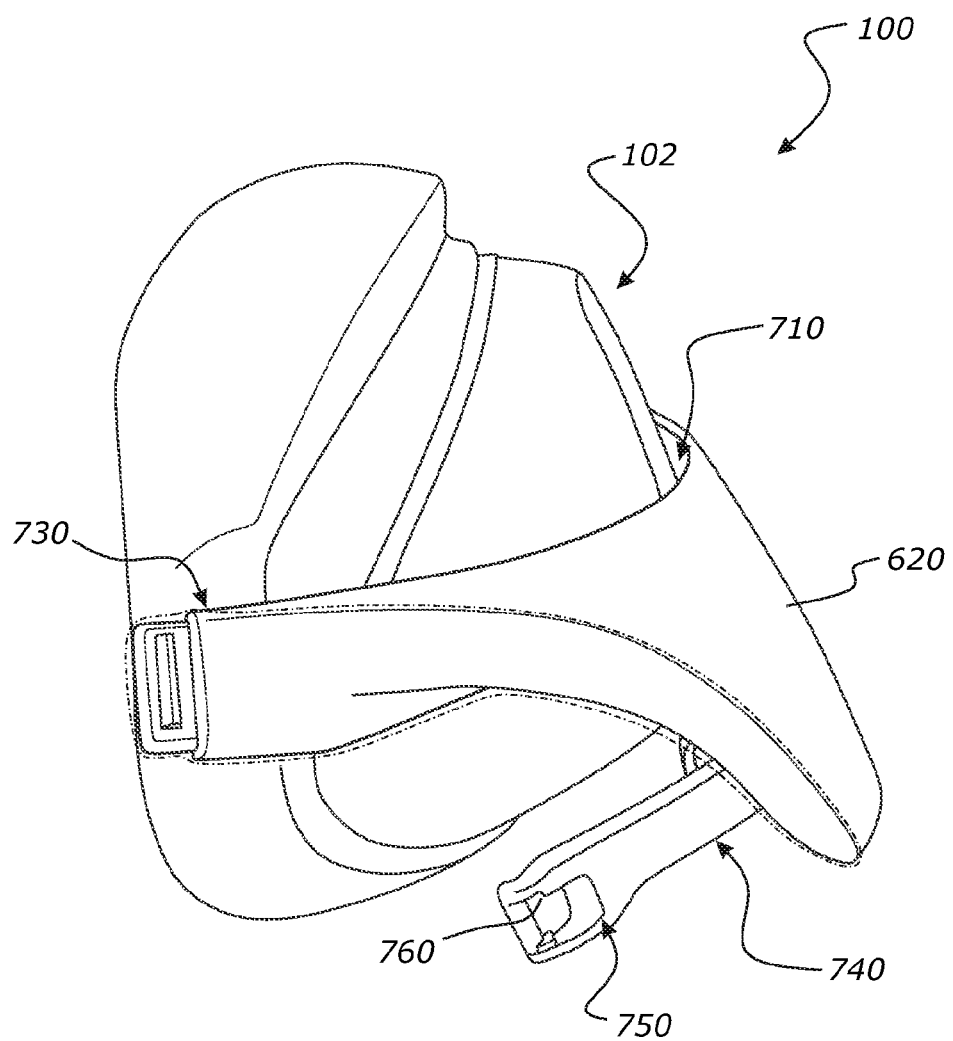
FIG. 35 shown a front perspective view of an alternative embodiment of a mask assembly including a removable frame.

In some embodiments, an elbow 630, shown in FIGS. 34A-34B, is coupled to the mask assembly such that the frame 620 is positioned or sandwiched between the elbow 630 and housing 106. The elbow 630 removably couples to the housing 106 through and aperture in the frame 620, which removably secures the frame 620 in place. A gas supply conduit is coupled to the elbow 630 to deliver gases to the mask interface 102 in use.

FIGS. 35-43 illustrate an embodiment of a mask assembly 100 comprising a mask interface 102 and a frame 620. As described for earlier embodiments, the mask assembly can be used in conjunction with headgear, for example headgear described herein. The frame 620 is removably coupled to the mask interface 102, e.g., the housing 106. The frame 620 can therefore allow headgear to be completely separated from the mask interface 102 as needed or desired.

Frame 620 comprises two upper headgear connector arms 730 and two lower headgear connector arms 740. An upper side strap of a headgear can be coupled, permanently or removably, to each of the upper arms 730 and a lower side strap of a headgear can be coupled, permanently or removably, to each of the lower arms 740.

Upper arms 730 and lower arms 740 are integral with and extend from a central portion of the frame 620. Each arm comprises a distal end spaced away from frame 620. Upper arms 730 and/or lower arms 740 may comprise a slot or hole 750 to fit and interact with a headgear strap or a headgear connector clip or hook of an upper side strap or lower side strap respectively, to couple the headgear to the frame 620. The clip or hook may be connected to the upper and/or lower side straps by any suitable means, for example by any of the means described herein. In some embodiments the clip or hook may be connected to the strap by over-moulding. Slot or hole 750 may be located at or near the distal end of each arm 730/740. In the illustrated embodiment, lower arms 740 comprise a slot or hole 750 to fit and interact with a strap, connector clip or hook of a lower side strap of a headgear. In some embodiments the slot or hole 750 comprises one or more notches 760. The notches 760 may facilitate coupling between the headgear and the frame 620. For example, when an upwards force is applied to the headgear or clip, the clip will contact the edge of the notch 760 that will act as a "stop bump" to stop rotation of clip. This action of the notch edge will limit any further rotation and reduce or minimize the likelihood of the clip becoming detached from the post.

Frame 620 is generally quadrilateral in shape. The frame 620 comprises a front surface 840 and a rear surface 850, each having upper, lower and side edges. Rear surface 850 faces mask interface 102 and is provided with a connection for mask interface 102. The front surface 840 faces away from the mask interface 102 and has upper edge 710, side edges 720, and lower edge 722. Upper arms 730 extend from the upper corners of frame 620, as defined by upper edge 710 and side edges 720. Upper arms 730 each comprise at least one forward surface 732 that is continuous with front surface 840, a first side that is continuous with upper edge 710 and a second side that is continuous with side edge 720. Lower arms 740 extend from rear surface 850 of the frame. The lower arms 740 are upwardly spaced from the lower edge 722 of the frame 620.

The upper edge 710 and each of the side edges 720 of the frame 620 each follow continuous arcs. The lower edge 722 is substantially linear. By "continuous arc" it is meant that the edge forms part of a curve, which gradually and consistently deviates from being a straight line along its length. For example, a continuous arc may form part of the circumference of a circle.

In the illustrated embodiment the two upper arms 730 are wider and thicker than the two lower arms 740. In some embodiments, each of the upper arms 730 and/or lower arms 740 may curve along their length. In some embodiments the horizontal thickness and/or vertical width of each of the upper arms 730 and lower arms 740 may be substantially constant along their length. Alternatively, each of the upper arms 730 and/or lower arms 740 may have a variable thickness or width along their length. For example, either the thickness or the width or both the thickness and the width of each upper arm and/or each lower arm 740 may taper, by reducing along their length. This tapering may be a substantially linear fashion as the distance along the length of the arm from the frame 620 increases.

As described herein, in various embodiments a gas delivery conduit delivers gases to mask interface 102. The frame 620 incorporates a gas path 630. The gas path 630 can be removably and/or permanently attached to housing 106. Gas path 630 may comprise an anti-asphyxia valve.

The front surface 840 of the frame 620 is convex and the rear surface 850 is concave. The gas path 630 is positioned within a space defined by a portion of the rear concave surface 850 of the frame 620. The gas path 630 extends rearwardly from the rear surface of the frame. The gas path 630 may be attached to the rear surface 850 of the frame 620 or may be integrally formed with the rear surface 850 of the frame 620. For example, the frame 620 and the gas path 630 may be integrated to form a single component. In the illustrated embodiment, the gas path 630 is provided to the rear surface 850 of the frame 620 such that the frame 620 and the gas path 630 form a single component. Such an arrangement provides a frame 620 comprising a curved front surface 840 that is substantially smooth. By "smooth" it is meant that the curved surface is continuous and without indentations, raised areas or protrusions, for example without a protruding elbow.

Gas path 630 comprises a first collar 860 and a second collar 870, each of the first and second collars 860/870 comprising a bore defining a central axis. Each of the collars are generally annular or oval in shape. The first collar 860 is oriented such that a central axis defined by the bore of the first collar 860 is orthogonal to the rear surface 850 of the frame 620. In some embodiments, the central axis defined by the bore of the first collar 860 is oriented at 70 to 110 degrees to the rear surface 850 of the frame 620. The second collar 870 is oriented such that a central axis defined by the bore of the second collar 870 is substantially parallel to the rear surface 850 of the frame 620. The second collar is also oriented such that the central axis of its bore is orthogonal to the central axis defined by the bore of the first collar 860, preferably at 70 to 110 degrees to the central axis defined by bore of the first collar 860. Collars 860/870 are in fluid communication to form gas path 630. A gas delivery conduit connects to second collar 870, for supply of gas to mask interface 102. The first collar 860 is configured to connect to the housing 106 so that the gas path 630 of the frame is in fluid communication with the housing 106. First collar 860 extends from rear surface 850 at a point equidistant between upper arms 730 and lower arms 740. Each lower arm 740 extends from rear surface 850 adjacent gas path 630, at, adjacent or spaced from collar 870.

Figure 36A:
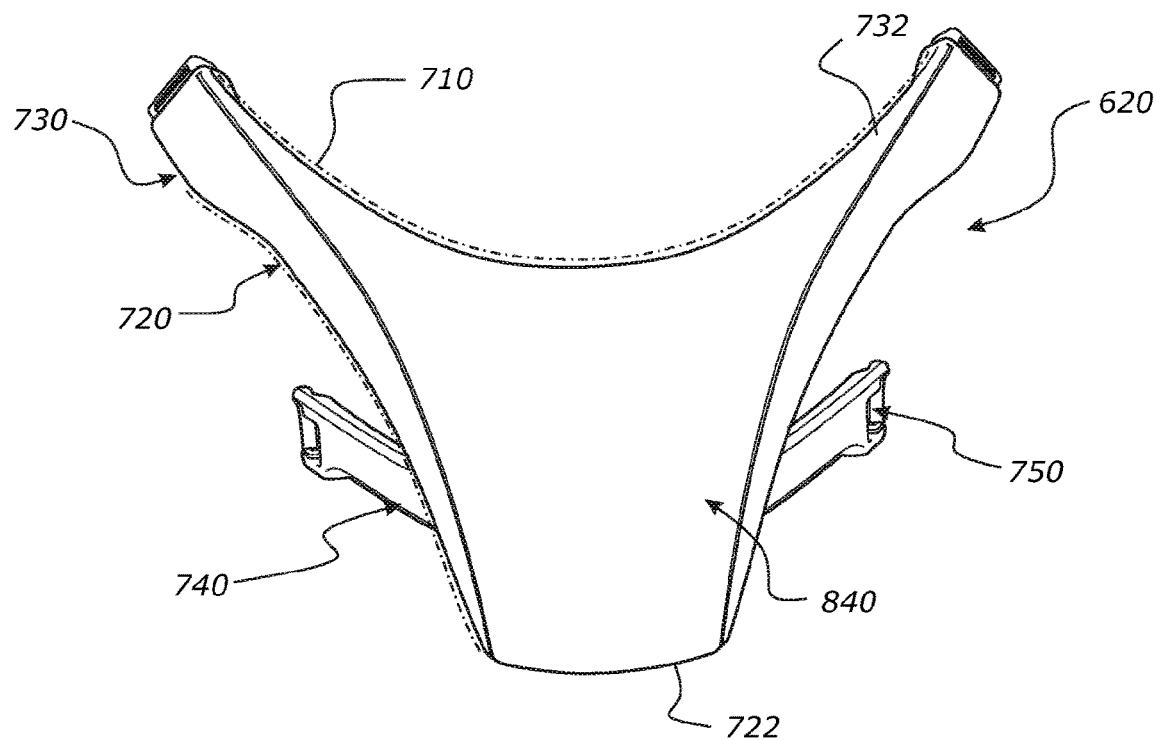
FIGS. 36a and 36b show front and side perspective views of the frame of the mask assembly of FIG. 35 respectively.
Figure 36B:
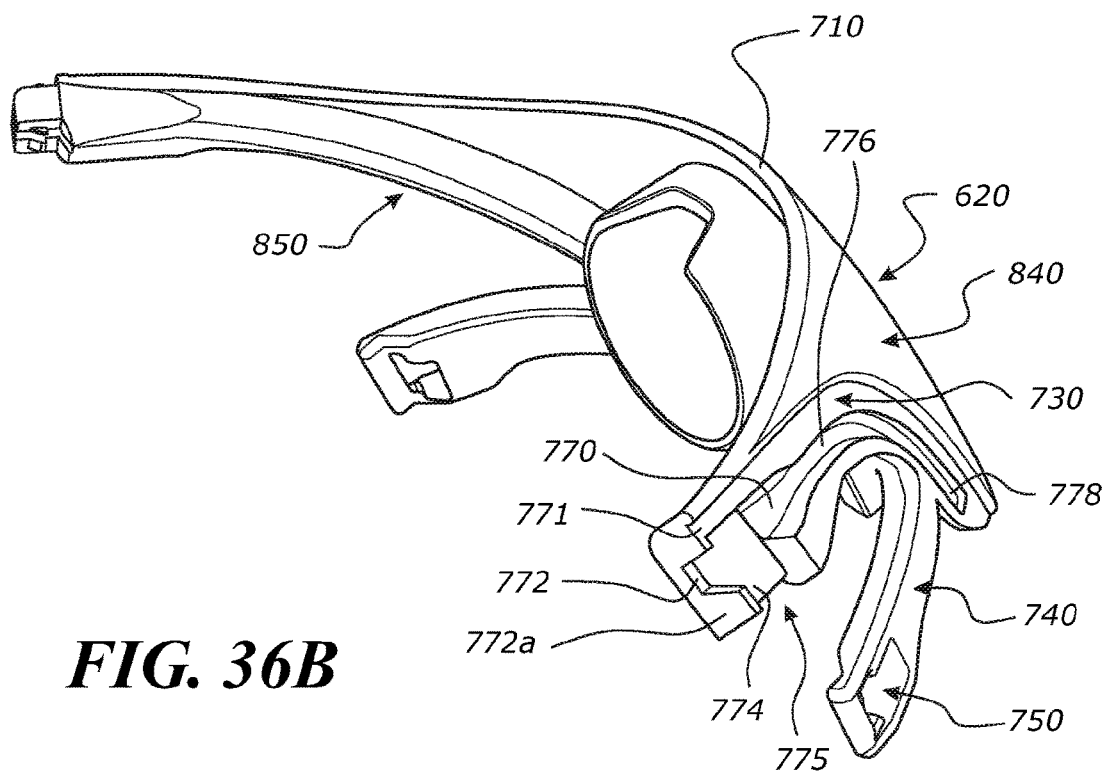
Figure 37:
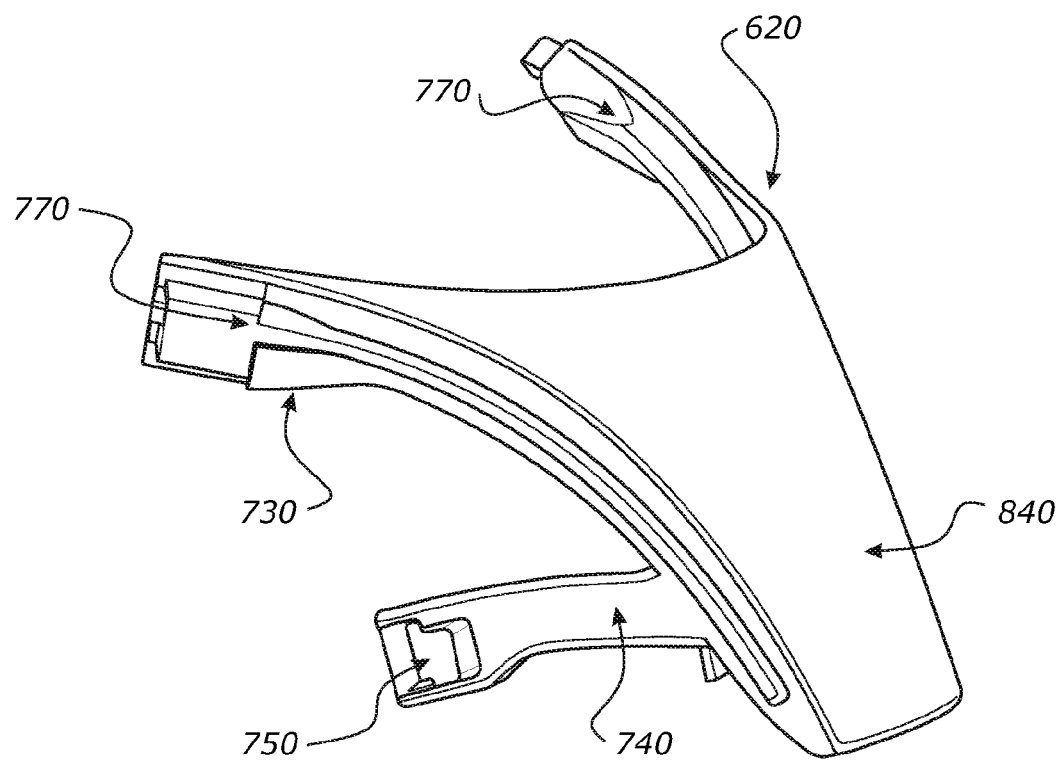
FIG. 37 shows a front side perspective view of the frame of the mask assembly of FIG. 35.
Figure 38A:
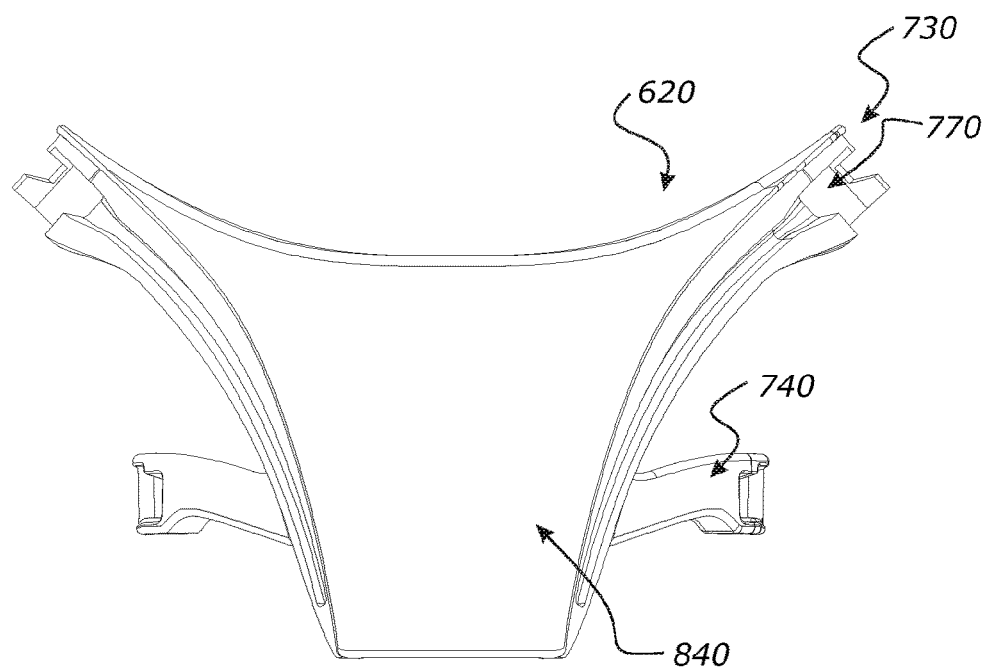
FIGS. 38A-38D show various perspective views of the frame of FIG. 35 comprising insert recesses formed in the frame.
Figure 38B:
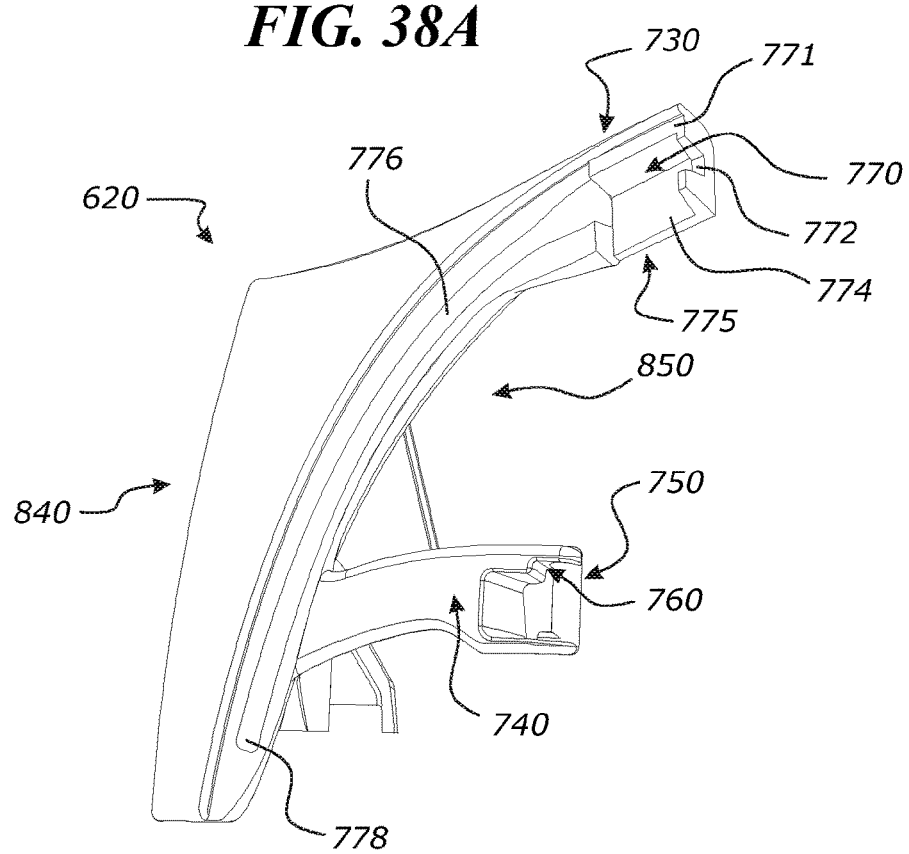
Figure 38C:
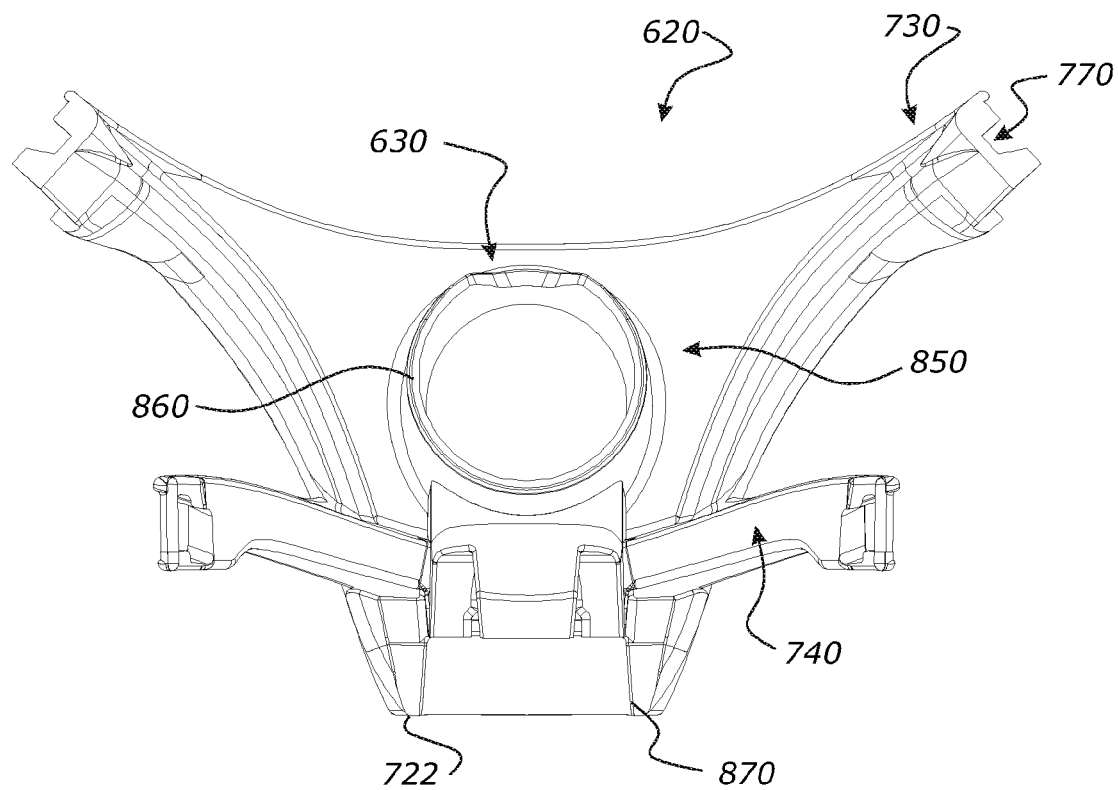
Figure 38D:
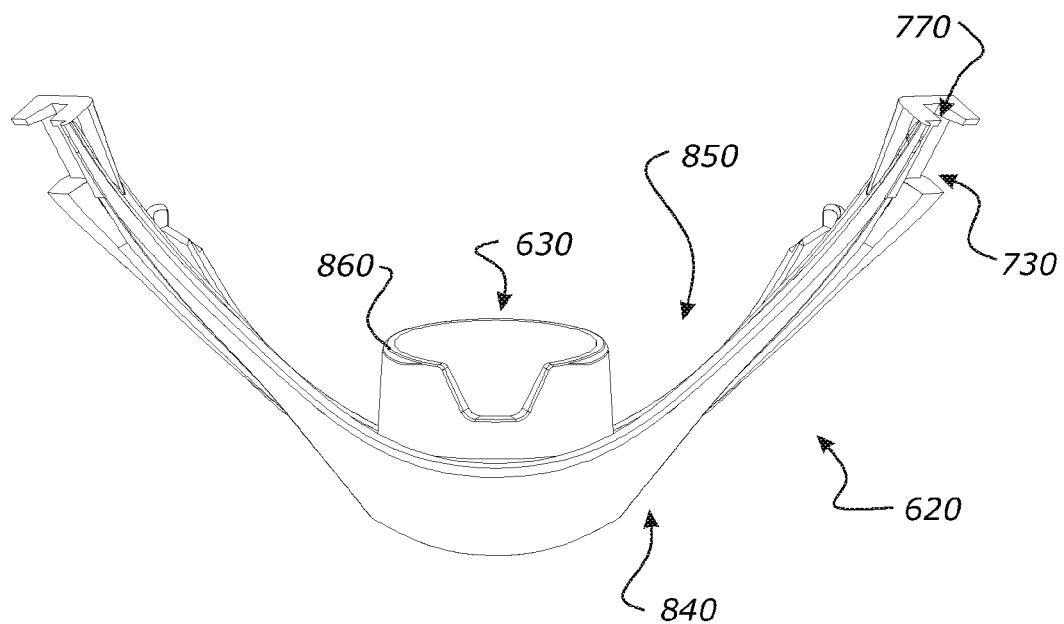

Frame 620 may comprise insert recesses 770 that house automatically adjusting headgear mechanisms and their associated components, as described herein. In various embodiments each insert recess 770 may be formed in the front surface 840 of frame 620. For example, each insert recess 770 may house a control mechanism and associated filament of one automatically adjusting headgear mechanism. The control mechanism can include one or more lock mechanisms, for example, directional locks, as described herein. Insert recesses 770 comprise shelf 771, mouth 772, chamber 774, and channel 776 that terminates at blind end 778. Mouth 772 and chamber 774 are located at the distal ends of upper arms 730 and are at least partly defined by wall 772a. Chamber 774 may comprise an opening 775 along its lower edge. When assembled, the filament of an automatically adjusting headgear mechanism extends from a headgear strap or clip into insert recess 770 through mouth 772. The filament passes through chamber 774 and an automatically adjusting headgear mechanism housed within chamber 774, and terminates in channel 776. In use, the filament can move longitudinally within insert recess 770, with a free end of the filament able to move towards and away from blind end 778, as dictated by the motion of the headgear and operation of the automatically adjusting headgear mechanism. Channels 776 provide locations to store the excess length of filaments that allow for headgear extension. In other words, channels 776 operate in a similar fashion to storage sleeves described herein and can store portions of the filaments untensioned or free ends of the filaments. These filament portions vary in length with adjustment of the length of headgear straps, and the excess length of filament, which is stored in the channels 776 increases as the length of headgear straps and/or headgear size is reduced. The channels 776 can also protect the filaments and help reduce jamming or snagging of the filaments during adjustment in use. The channels 776 extend within or internally through the frame 620, along each side 720 of the frame 620. Each insert recess 770 may extend along the side edge of the frame 620. However, in other embodiments, the insert recess 770 may be spaced inwardly from the side edge. Each of the insert recesses 770 has a width that varies along the length of the insert recesses 770. For example, there may be an inverse relationship between the width of the insert recess 770 and distance from the top edge 710 of the frame 620. In other embodiments each of the insert recesses 770 may have a width that is substantially constant along the length of the insert recesses 770. In FIG. 36B, channel 776 is flared to provide a first width where it joins chamber 774, tapers to a second width at an intermediate point spaced from chamber 774, and then remains of constant width from the intermediate point to blind end 778. Insert recesses 770 have a generally U-shaped cross-section, with a flat bottom surface, but may alternatively be V-shaped or have a curved bottom surface.

Figure 39A:
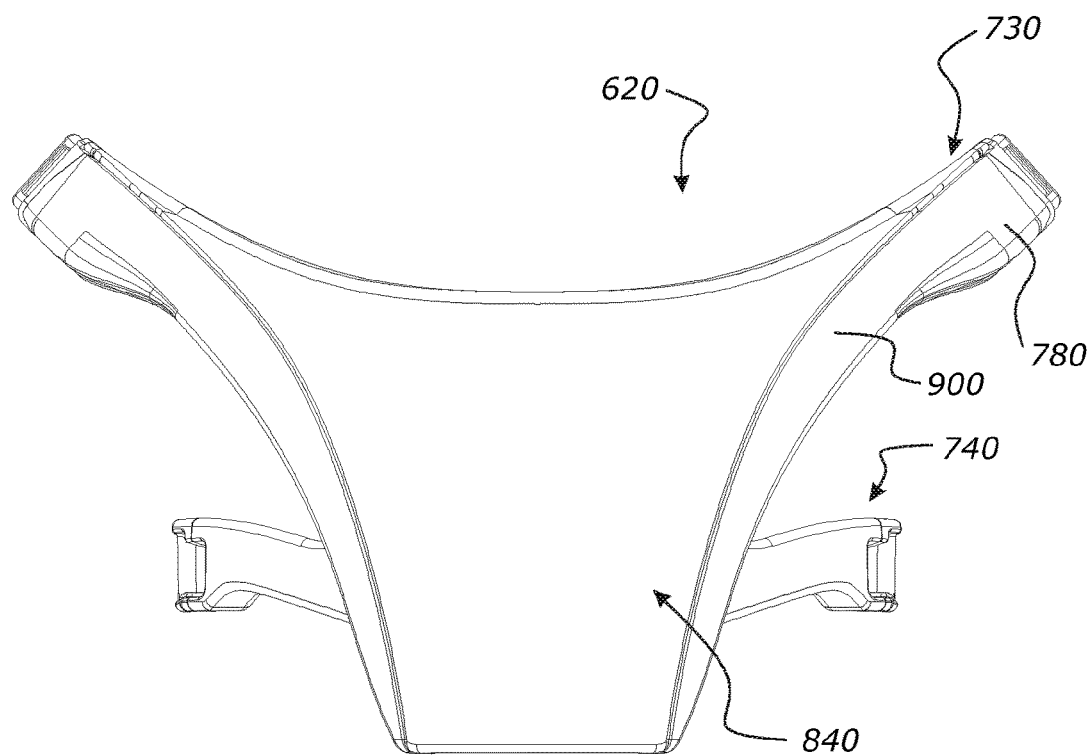
FIGS. 39A-39C show perspective views of the frame corresponding to the views of FIGS. 38A-38C respectively with the insert recesses enclosed by inserts.
Figure 39B:
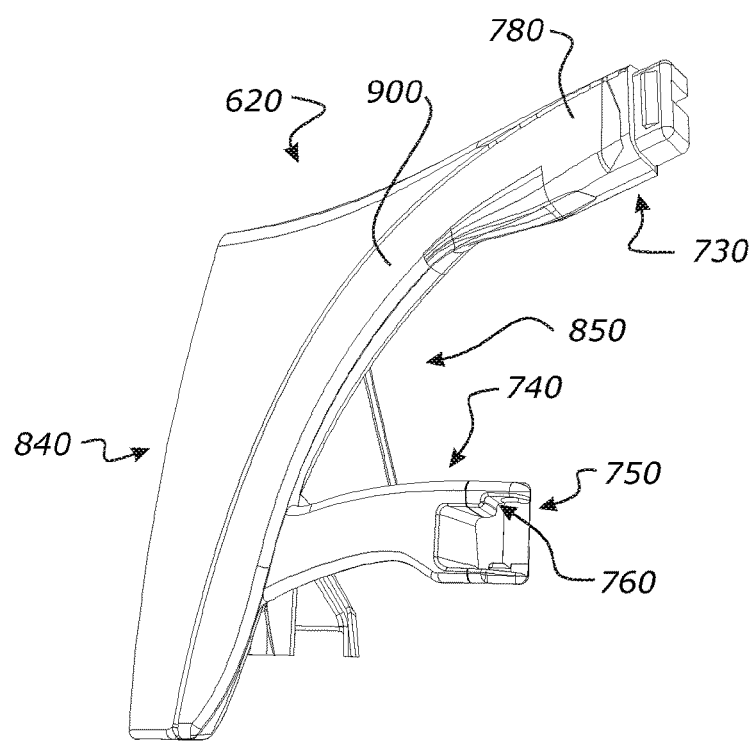
Figure 39C:
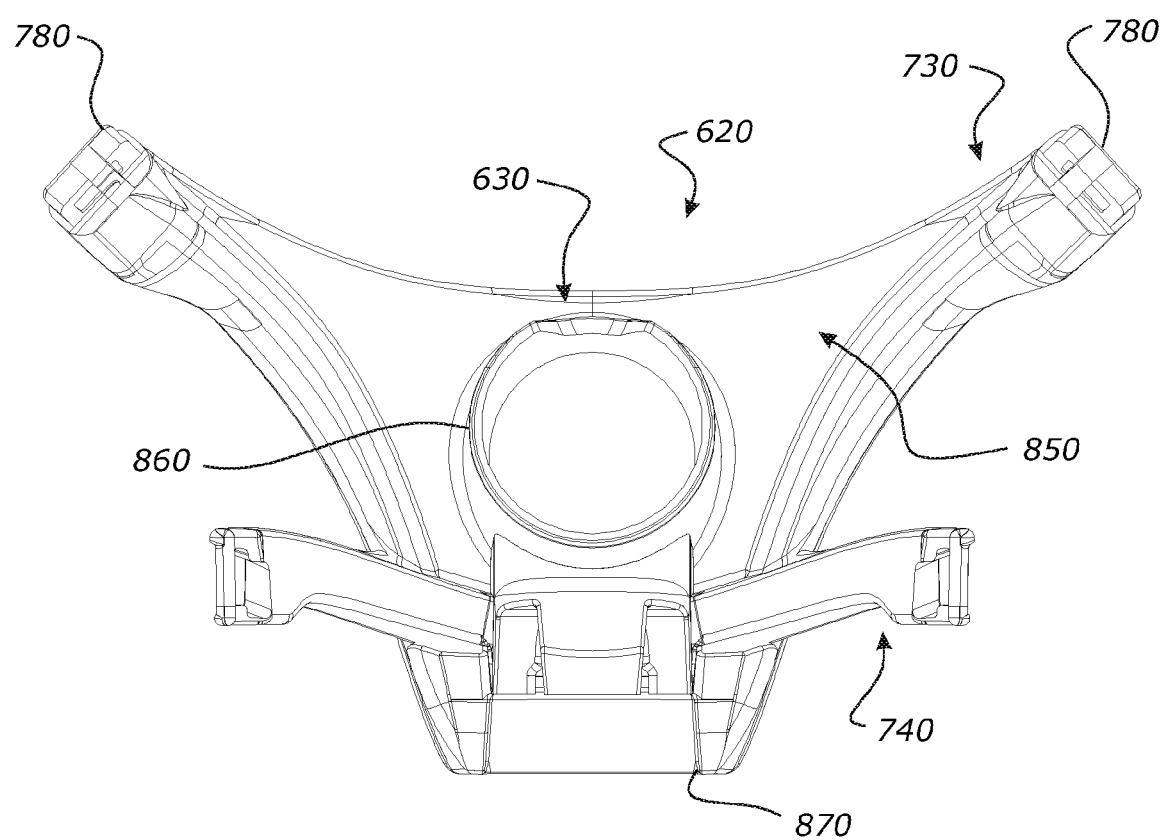
Figure 40:
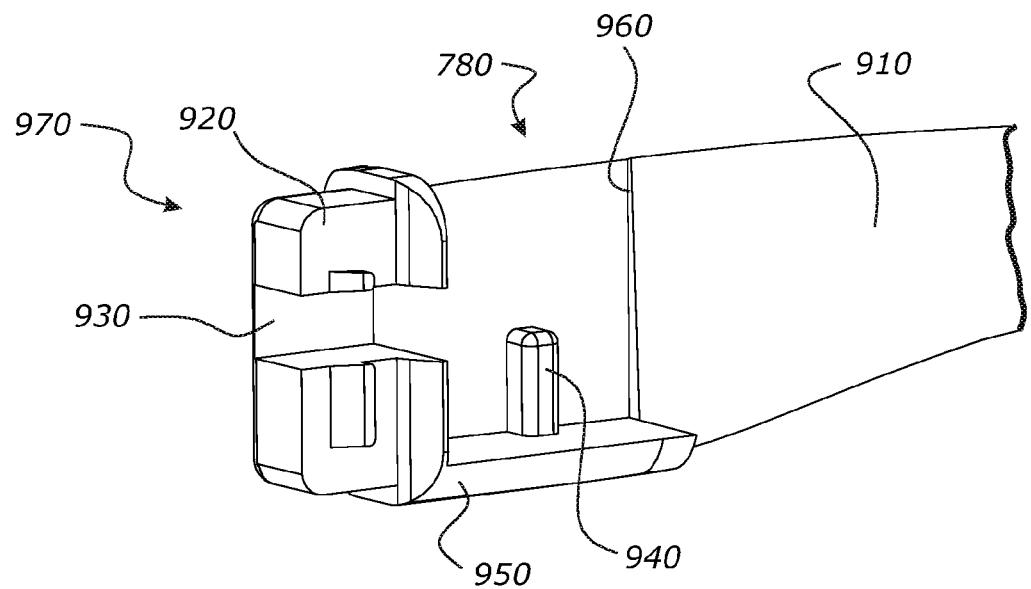
FIG. 40 shows a perspective view of a portion of the insert of FIGS. 38A-38C comprising an alignment feature.
Figure 41:
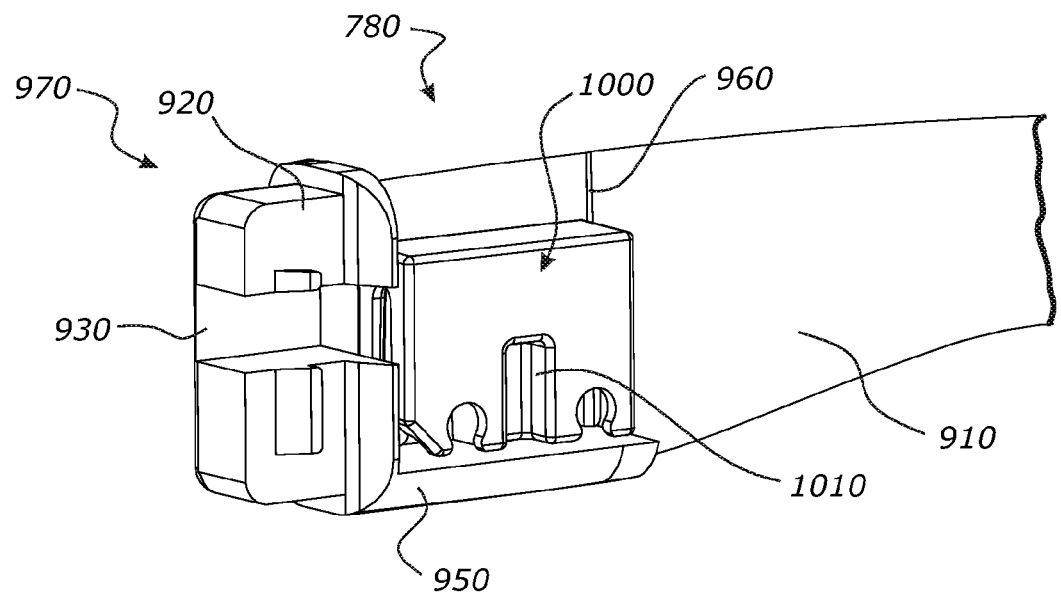
FIG. 41 shows a perspective view of the insert of FIG. 40 comprising a housing of an automatically adjusting headgear mechanism.
Figure 42:
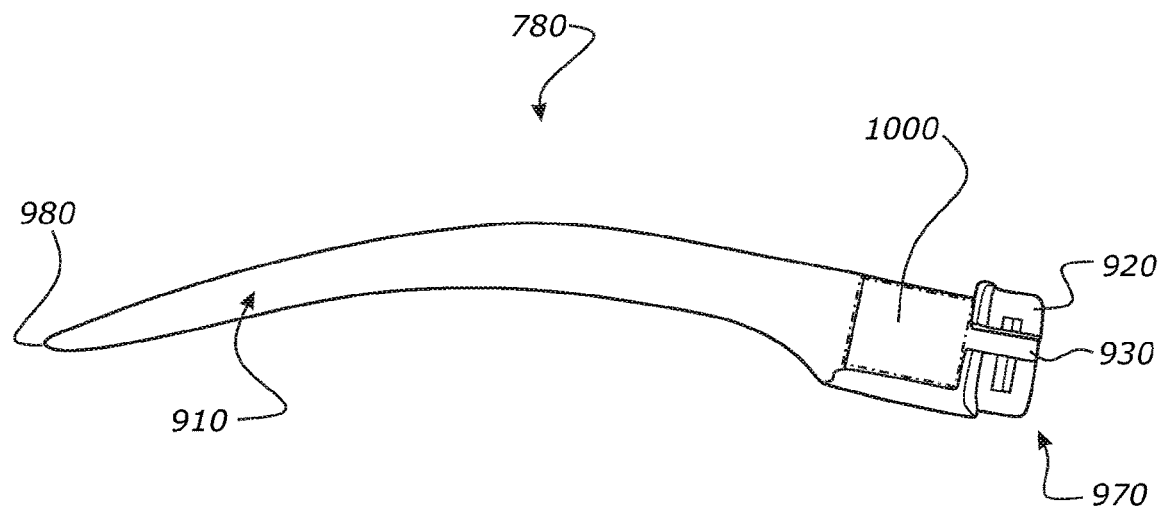
FIG. 42 shows a rear perspective view of the insert for the left insert recess of FIGS. 38A-38D with the dotted box denoting the location of a housing of an automatically adjusting headgear mechanism.
Figure 43:
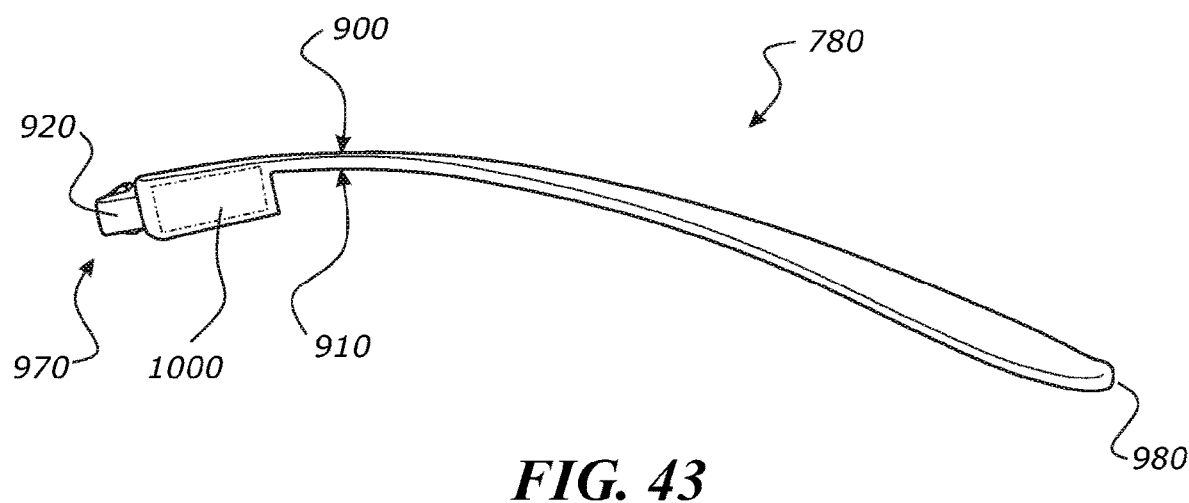
FIG. 43 shows a front perspective view of the insert for the left insert recess of FIGS. 38A-38D with the dotted box denoting the location of a housing of an automatically adjusting headgear mechanism in the insert.

Shelf 771 comprises a shelf, or ledge, or ridge extending along or surrounding at least a portion of each insert recess 770, which may extend entirely along a longitudinal edge or both longitudinal edges of, or fully surround insert recess 770. An insert 780 may be inserted into each insert recess 770, as shown in FIGS. 39A to 39C, engaging at least shelf 771 and providing a cover that forms an enclosed space within insert recess 770. The configuration of insert recess 770 and insert 780 allows frame 620 to provide chamber 774 and channel 776 as an enclosed space. It would be technically challenging to manufacture chamber 774 and channel 776 as an enclosed space in frame 620 in a single shot moulding process. Insert 780 may be attached post manufacture by techniques known in the art, such as for example by interference fit, gluing, over-moulding, welding or otherwise attaching insert 780 to frame 620, to or within shelf 771. In some embodiments insert 780 may be attached permanently, for example by welding. In other embodiments insert 780 may be removably attached.

Referring to FIGS. 40 to 43, insert 780 may carry an automatically adjusting headgear mechanism 1000 as described herein, with or without its associated filament, and orient the mechanism 1000 and associated filament for operation within chamber 774. Insert 780 comprises front surface 900, rear surface 910, optional over-moulding or strap material attachment feature 920, filament passage 930, alignment feature 940, lower lip 950, and inner lip 960. The location of the housing of automatically adjusting headgear mechanism 1000 in insert 780 is shown by a dotted box in FIGS. 42 and 43. The rear surface 910 faces the frame 620 and at least a portion of rear surface 910 engages shelf 771 such that the enclosed space is formed. The front surface 900 of the insert 780 faces away from the insert recess 770. The front surface 900 of the insert 780 may be configured to follow the contours of the frame 620 to provide a substantially smooth front surface 840 of the frame 620 when the frame 620 and the insert 780 are assembled. When assembled, filament passage 930 aligns with mouth 772 of insert recess 770.

The insert 780 has a shape, including a thickness, a length and a width substantially corresponding to the shape, including the depth, the length and/or the width of, and sufficient to cover insert recess 770 such that the enclosed space is formed. In some embodiments the shape including the thickness, length and width of insert 780, particularly of front surface 900 and rear surface 910 will correspond to the shape and proportions, including the depth, width and length of shelf 771.

As described above, rear surface 910 of insert 780 faces insert recess 770 and may be substantially smooth. Such an arrangement may provide for a smooth passage of the filament through the insert recess 770. Rear surface 910 may comprise alignment feature 940 in a position and orientation such that when insert 780 is engaged with the frame 620 alignment feature 940 is positioned within chamber 774 and oriented to correctly orient automatically adjusting headgear mechanism 1000 for operation. Lower lip 950 and inner lip 960 may extend from rear surface 950 and along with alignment feature 940 are configured to support and orient automatically adjusting headgear mechanism 1000 when it is positioned within insert 780. When insert 780 is in position on frame 620, lower lip 950 is configured to close opening 775 of chamber 774 in insert recess 770. Alignment feature 940 may comprise a protrusion, lug, or abutment, shaped to fit within a corresponding alignment feature in the housing of automatically adjusting headgear mechanism 1000 comprising cavity 1010. A cavity 1010 may be present on one or both sides of the housing of automatically adjusting headgear mechanism 1000, configured to engage corresponding alignment features both on rear surface 910 (alignment features 940) and in chamber 774 (not shown). On rear surface 910, alignment feature 940 is located adjacent lower lip 950 and spaced from filament passage 930 and inner lip 960. In an alternative embodiment, the housing of automatically adjusting headgear mechanism 1000 may be integral with the rear surface 910. In such an embodiment alignment feature 940, lower lip 950, and inner lip 960 are omitted. In either embodiment, the housing of automatically adjusting headgear mechanism 1000 may comprise cavity 1010 to engage with a corresponding alignment feature (not shown) within chamber 774.

Insert 780 comprises first end 970 and a second end 980. First end 970 comprises optional over-moulding or strap material attachment feature 920 configured to attach to or be attached to components of a corresponding headgear, such as a polymeric side strap, a textile side strap, or a polymeric side strap with a textile cover, and filament passage 930 that allows a filament to pass through the insert and engage a corresponding headgear as described above. The width of the insert 780 may taper along its length to follow the curvature of shelf 771 and side edges 720 of the frame 620. For example, as shown in the illustrated embodiment, the insert 780 may be wider at the first end 970 than the second end 980.

Figure 44A:
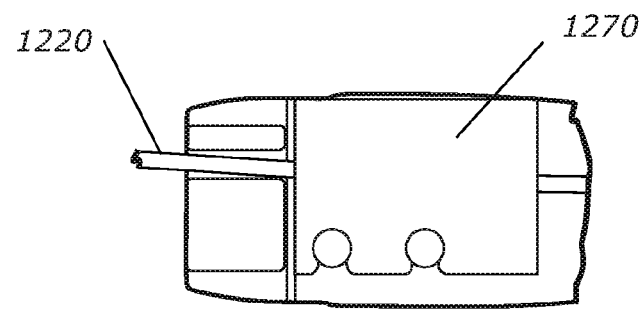
FIGS. 44A-44D show embodiments of automatically adjusting headgear mechanisms used herein.
Figure 44B:
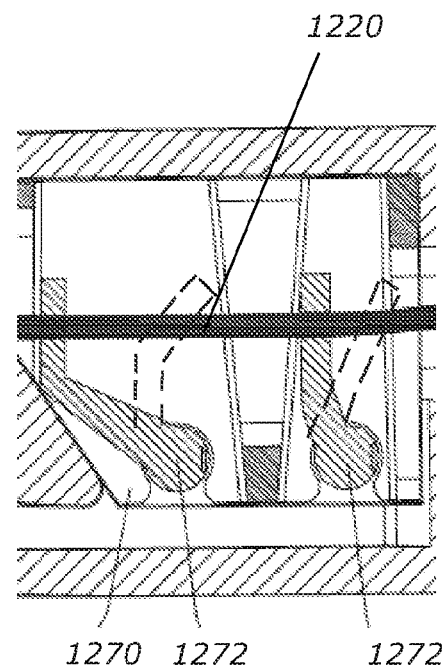
Figure 44C:
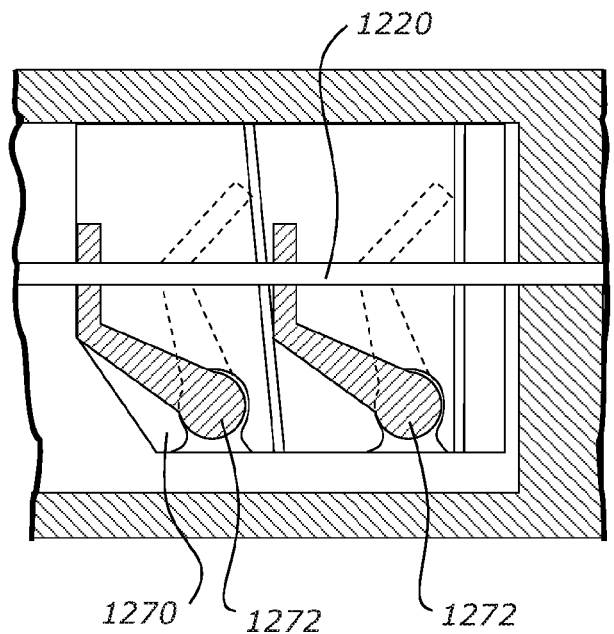
Figure 44D:
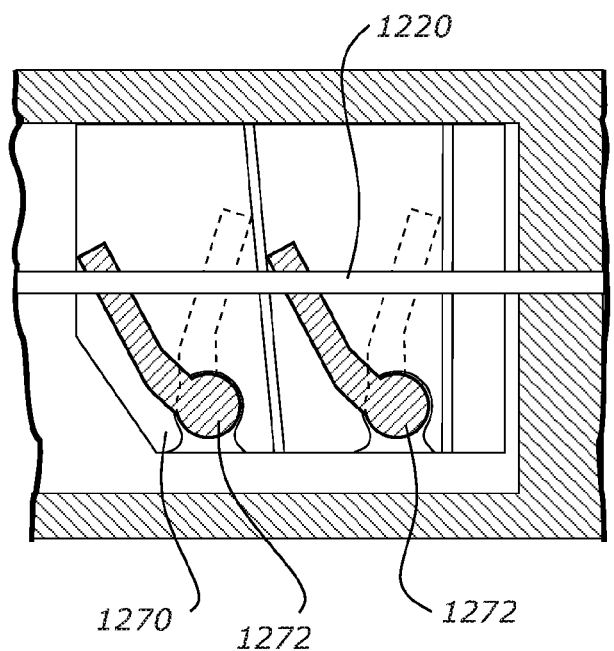

FIGS. 44A-D show an automatically adjusting headgear mechanism 1000 that may be used with any embodiment described herein. Automatically adjusting headgear mechanism 1000 comprises housing 1270 that houses one or more lock members 1272 that act as part of a locking mechanism for the automatically adjusting headgear mechanism 1000. Filament 1220 extends through an aperture in lock member(s) 1272 as shown. Lock members 1272 may be the same (FIGS. 44C and 44D) or different (FIG. 44B). When lock members 1272 are in the position illustrated in solid lines with an axis of the lock member apertures aligned or more closely aligned with a longitudinal axis of the filament 1220, the filament 220 is able to move through the apertures of the lock members 1272 with a relatively low amount of resistance in a direction from right to left in FIG. 44B, C, or D, or in a direction tending to reduce a circumference of the associated headgear or a length of a portion or strap of the headgear. This position of the lock members 1272 can be referred to as a released or unlocked position of the lock members 1272 or the automatically adjusting headgear mechanism 1000. In response to movement of the filament 1220 in the opposite direction (left to right in FIG. 44B, C, or D or in a direction tending to increase the circumference of the associated headgear or length of a portion or strap of the headgear), the lock members 1272 move with the filament 1220 to or toward a position shown in dashed lines in which the resistance to movement is relative greater than the released position as a result of frictional contact between the lock members 1272 and the filament 1220. This position of the lock members 1272 can be referred to as a locked position of the lock members 272 or the automatically adjusting headgear mechanism 1000. Preferably, the resistance to movement of the filament 1220 in the locked position is sufficient to resist blow-off forces created by the pressurized gas within the interface for a given therapy taking into account the overall arrangement of the headgear (e.g., the number of automatically adjusting headgear mechanisms 1000 employed). Other variations of the illustrated automatically adjusting headgear mechanism 1000 or other types of directional locks could also be employed. Examples of such locking mechanisms are shown and described in PCT Publication No. WO2017/158544 and U.S. Publication No. 2016/0082217, the entireties of which are incorporated by reference herein.

Figure 21A:
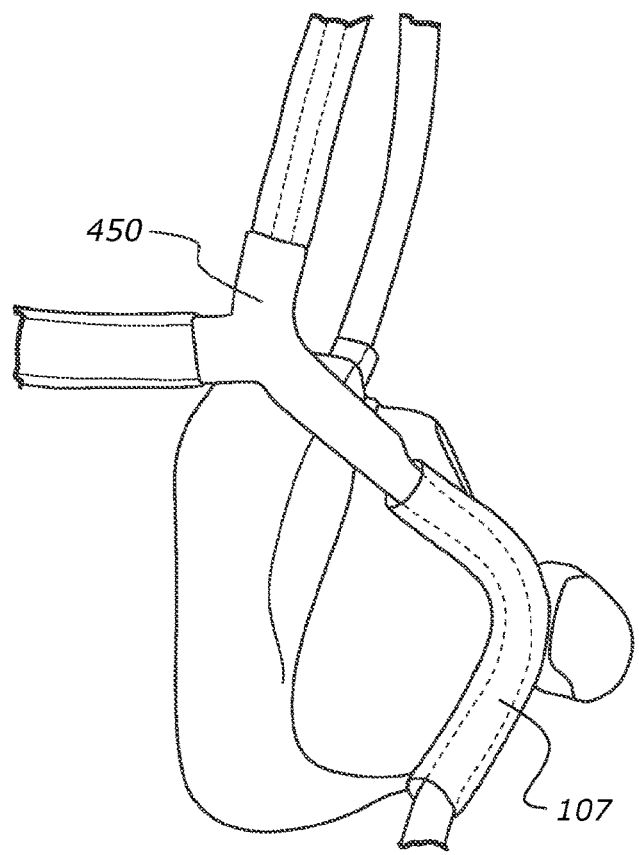
FIGS. 21A and 21B show a portion of the mask assembly of FIG. 19 in a docked position.
Figure 21B:
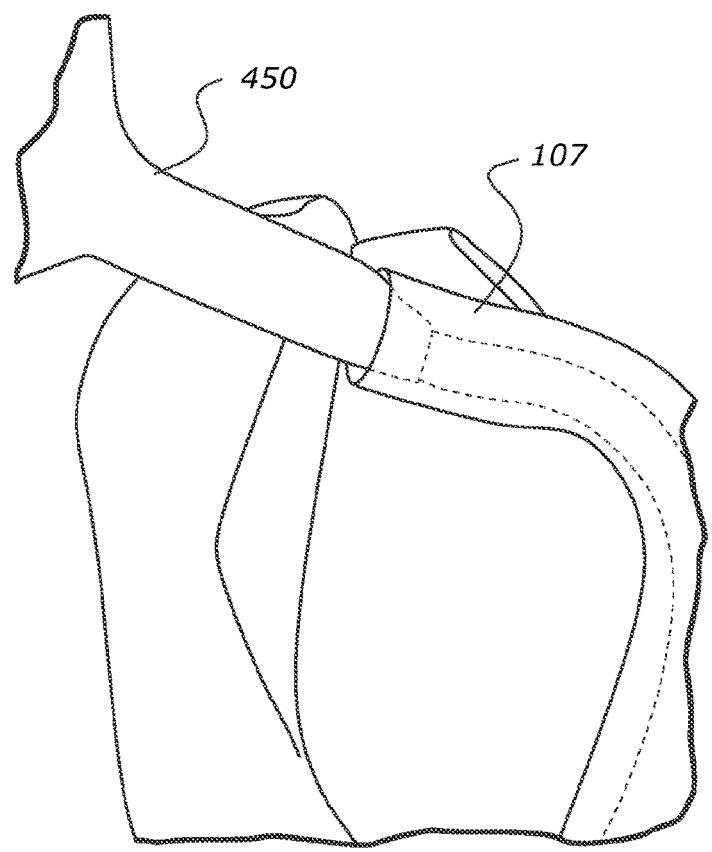
Figure 22A:
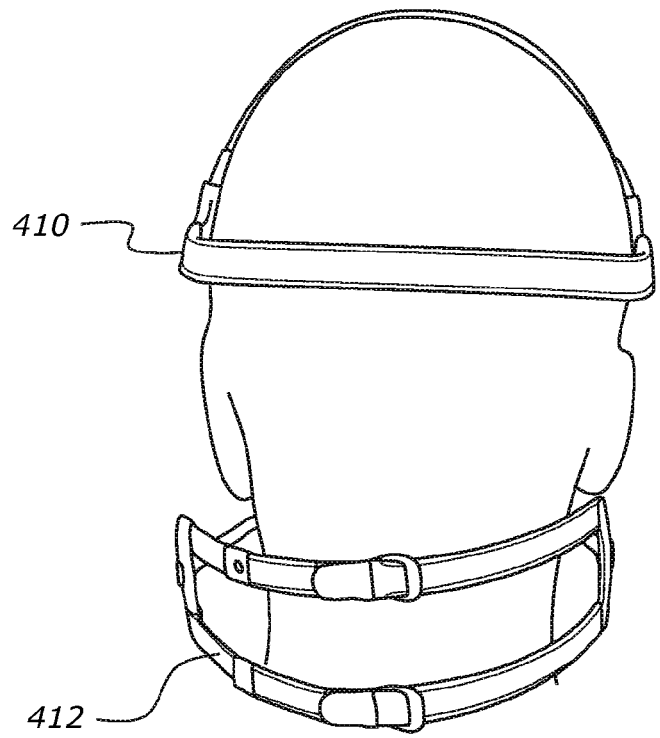
FIG. 22A is a rear view of the mask assembly of FIG. 19 with a lower rear section of a headgear assembly of the mask assembly at a maximum size.
Figure 22B:
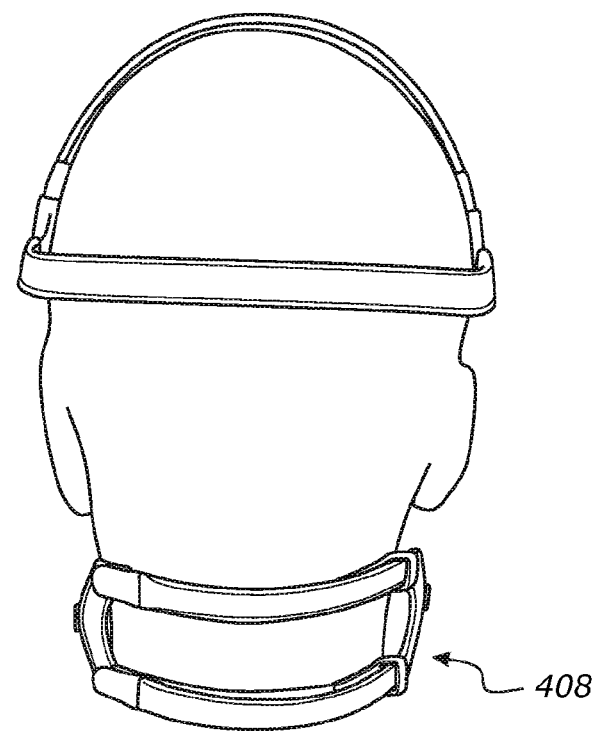
FIG. 22B is a rear view of the mask assembly of FIG. 19 with a lower rear section of a headgear assembly of the mask assembly at a minimum size.
Figure 23A:
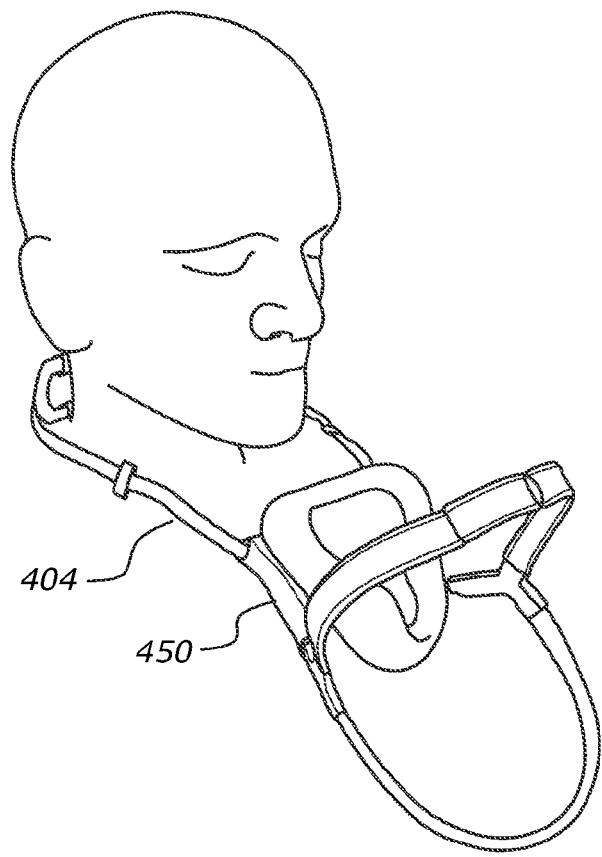
FIG. 23A shows a first stage of a donning process of the mask assembly of FIG. 19.
Figure 23B:
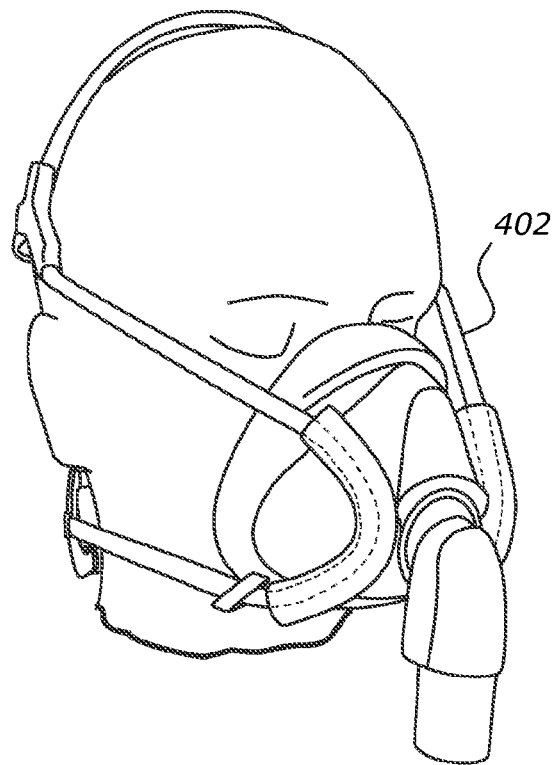
FIG. 23B shows a final stage of the donning process of the mask assembly of FIG. 19.
Figure 24A:
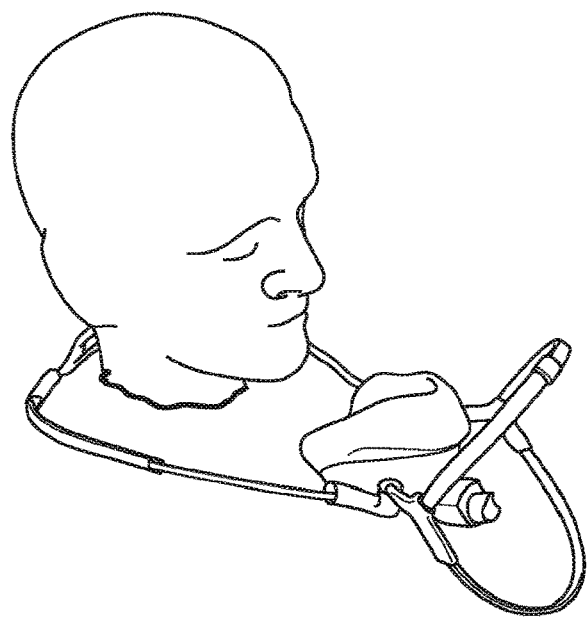
FIGS. 24A-24D show the donning process of the mask assembly of FIG. 19.
Figure 24B:
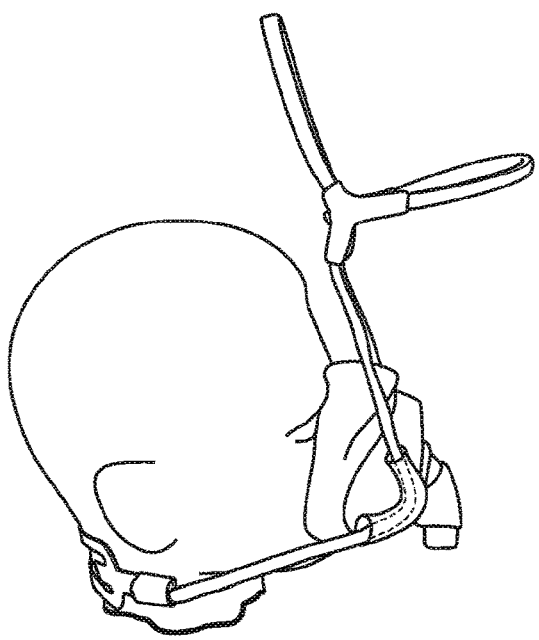
Figure 24C:
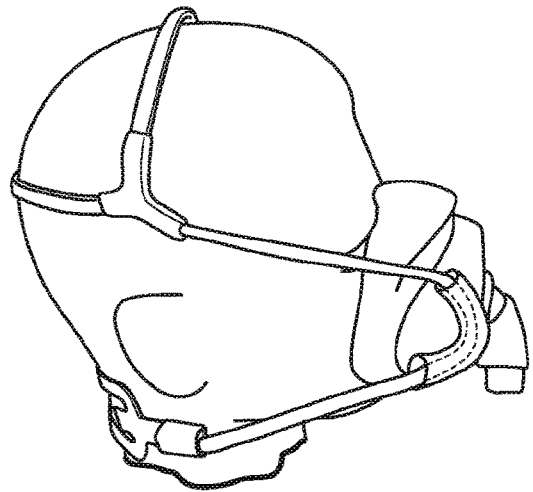
Figure 24D:
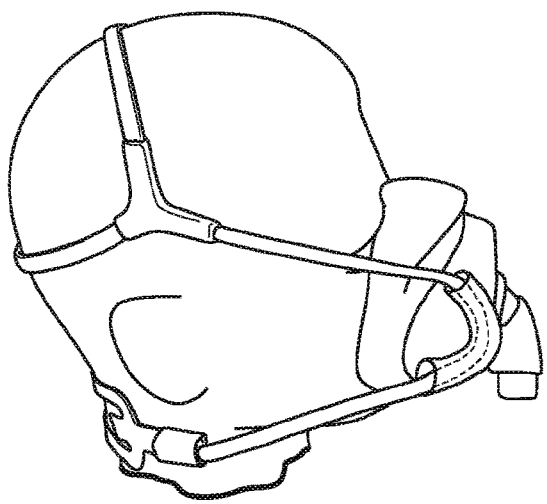

FIGS. 19-22B illustrate another embodiment of a mask assembly including a mask interface 102 and a headgear 400. The headgear 400 includes a pair of side straps 401, a top strap 406, an upper rear strap 410, and a lower rear section 408. Each side strap 401 has an upper portion 402 and a lower portion 404 as described in greater detail herein. Each lower portion 404 is connected (e.g., permanently connected) and extends from one lateral side of the lower rear strap 412. The top strap 406 can be adjustable or non-adjustable. The upper rear strap 410 can be rigid and/or non-adjustable. The lower rear section 408 can include one or more lower rear straps 412. In the illustrated embodiment, the lower rear section 408 includes two lower rear straps 412. The lower rear strap(s) 412 can be adjustable. For example, the lower rear strap(s) 412 can include an adjustment mechanism the same as or similar to that of the top strap 106 shown in, for example, FIGS. 1-2. Other adjustment mechanisms are also possible. FIG. 22A shows the lower rear straps 412 at their maximum length or size, and FIG. 22B shows the lower rear straps 412 at the minimum length or size.

The headgear 400 also includes two connectors 450 housing control mechanisms that are part of an automatically adjustable headgear mechanism as described herein. One connector 450 is positioned on each side of the user's head above the user's ear in use. The connectors 450 can be generally Y-shaped as shown. A first limb of each connector 450 is coupled to the upper portion 402 of one of the side straps 401, a second limb is coupled to one end of the top strap 406, and a third limb is coupled to one end of the upper rear strap 410. A filament extends within each of the side straps 401, through the respective connector 450 and associated control mechanism, and into, along, and/or parallel to the top strap 406, e.g., in a filament storage sleeve 456 that may extend in, along, and/or parallel to the top strap 406.

In the embodiment of FIGS. 19-22B, the upper portion 402 and lower portion 404 of each side strap 401 forms a continuous strap having a braided element and a filament extending within the braided element. The mask interface 102, e.g., the housing 106, includes two passages or channels 107, e.g., in the form of tubes in the illustrated embodiment, one on each side of the mask interface 102. The passages 107 can be curved as shown. For example, the passages 107 can be outwardly and/or rearwardly-facing concave. In the illustrated embodiment, each passage or tube 107 has an upper and lower opening. The upper and lower openings are located towards the face contacting side of the interface. Each side strap 401 extends from one of the connectors 450, forward across the user's face in use (e.g., across the cheek bone region), through one of the passages 107, and back toward the back of the patient's neck to connect to the lower rear strap 412. The upper portion 402 of each side strap 401 is or includes the portion of the side strap 401 between the connector 450 and the passage 107 (e.g., an upper end of the passage 107). The lower portion 404 is or includes the portion of the side strap 401 between the passage 107 (e.g., a lower end of the passage 107) and the lower rear strap 412.

The side straps 401 can move relative to, e.g., slide through, the passages 107. In other words, the passages 107 can slide along the side straps 401. The relative sizes of the upper 402 and lower 404 portions can therefore be adjusted. This relative size adjustment can help allow the user to don the mask assembly in a comfortable manner. The passages 107 are designed and manufactured to have a low enough friction between the passage 107 and side strap 401 to allow the side strap 401 to slide within the passage 107. For example, the radius of curvature of the passage 107 may affect the friction between the passage 107 and side strap 401. The passages 107 are preferably free or reasonably free of sharp or rough edges or spots that could snag the side strap 401, particularly when the braided element is stretch or extended during use. In use, the filaments pin or press the braided elements of the side straps 401 to the walls of the passages 107 due to tension forces of the headgear 400. This creates a friction force that allows angular adjustments to be made to the mask interface 102 as the friction force can maintain the angle of the mask interface 102 relative to the headgear 400 and/or user's head.

A stop or blocking element, for example, in the form of a braid clip in the illustrated embodiment, 458 is attached, e.g., permanently attached, to the lower portion 404 of each side strap 401. The blocking element s 458 are larger than the lower opening of the passages 107 in at least one dimension such that the blocking element 458 cannot pass into or through the passage 107. The blocking element 458 therefore limits the degree or amount of relative movement between the side strap 401 and mask interface 102 and maintains a minimum length of the lower portion 404, for example, during donning and/or doffing. The blocking element 458 can be attached to only the braided element such that the filament can still travel within the braided element unrestricted by the blocking element 458. In some embodiments, a crimp is placed on the filaments, and the crimp cannot slide freely through the blocking element 458. The crimp could therefore help maintain a minimum length of filament in the lower portion 404, for example, during donning and/or doffing.

The lower rear strap 412 sits or rests on or against the back of the user's neck in use. The lower rear strap 412 is adjustable to allow for macro or larger scale adjustments of the headgear size. The automatic adjustment mechanisms, including the braided elements and filaments of the side straps 401 and the control mechanisms within the connectors 450, allow for micro, finer, or smaller scale adjustments to the headgear size. The degree of adjustment allowed or accommodated by the automatic adjustment mechanisms is at least partially dependent on the amount of filament storage available in the headgear and the elasticity of the braided element.

The mask assembly can be adjusted to a "docked" position in which the connectors 450 are partially inserted into the passages, e.g., tubes, 107 for shipping and/or storage, as shown in FIGS. 21A-21B. The docked position advantageously secures at least part of the headgear assembly 400 to the mask interface 102 and/or provides some protection to the face contacting portion of the seal 104. The docked position can provide a convenient starting position for donning the mask assembly more quickly and easily.

Figure 19:
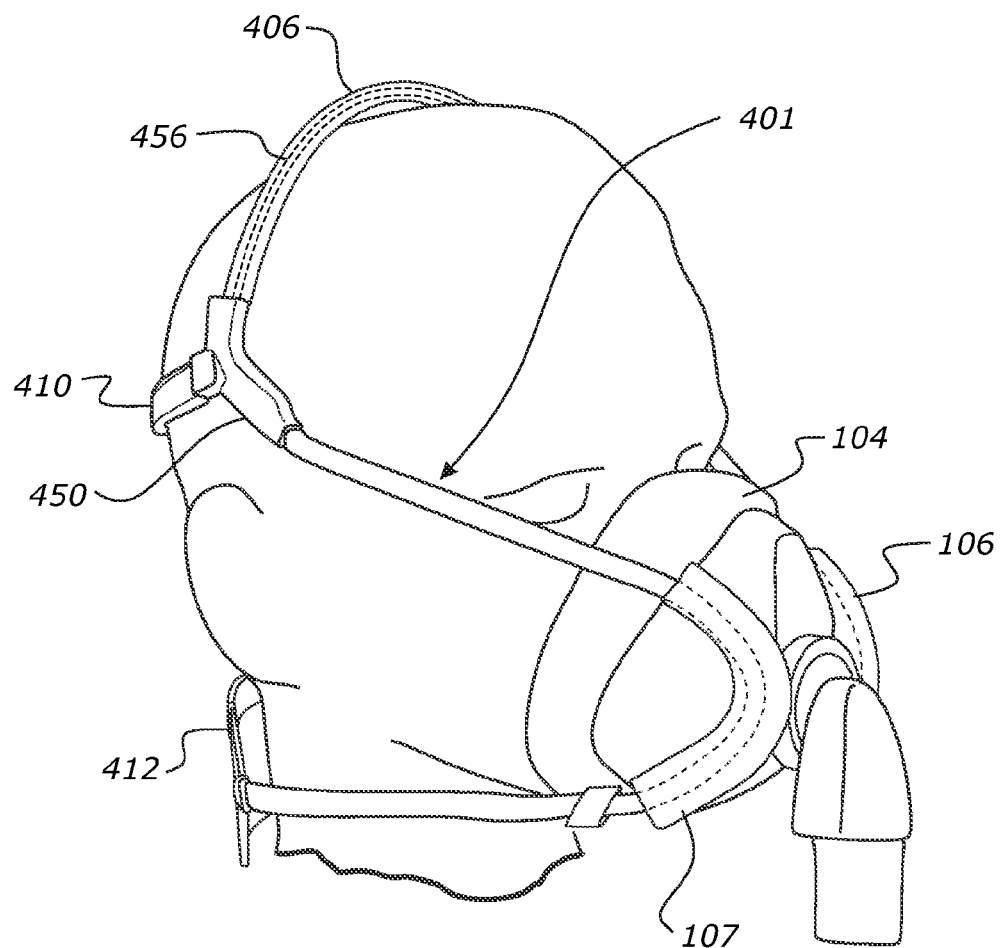
FIG. 19 is a side-front perspective view of an alternative mask assembly.
Figure 20:
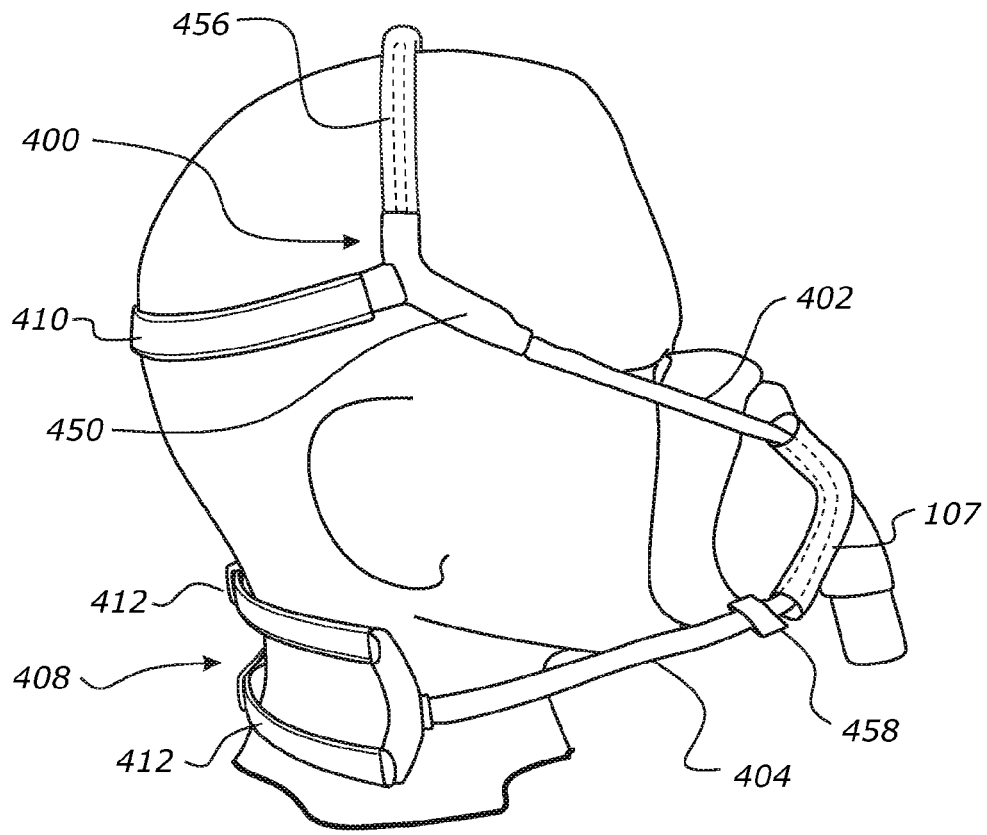
FIG. 20 is a side view of the mask assembly of FIG. 19.

FIGS. 23A-24D illustrate a donning process of the mask assembly of FIG. 19. In a first stage, shown in FIG. 23A, with the connectors 450 in the docked position such that the lower portions 404 of the side straps 401 are at their maximum length or size (and the upper portions 402 are at their minimum length or size), the mask assembly is placed around the user's neck (e.g., by pulling the mask assembly over the user's head) such that the lower rear section 408, side straps 401, and mask interface 102 form a loop around the user's neck. In this position, the mask interface can hang from the user's neck, e.g., with the seal 104 resting against the user's chest, in a "ready position." Next, the user can grasp the upper rear strap 410 and pull the top strap 406 over and/or on top of the user's head, for example, similar to pulling on a baseball cap. During this stage, the connectors 450 are undocked from the passages, e.g., tubes, 107, and some of the slack or length of the side straps 401 is removed from the lower portions 404 such that the upper portions 402 increase in length or size, so that the seal 104 can be positioned over the nose and/or mouth. The user can therefore place the mask assembly in the "ready position" and leave it in this ready position as long as desired, then continue with the donning process when ready for bed. The automatic headgear adjustment mechanisms can then allow for further adjustment. The lower rear section 408 and/or top strap 406 can be adjusted as needed. The lower rear section 408 and/or top strap 406 can allow for larger scale adjustments, and the automatic adjustment mechanisms can then allow for finer, smaller scale adjustments.

Figure 28:
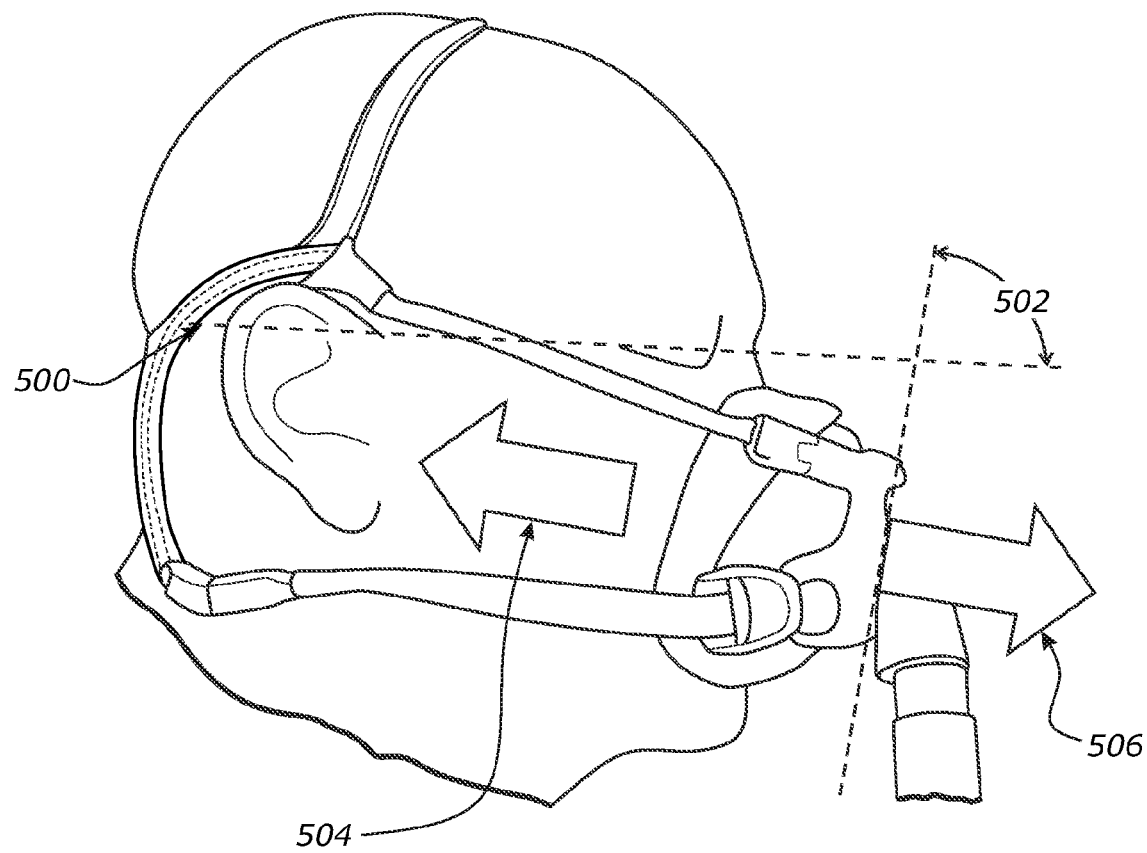
FIGS. 28 and 29 shows angular adjustment allowed by mask assemblies as shown and described herein.
Figure 29:
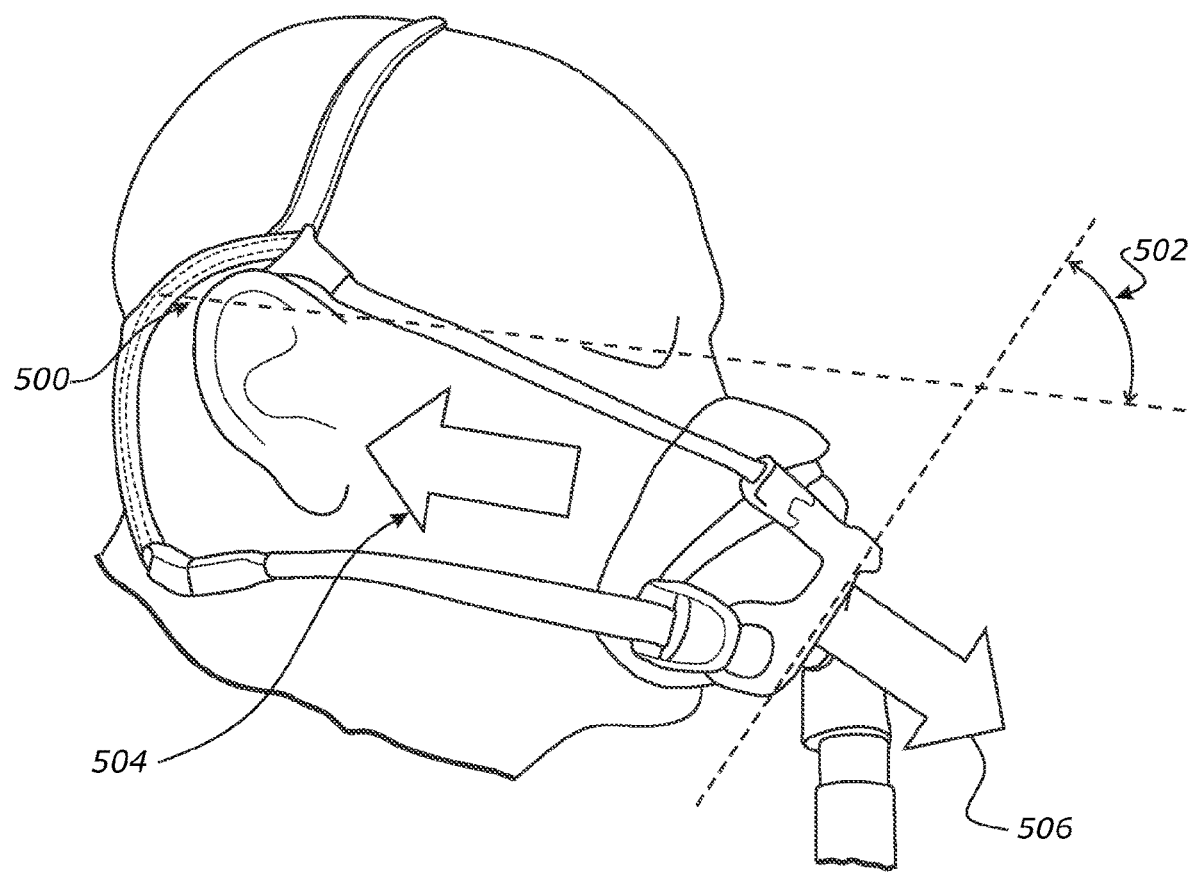
Figure 30:
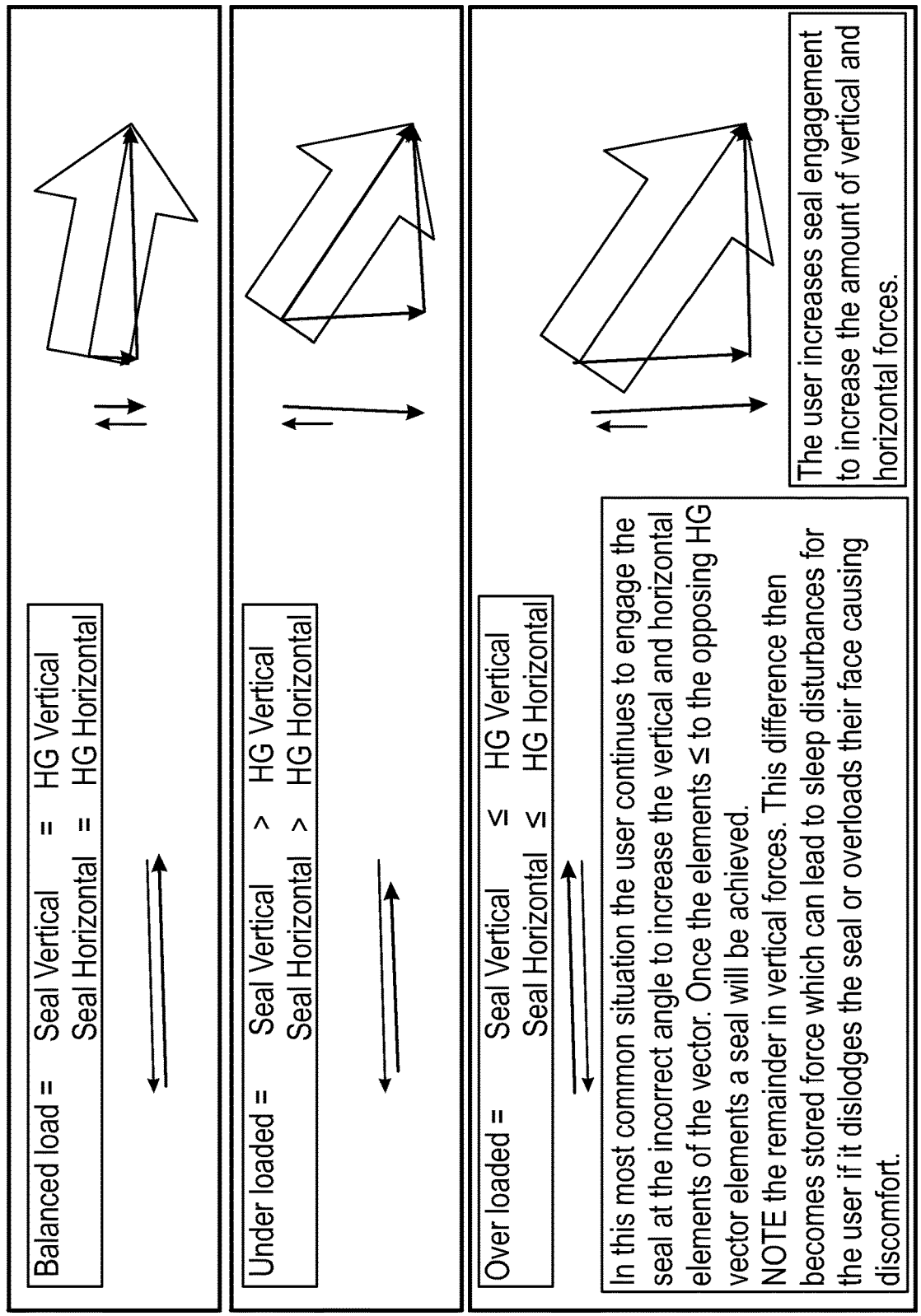
FIG. 30 shows force vectors of the angular adjustment allowed by mask assemblies as shown and described herein.
Figure 31:
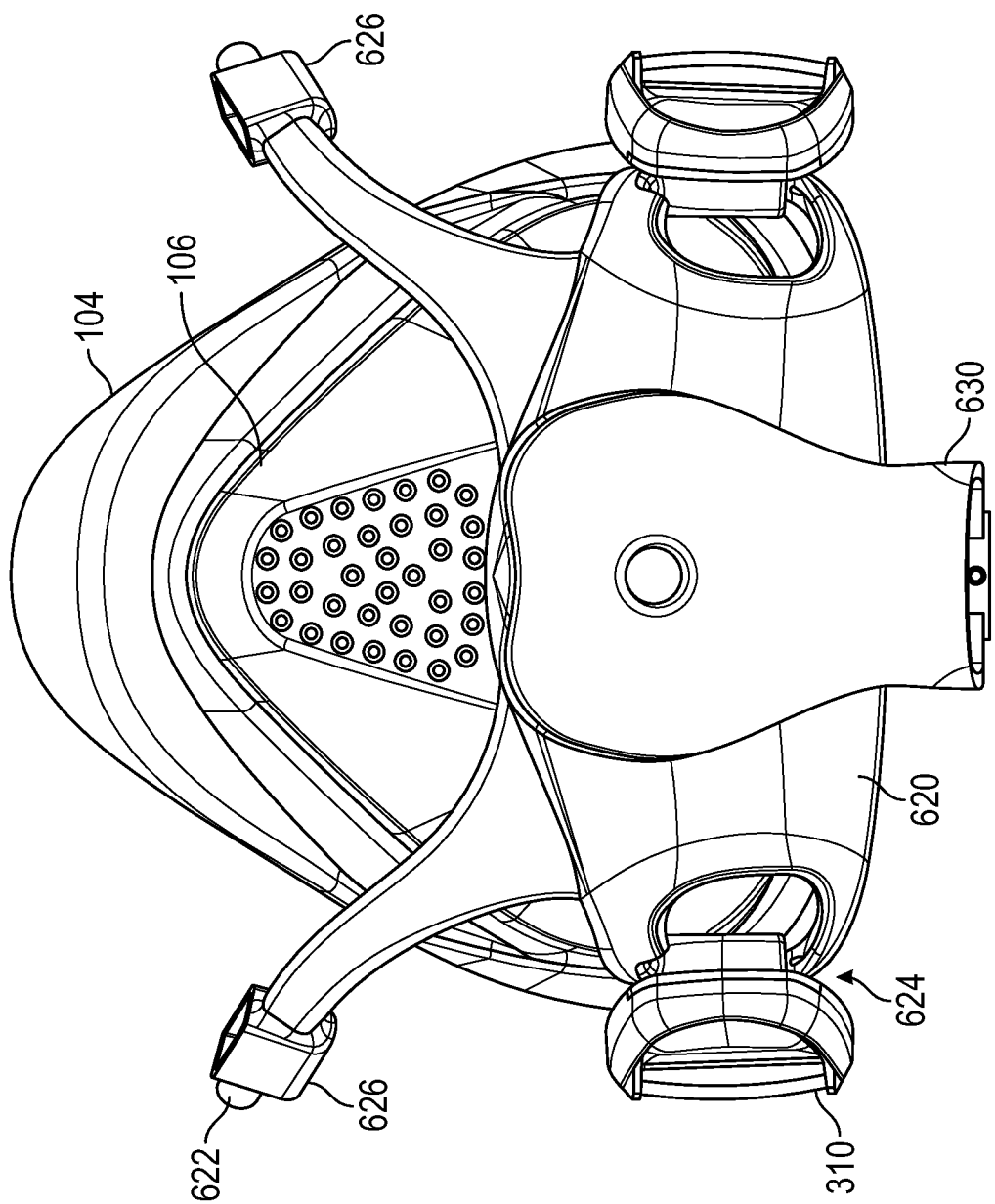
FIG. 31 shows a front view of an alternative embodiment of a mask assembly including a removable frame.

The automatic headgear adjustment mechanisms described herein advantageously allow for small and precise angular adjustment of the mask interface 102 relative to the headgear and the user's face in use simply by manually moving or adjusting the mask interface 102, e.g., by wiggling the mask interface 102. Movement of the mask interface 102 to a new position is maintained by the automatic headgear adjustment mechanisms described herein. For example, if a portion (e.g., the upper portion) of the mask interface 102 is moved toward the user's face, the corresponding portion or straps (e.g., the upper straps 202 are automatically adjusted (shortened) as a result of the biasing element(s) (elastic elements 334 or springs 340) and the directional locks then maintain the portion or straps in the newly adjusted position. The user can therefore adjust the angle of the mask interface 102 and seal 104 relative to the face such that the headgear resultant force opposes or compensates for mask blow-off forces. For example, FIG. 28 illustrates a reference plane 500, an angle 502 of the seal 104 relative to the reference plane 500, the headgear resultant force vector 504, and the mask blow-off force vector 506. As shown, the headgear resultant force vector 504 and mask blow-off force vector 506 are equal and opposite, which results in a balanced fit with reduced, minimal, or no residual forces to optimize the fit of the mask. A balanced fit position can be a position or length (size) of the headgear at which the retention force of the headgear balances with the force induced by the therapy (e.g., blow-off force) and/or other forces (e.g., hose pull forces) attempting to elongate the headgear. In FIG. 29, the mask blow-off force vector 506 has been shifted via the angular adjustment allowed by the automatic headgear adjustment mechanism. The angular adjustment advantageously allows the user to find a position of the mask that is comfortable and offers a balanced fit to reduce unnecessary headgear tension forces. The user advantageously has improved control over the vertical and horizontal axis forces, which allows for minor fine tuning to find the improved or optimized fit compared to a traditional four-point headgear with only traditional adjustment straps, each of which are difficult to precisely adjust in small increments. Furthermore, angular adjustments to the mask as a whole are accomplished by the combination of separate strap adjustments, which can be difficult for a user to determine which straps to adjust and by how much to achieve the desired angular adjustment. Without the availability of precise angular adjustment, the user typically increases the force of the seal 104 against the face to match the blow-off forces. Such excess forces can cause the seal 104 to feel unsettled.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to". Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

The term "plurality" refers to two or more of an item. Recitations of quantities, dimensions, sizes, formulations, parameters, shapes and other characteristics should be construed as if the term "about" or "approximately" precedes the quantity, dimension, size, formulation, parameter, shape or other characteristic. The terms "about" or "approximately" mean that quantities, dimensions, sizes, formulations, parameters, shapes and other characteristics need not be exact, but may be approximated and/or larger or smaller, as desired, reflecting acceptable tolerances, conversion factors, rounding off, measurement error and the like and other factors known to those of skill in the art. Recitations of quantities, dimensions, sizes, formulations, parameters, shapes and other characteristics should also be construed as if the term "substantially" precedes the quantity, dimension, size, formulation, parameter, shape or other characteristic. The term "substantially" means that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

Numerical data may be expressed or presented herein in a range format. It is to be understood that such a range format is used merely for convenience and brevity and thus should be interpreted flexibly to include not only the numerical values explicitly recited as the limits of the range, but also interpreted to include all of the individual numerical values or sub-ranges encompassed within that range as if each numerical value and sub-range is explicitly recited. As an illustration, a numerical range of "1 to 5" should be interpreted to include not only the explicitly recited values of about 1 to about 5, but should also be interpreted to also include individual values and sub-ranges within the indicated range. Thus, included in this numerical range are individual values such as 2, 3 and 4 and sub-ranges such as "1 to 3," "2 to 4" and "3 to 5," etc. This same principle applies to ranges reciting only one numerical value (e.g., "greater than 1") and should apply regardless of the breadth of the range or the characteristics being described.

A plurality of items may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. Furthermore, where the terms "and" and "or" are used in conjunction with a list of items, they are to be interpreted broadly, in that any one or more of the listed items may be used alone or in combination with other listed items. The term "alternatively" refers to selection of one of two or more alternatives, and is not intended to limit the selection to only those listed alternatives or to only one of the listed alternatives at a time, unless the context clearly indicates otherwise.

Reference to any prior art in this specification is not, and should not be taken as, an acknowledgement or any form of suggestion that that prior art forms part of the common general knowledge in the field of endeavour in any country in the world.

Where, in the foregoing description reference has been made to integers or components having known equivalents thereof, those integers are herein incorporated as if individually set forth.

The invention may also be said broadly to consist in the parts, elements and features referred to or indicated in the specification of the application, individually or collectively, in any or all combinations of two or more of said parts, elements or features.

It should be noted that various changes and modifications to the presently preferred embodiments described herein will be apparent to those skilled in the art. Such changes and modifications may be made without departing from the spirit and scope of the invention and without diminishing its attendant advantages. For instance, various components may be repositioned as desired. It is therefore intended that such changes and modifications be included within the scope of the invention. Moreover, not all of the features, aspects and advantages are necessarily required to practice the present invention. Accordingly, the scope of the present invention is intended to be defined only by the claims that follow.

What is claimed is:

1. A respiratory mask assembly comprising:
   a mask interface comprising:
      a housing;
      a seal coupled to the housing, the seal configured to seal on a user's face in use; and
   a removable frame comprising two upper headgear connector arms and two lower headgear connector arms, the removable frame being generally quadrilateral in shape and comprises a front surface and a rear surface, each having an upper edge, a lower edge, and side edges, and wherein the two lower headgear connector arms extend from the rear surface, at, adjacent or spaced from the lower edge of the front surface; and
   a headgear assembly coupled to the mask interface at four locations, the headgear assembly comprising:
      at least two directional locks, one of the at least two directional locks disposed on each side of the user's face in use;
      a headgear comprising:
         an upper side strap configured to be coupled, permanently or removably, to each of the two upper headgear connector arms;
         a first filament extending within the upper side strap;
         a lower side strap configured to be coupled, permanently or removably, to each of the two lower headgear connector arms; and
         a second filament extending within the lower side strap;
      each of the at least two directional locks comprising one or more lock members, the one or more lock members configured to frictionally engage a corresponding one of the first filament or the second filament during elongation of the headgear but allow reduced friction or relatively friction free movement during retraction of the headgear.

2. The respiratory mask assembly of claim 1, wherein the mask interface is a full face mask and the seal is configured to cover a user's nose and mouth in use.

3. The respiratory mask assembly of claim 1, wherein:
   the upper side strap is configured to be permanently coupled to each of the two upper headgear connector arms; and
   the lower side strap is configured to be removably coupled to each of the two lower headgear connector arms.

4. The respiratory mask assembly of claim 1, wherein the removable frame comprises a top edge and two opposing side edges, wherein the top edge and each of the two opposing side edges follow a continuous arc.

5. The respiratory mask assembly of claim 1, wherein the removable frame comprises a gas path positioned within a space defined by a portion of the rear surface of the removable frame.

6. The respiratory mask assembly of claim 5, wherein the removable frame and the gas path are integrated to form a single component.

7. The respiratory mask assembly of claim 1, wherein the front surface is curved and is substantially smooth.

8. The respiratory mask assembly of claim 1, wherein the removable frame comprises insert recesses, each insert recess housing an associated one of the at least two directional locks.

9. The respiratory mask assembly of claim 8, wherein each insert recess is formed in the front surface of the removable frame.

10. The respiratory mask assembly of claim 8, wherein each insert recess comprises a shelf, a mouth, a chamber and a channel that terminates at a blind end.

11. The respiratory mask assembly of claim 10, wherein each insert recess houses a control mechanism.

12. The respiratory mask assembly of claim 11, wherein, in use, the first filament or the second filament can move longitudinally within a corresponding insert recess, with a free end of the first filament or the second filament able to move towards and away from the blind end of the corresponding insert recess, as dictated by motion of the headgear assembly and operation of the associated one of the at least two directional locks.

13. The respiratory mask assembly of claim 10, wherein the headgear assembly further comprises an insert configured to be inserted into one of the insert recesses.

14. The respiratory mask assembly of claim 13, wherein the insert is inserted into one of the insert recesses engaging at least the shelf and providing a cover that forms an enclosed space within said one of the insert recesses.

15. The respiratory mask assembly of claim 13, wherein the insert comprises an alignment feature.

16. The respiratory mask assembly of claim 15, wherein when the insert is engaged with the removable frame, the alignment feature is positioned within a chamber of a corresponding insert recess and oriented to correctly orient the associated one of the at least two directional locks for operation.

17. The respiratory mask assembly of claim 8, wherein each insert recess extends along one of the side edges of the removable frame.

18. The respiratory mask assembly of claim 1, wherein the two upper headgear connector arms and the two lower headgear connector arms are integral with and extend from a central portion of the removable frame.

* * * * *